(12) United States Patent
Livingston et al.

(10) Patent No.: US 12,140,526 B2
(45) Date of Patent: Nov. 12, 2024

(54) METHODS FOR DETECTING PARTICLES PRESENT IN A CELL COMPOSITION

(71) Applicant: Juno Therapeutics, Inc., Seattle, WA (US)

(72) Inventors: Brittney Jo Livingston, Kirkland, WA (US); Hai Yue, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 1082 days.

(21) Appl. No.: 16/970,917

(22) PCT Filed: Feb. 28, 2019

(86) PCT No.: PCT/US2019/020139
§ 371 (c)(1),
(2) Date: Aug. 18, 2020

(87) PCT Pub. No.: WO2019/169194
PCT Pub. Date: Sep. 6, 2019

(65) Prior Publication Data
US 2020/0393355 A1 Dec. 17, 2020

Related U.S. Application Data

(60) Provisional application No. 62/636,840, filed on Feb. 28, 2018.

(51) Int. Cl.
*G01N 15/14* (2024.01)
*G01N 33/543* (2006.01)
*G01N 15/00* (2006.01)

(52) U.S. Cl.
CPC ... *G01N 15/1456* (2013.01); *G01N 33/54313* (2013.01); *G01N 2015/0053* (2013.01)

(58) Field of Classification Search
None
See application file for complete search history.

(56) References Cited

U.S. PATENT DOCUMENTS

| | | |
|---|---|---|
| 4,452,773 A | 6/1984 | Molday |
| 4,490,436 A | 12/1984 | Kawakami |
| 4,554,088 A | 11/1985 | Whitehead |
| 4,654,267 A | 3/1987 | Ugelstad |
| 4,774,265 A | 9/1988 | Ugelstad |
| 4,795,698 A | 1/1989 | Owen |
| 5,091,206 A | 2/1992 | Wang |

(Continued)

FOREIGN PATENT DOCUMENTS

| | | |
|---|---|---|
| CN | 101305087 | 11/2008 |
| CN | 101469310 | 7/2009 |

(Continued)

OTHER PUBLICATIONS

Aarvak et al., "Dynabeads CD3/CD28 CTS™ for T cell isolation, activation and expansion." Poster.

(Continued)

*Primary Examiner* — Hoon K Song
(74) *Attorney, Agent, or Firm* — Morrison & Foerster LLP

(57) ABSTRACT

Provided are methods of detecting, assessing or determining the presence or absence of particles, such as bead particles, present in a cell composition. Also provided are articles of manufacture and kits for use in the methods.

36 Claims, 8 Drawing Sheets

(56) References Cited

U.S. PATENT DOCUMENTS

| | | | |
|---|---|---|---|
| 5,200,084 | A | 4/1993 | Liberti |
| 5,232,782 | A | 8/1993 | Charmot |
| 5,283,079 | A | 2/1994 | Wang |
| 5,318,797 | A | 6/1994 | Matijevic |
| 5,356,713 | A | 10/1994 | Charmot |
| 5,395,688 | A | 3/1995 | Wang |
| 5,583,054 | A | 12/1996 | Ito et al. |
| 5,834,121 | A | 11/1998 | Sucholeiki |
| 6,040,177 | A | 3/2000 | Riddell |
| 6,074,884 | A | 6/2000 | Siiman et al. |
| 6,342,396 | B1 | 1/2002 | Perrin et al. |
| 7,465,579 | B2 | 12/2008 | Hatakeyama et al. |
| 8,012,750 | B2 | 9/2011 | Har-Noy et al. |
| 8,218,141 | B2 | 7/2012 | Zimenkov et al. |
| 8,398,741 | B2 | 3/2013 | Kaneko |
| 9,557,217 | B2 | 1/2017 | Zimenkov et al. |
| 11,561,219 | B2 * | 1/2023 | Khuu-Duong ... G01N 33/54333 |
| 2005/0277159 | A1 | 12/2005 | Lehmann et al. |
| 2007/0026381 | A1 | 2/2007 | Huang et al. |
| 2008/0317724 | A1 | 12/2008 | Kam et al. |
| 2009/0156932 | A1 | 6/2009 | Pavlovich et al. |
| 2010/0207051 | A1 | 8/2010 | Fonnum et al. |
| 2011/0003380 | A1 | 1/2011 | Miltenyi |
| 2013/0330716 | A1 | 12/2013 | Fabien et al. |
| 2014/0170678 | A1 | 6/2014 | Kasdan et al. |
| 2018/0291432 | A1 * | 10/2018 | Parvin ............... C12Q 1/6841 |
| 2023/0131940 | A1 | 4/2023 | Khuu-Duong et al. |

FOREIGN PATENT DOCUMENTS

| | | |
|---|---|---|
| CN | 102516178 | 6/2012 |
| CN | 105200007 | 12/2015 |
| CN | 205279665 | 6/2016 |
| EP | 452342 | 10/1991 |
| EP | 1257632 | 11/2002 |
| EP | 1348943 | 10/2003 |
| EP | 3 086 110 | 10/2016 |
| JP | 2007254465 | 10/2007 |
| JP | 2007503377 | 7/2012 |
| WO | WO 1994/029436 | 12/1994 |
| WO | WO 1999/024045 | 5/1999 |
| WO | WO 1999/054439 | 10/1999 |
| WO | WO 2001/062895 | 8/2001 |
| WO | WO 2002/006790 | 1/2002 |
| WO | WO 2005/018667 | 8/2004 |
| WO | WO 2005/051990 | 6/2005 |
| WO | WO 2005/108589 | 11/2005 |
| WO | WO 2005/113003 | 12/2005 |
| WO | WO 2006/037649 | 4/2006 |
| WO | WO 2008/041004 | 4/2008 |
| WO | WO 2008/052338 | 5/2008 |
| WO | WO 2009/072003 | 6/2009 |
| WO | WO 2010/057318 | 5/2010 |
| WO | WO 2010/099205 | 9/2010 |
| WO | WO 2010/140127 | 12/2010 |
| WO | WO 2011/109440 | 9/2011 |
| WO | WO 2012/064878 | 5/2012 |
| WO | WO 2014/138887 | 9/2014 |
| WO | WO 2014/151763 | 9/2014 |
| WO | WO 2014/191003 | 12/2014 |
| WO | WO 2016/090190 | 6/2016 |
| WO | WO 2018/013797 | 1/2018 |

OTHER PUBLICATIONS

Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.

Entschladen et al., "Differential requirement of protein tyrosine kinases and protein kinase C in the regulation of T cell locomotion in three-dimensional collagen matrices," J Immunol. (1997) 159(7):3203-3210.

Evans et al., "High-permeability functionalized silicone magnetic microspheres with low autofluorescence for biomedical applications." Mater Sci Eng C Mater Biol Appl. (2016) 62: 860-869.

Friedl et al., "T lymphocyte locomotion in a three-dimensional collagen matrix: Expression and function of cell adhesion molecules," J Immunol. (1995) 154:4973-4985.

Giouroudi et al., "Microfluidic Biosensing Systems Using Magnetic Nanoparticles," Int J Mol Sci., (2013) 14(9): 18535-18556.

Hollyman et al., "Manufacturing validation of biologically functional T cells targeted to CD19 antigen for autologous adoptive cell therapy," J Immunother. (2009) 32(2):169-180.

Kinosita et al., "Hemolysis of human erythrocytes by a transient electric field," Proc. Natl. Acad. Sci., (1977) 74:1923-7.

Klamp et al., "Highly Rapid Amplification-Free and Quantitative DNA Imaging Assay." Scientific Reports. (2013) 3(1852): 1-7.

Klamp et al., "Highly Rapid Amplification-Free and Quantitative DNA Imaging Assay." Supplementary Information. Scientific Reports. 2013. 3(1852): 1-7.

Klebanoff et al., "Sorting through subsets: Which T cell populations mediate highly effective adoptive immunotherapy?," J Immunother. (2012) 35(9): 651-660.

Koga et al., "Usefulness of Immuno-Magnetic Beads conjugated with Anti-EpCAM Antibody for Detecting Endometrial Cancer Cells." Journal of Cancer Therapy. 2013. 4: 1273-1282.

Labarriere et al., "A full GMP process to select and amplify epitope-specific T lymphocytes for adoptive immunotherapy of metastatic melanoma," Clin Dev Immunol. (2013) 2013: 932318 (11 pgs).

Li et al., "Comparison of anti-CD3 and anti-CD28-coated beads with soluble anti-CD3 for expanding human T cells: Differing impact on CD8 T cell phenotype and responsiveness to restimulation," J Transl Med., (2010) 8:104.

Mescher, "Surface contact requirements for activation of cytotoxic T lymphocytes," J. Immunol., (1992) 149(7):2402-2405.

Molecular Probes CAL-LYSE Lysing Solution User guide (Catalog Nos. GAS-010, GAS-010S-100).

Molecular Probes CountBright Absolute Counting Beads *for flow cytometry* Product Information (MP 36950).

Prufer et al., "Oxidative burst and neutrophil elastase contribute to clearance of Aspergillus fumigatus pneumonia in mice." Immunobiology. Feb. 2014;219(2):87-96.

Steenbloc and Fahmy, "A comprehensive platform for ex vivo T-cell expansion based on biodegradable polymeric artificial antigen-presenting cells," Molecular Therapy, (2008) 16(4):765-772.

Terakura et al., "Generation of CD19-chimeric antigen receptor modified CD8+ T cells derived from virus-specific central memory T cells," Blood. (2012) 119(1):72-82.

Van Der Stegen, "An Investigation into the Potential Toxicity of ErbB Targeting T4 Immunotherapy," Jan. 1, 2013, XP055590657; Retrieved from the Internet: URL:https://core.ac.uk/download/pdf/83946847.pdf; Retrieved on May 21, 2019; Chapter 5.4; Figures 5-3; 314 pgs.

Wang et al., "Phenotypic and Functional Attributes of Lentivirus Modified CD19-specific Human CD8+ Central Memory T Cells Manufactured at Clinical Scale," J Immunother. (2012) 35(9):689-701.

Young et al., "Assessment of enhanced autofluorescence and impact on cell microscopy for microfabricated thermoplastic devices." Anal Chem. (2013) 85(1): 44-49.

Anonymous, "Protocol for the removal of MACS® GMP ExpAct Treg Beads," Miltenyi Biotec, available at https://www.miltenyibiotec.com/upload/assets/IM0017462.PDF, Jul. 2012, retrieved Apr. 11, 2019.

He et al., Medical Research Methodology, People's Military Medical Press, p. 90, published on Oct. 31, 2003 (English translation included).

Li et al., "Clinical signficance of osmolality measurement." Shaanxi Medical Journal (1989) 18 (8): 40-43.

Li et al. "Effect of transcatheter arterial chemoembolization on the circulating tumor cells number and the vascular endothelial growth factor concentration in patients with hepatocellular carcinoma," Chinese Clinical Oncology (2015) 20 (8): 709-712.

(56) References Cited

OTHER PUBLICATIONS

Li et al., "Expression of plasma vascular endothelial growth factor in patients with hepatocellular carcinoma and effect of transcatheter arterial chemoembolization therapy on plasma vascular endothelial growth factor level," World J Gastroenterol. (2004) 10(19): 2878-82.

Phanse et al., "Analyzing cellular internalization of nanoparticles and bacteria by multi-spectral imaging flow cytometry," J Vis Exp. (2012) (64): e3884.

Won et al., "Flow cytometric detection of erythrocyte osmotic fragility," Cytometry B Clin Cytom. (2009) 76(2): 135-41.

Mualla et al., "Automatic cell detection in Bright-Field microscope images using SIFT, Random Forests, and Hierarchical clustering," IRRR Transactions on Medical Imaging (2013) 32(12):2274-2286.

* cited by examiner

METHODS FOR DETECTING PARTICLES PRESENT IN A CELL COMPOSITION

CROSS-REFERENCE TO RELATED APPLICATIONS

This application is a U.S. National Stage application under 35 U.S.C. § 371 of International Application No. PCT/US2019/020139, filed on Feb. 28, 2019, which claims priority to U.S. provisional application No. 62/636,840, filed Feb. 28, 2018, entitled "METHODS FOR DETECTING PARTICLES PRESENT IN A CELL COMPOSITION," the contents of which are incorporated by reference in their entirety for all purposes.

FIELD

The present disclosure relates to methods of detecting, assessing or determining the presence or absence of particles, such as bead particles, present in a cell composition. Also provided are articles of manufacture and kits for use in the methods.

BACKGROUND

Particles, such as magnetic beads, are used as a surface for immobilization of biomolecules, including affinity reagents, such as antibodies. In some cases, such particles can be used in various methods, such as in detection, selection, enrichment, isolation, and/or stimulation of cells. In some cases, the particles can remain bound to cells or present in the composition containing the cells after such processes. Current methods for detecting the presence or absence of particles in a cell composition can be time-consuming, labor-intensive and/or inaccurate, for determining the actual number of particles bound or associated with a cell or present in a composition. Improved methods for enumerating or detecting particles in a cell composition are needed. Provided herein are methods, compositions, systems, and kits that meet such needs.

SUMMARY

Provided herein are methods, uses, compositions, kits, and articles of manufacture for detecting the presence or absence of non-cell particles in a cell composition. In particular aspects, provided herein is a method, the method comprising the steps of a) incubating a sample comprising at least a portion of an input composition or a sample derived from the input composition, said input composition comprising one or more cells and one or more non-cell particles, wherein the incubating is under conditions to induce lysis of cells to produce an output composition; and b) analyzing the output composition or a portion thereof by fluorescence imaging to determine the presence or absence of particles in the sample.

Also provided herein is a method for detecting the presence or absence of non-cell particles in a cell composition, the method comprising analyzing an output composition or a portion thereof by fluorescence imaging to determine the presence or absence of particles in the sample, wherein the output composition is produced by incubating a sample comprising at least a portion of an input composition or a sample derived from the input composition under conditions to induce lysis of cells, said input composition comprising cells and one or more non-cell particles.

Also provided herein is a method for detecting the presence or absence of non-cell particles in a cell composition, the method comprising the steps of incubating a sample comprising at least a portion of an input composition or a sample derived from the input composition, wherein said input composition comprises one or more cells and is likely to comprise or may comprise one or more non-cell particles in which said one or more non-cell particles is capable of emitting an autofluorescence, wherein the incubating is under conditions to induce lysis of cells to produce an output composition, and analyzing the output composition or a portion thereof by fluorescence imaging of the autofluorescence of the one or more non-cell particles to determine the presence or absence of the one or more non-cell particles in the sample Also provided herein is a method for detecting the presence or absence of non-cell particles in a cell composition, the method comprising analyzing an output composition or a portion thereof by fluorescence imaging of an autofluorescence to determine the presence or absence of non-cell particles in the output composition, wherein the output composition is a sample of at least a portion of an input composition that has been incubated under conditions to induce lysis of cells, wherein the input composition comprises one or more of the cells and is likely to comprise or may comprise one or more non-cell particles in which said one or more non-cell particles is capable of emitting the autofluorescence.

Also provided herein is a method for detecting the presence of absence of non-cell particles in a cell composition, the method comprising processing a cell composition comprising cells and non-cell particles under conditions to remove or reduce the non-cell particles of the cell composition, thereby producing an input composition comprising one or more of the cells and that may comprise one or more non-cell particles that is a residual non-cell particle, wherein the one or more non-cell particles is capable of emitting an autofluorescence, incubating a sample comprising at least a portion of the input composition or a sample derived from the input composition, wherein the incubating is under conditions to induce lysis of the one or more cells to produce an output composition, enriching for the one or more non-cell particles in the output composition by a step involving selecting for the one or more non-cell particles present in the output composition, and analyzing the output composition or a portion thereof by fluorescence imaging of the autofluorescence to determine the presence or absence of non-cell particles in the sample.

In some embodiments, the one or more non-cell particles is a residual non-cell particle present in the input composition following a step to remove or reduce non-cell particles from a cell composition comprising the one or more cells and one or more non-cell particles. In certain embodiments of any of the provided embodiments, prior to the analyzing the output composition is enriched for the one or more non-cell particles. In certain embodiments of any of the provided embodiments, prior to the analyzing the output composition is enriched for the one or more non-cell particles by a step involving selecting for the one or more non-cell particles present in the output composition. In some of the embodiments, the one or more non-cell particles are magnetic or paramagnetic and the selection comprises exposing the non-cell particles to a magnet or magnetic field.

In some embodiments of any of the provided embodiments, the analyzing the output composition by fluorescence imaging comprises obtaining fluorescent micrographs of the output composition or a portion thereof. In some embodiments of any of the provided embodiments, the analyzing the output composition by fluorescence imaging further comprises determining the fluorescent intensity of image objects from the fluorescent micrographs. In some embodiments of any of the provided embodiments, the analyzing the output composition by fluorescence imaging comprises obtaining fluorescent micrographs of the output composition or a portion thereof, and determining fluorescent intensity of image objects from the fluorescent micrographs. In some embodiments of any of the provided embodiments, the fluorescent intensity of image objects is the mean fluorescent intensity of image objects. In certain embodiments of any of the provided embodiments, the method further comprises obtaining brightfield micrographs of the output composition or a portion thereof. In certain embodiments of any of the provided embodiments, the method further comprises obtaining brightfield micrographs of the output composition or a portion thereof, wherein the one or more non-cell particles are distinguished from one or more other components in the output composition by assessing the size, area, and/or circularity of image objects from the fluorescent micrographs and/or brightfield micrographs. In particular embodiments of any of the provided embodiments, the analyzing the output composition further comprises determining the size, area, and/or circularity of image objects from the fluorescent micrographs and/or brightfield micrographs. In certain embodiments of any of the provided embodiments, the output composition does not comprise an agent for detecting the particles. In certain embodiments of any of the provided embodiments, the output composition does not comprise an agent for detecting the particles, wherein the agent is or comprises a detectable moiety or is capable of producing a detectable signal or the analyzing does not comprise adding an agent for detecting the particles to the output composition, wherein the agent is or comprises a detectable moiety or is capable of producing a detectable signal.

Provided herein is a method for detecting the presence or absence of particles in a cell composition, comprising (i) illuminating an output composition or a portion thereof with one or more light sources to generate an illuminated sample, wherein at least one light source is capable of exciting fluorescent molecules; (ii) capturing one or more images of the illuminated sample, wherein at least one image is a fluorescent image; (iii) analyzing the presence or absence of image objects from the one or more images for one or more parameters selected from size, area, fluorescent intensity (FI), brightfield intensity, and/or circularity; wherein the output composition is produced by incubating a sample comprising at least a portion of an input composition or a sample derived from the input composition, said input composition comprising one or more cells and one or more non-cell particles under conditions to induce lysis of the cells.

Provided herein is a method for detecting the presence or absence of non-cell particles in a cell composition, the method comprising (i) illuminating an output composition or a portion thereof with one or more light sources to generate an illuminated sample, wherein at least one light source is capable of exciting an autofluorescence, wherein said output composition is a sample of at least a portion of an input composition that has been incubated under conditions to induce lysis of cells, wherein the input composition comprises one or more of the cells and is likely to comprise or may comprise the one or more non-cell particles in which said one or more non-cell particles is capable of emitting the autofluorescence; (ii) capturing one or more images of the illuminated sample, wherein at least one image is a fluorescent image; (iii) analyzing the presence or absence of image objects from the one or more images for one or more parameters selected from size, area, fluorescent intensity (FI), brightfield intensity, and/or circularity, thereby determining the presence or absence of one or more non-cell particles. In some embodiments of any of the provided embodiments, at least one image is a brightfield image.

In some embodiments of any of the provided embodiments, the fluorescent intensity is the mean fluorescent intensity. In some embodiments of any of the provided embodiments, the brightfield intensity is the mean brightfield intensity. In some embodiments of any of the provided embodiments, prior to the illuminating the output composition is enriched for the one or more non-cell particles. In some embodiments of any of the provided embodiments, prior to the illuminating the output composition is enriched for the one or more non-cell particles by a step involving selection for the one or more non-cell particles present in the output composition. In some embodiments, the selection is for the one or more non-cell particles present in the output composition and wherein the one or more non-cell particles are magnetic or paramagnetic and the selection comprises magnetic selection. In some embodiments of any of the provided embodiments, the analyzing detects singlets, doublets, or singlets and doublets of the non-cell particles.

Also provided herein is a method for detecting the presence or absence of particles in a cell composition, the method comprising the steps of: a) incubating a sample comprising at least a portion of an input composition or a sample derived from the input composition, said input composition comprising one or more cells and one or more non-cell particles, wherein the incubating is under conditions to induce lysis of cells to produce an output composition; and b) optically analyzing the output composition or portion thereof to assess the presence or absence of one or more parameters of one or more image objects, wherein the one or more parameters is selected from size, area, fluorescent intensity (FI), brightfield intensity, and/or particle circularity. In some embodiments of any of the provided embodiments, the fluorescent intensity is the mean fluorescent intensity. In some embodiments of any of the provided embodiments, the brightfield intensity is the mean brightfield intensity.

Provided herein is a method for detecting the presence or absence of particles in a cell composition, the method comprising optically analyzing an output composition or portion thereof to assess the presence or absence of one or more parameters of one or more image objects, said one or more parameters selected from size, area, fluorescent intensity (FI), brightfield intensity, and/or particle circularity, wherein the output composition is produced by incubating a sample comprising at least a portion of an input composition or a sample derived from the input composition under conditions to induce lysis of cells, said input composition comprising cells and one or more non-cell particles. In some embodiments of any of the provided embodiments, the fluorescent intensity is the mean fluorescent intensity. In some embodiments of any of the provided embodiments, the brightfield intensity is the mean brightfield intensity. In certain embodiments of any of the provided embodiments, the one or more image objects is one or more non-cell particles. In certain embodiments of any of the provided embodiments, prior to the analyzing the output composition is enriched for the one or more non-cell particles.

In some embodiments of any of the provided embodiments: the output composition does not comprise an agent for detecting the particles. In some embodiments of any of the provided embodiments, the agent is or comprises a detectable moiety or is capable of producing a detectable signal or the analyzing does not comprise adding an agent for detecting the particles to the output composition, wherein the agent is or comprises a detectable moiety or is capable of producing a detectable signal. In particular embodiments of any of the provided embodiments, an image object is a non-cell particle if: (i) the image object comprises a circularity of at or at least 0.5, 0.6, 0.7, 0.8, or 0.9; (ii) the image object comprises a diameter of between 5 µm and 10 inclusive; and/or (iii) the image object comprises an area of between 25 µm$^2$ and 50 µm$^2$; (iv) the image object comprises a fluorescent signal; and/or (v) the image object comprises a florescent intensity (FI). In some embodiments of any of the provided embodiments, the image object comprises a fluorescent signal above a background signal in a control sample. In some embodiments of any of the provided embodiments, the FI is greater than a background signal in a control sample. In some embodiments of any of the provided embodiments, the fluorescent intensity is the mean fluorescent intensity. In some embodiments of any of the provided embodiments, an image object is detected as being a non-cell particle if the image object comprises a fluorescent signal and (i) the image object comprises a circularity of at least 0.4, (ii) the image object comprises a diameter of between 1 µm and 20 inclusive, and/or (iii) the image object comprises an area of less than 130 µm$^2$. In some embodiments of any of the provided embodiments, an image object is detected as being a non-cell particle if the image object comprises a fluorescent signal above a background signal in a control sample. In some embodiments of any of the provided embodiments, an image object is detected as a non-cell particle if (i) the image object comprises a circularity of at or at least 0.4, at or at least 0.5, at or at least 0.6, at or at least 0.7, at or at least 0.8, or at or at least 0.9, (ii) the image object comprises a diameter of between 3 µm and 15 inclusive, and/or (iii) the image object comprises an area of between 0.5 µm$^2$ and 50 µm$^2$. In some embodiments of any of the provided embodiments, (A) an image object is detected as a singlet non-cell particle if the image object comprises a fluorescent signal, and (1) the image object comprises a circularity of at or at least 0.7, (ii) the image object comprises a diameter of between 1 µm and 7.5 inclusive, and/or (iii) the image object comprises an area of less than 65 µm$^2$; and (B) an image object is detected as a doublet non-cell particle if the image object comprises a fluorescent signal and (i) the image object comprises a circularity of between or between about 0.4 and 0.6, (ii) the image object comprises a diameter of between 2 µm and 15 µm, inclusive, and/or (iii) the image object comprises an area of less than 130 µm$^2$. In some embodiments of any of the provided embodiments, an image object is detected as a singlet non-cell particle if the image object comprises a fluorescent signal above a background signal in a control sample. In some embodiments of any of the provided embodiments, an image object is detected as a doublet non-cell particle if the image object comprises a fluorescent signal above a background signal in a control sample. In some embodiments of any of the provided embodiments, (A) an image object is detected as a singlet non-cell particle if the image object comprises a fluorescent signal, and (1) the image object comprises a circularity of between or between about 0.7 and 1.0, (ii) the image object comprises a diameter of between or about between 1 µm and 5 µm, inclusive, and/or (iii) the image object comprises an area of less than 65 µm$^2$; and (B) an image object is detected as a doublet non-cell particle if the image object comprises a fluorescent signal, and (i) the image object comprises a circularity of between or between about 0.4 and 0.6, (ii) the image object comprises a diameter of between 2 µm and 10 µm, inclusive, and/or (iii) the image object comprises an area of less than 130 µm$^2$. In some embodiments of any of the provided embodiments, an image object is detected as a singlet non-cell particle if the image object comprises a fluorescent signal above a background signal in a control sample. In some embodiments of any of the provided embodiments, an image object is detected as a doublet non-cell particle if the image object comprises a fluorescent signal above a background signal in a control sample.

In some embodiments of any of the provided embodiments, the control sample is a composition produced by incubating a cell composition comprising the one or more cells but not comprising, or not likely comprising, the one or more non-cell particles, wherein the incubating is under conditions to induce lysis of cells to produce an output composition. In some embodiments of any of the provided embodiments, the control sample is a composition produced by incubating a cell composition comprising the one or more cells but not comprising the one or more non-cell particles, wherein the incubating is under conditions to induce lysis of cells to produce an output composition. In some embodiments of any of the provided embodiments, the analyzing further comprises enumerating the number of non-cell particles determined to be present in the sample.

In certain embodiments of any of the provided embodiments, the one or more non-cell particles are autofluorescent. In certain embodiments of any of the provided embodiments, the analyzing is carried out using a computer-implemented image analysis. In certain embodiments of any of the provided embodiments, the analyzing is carried out using a computer-implemented image analysis, or one or more steps of the method is carried out by a machine, a robot, and/or a computer-implemented algorithm. In particular embodiments of any of the provided embodiments, one or more steps of the method is high-throughput and/or automated. In particular embodiments of any of the provided embodiments, one or more steps of the method is carried out by a machine, a robot and/or a computer-implemented algorithm.

In certain embodiments of any of the provided embodiments: the input composition comprises or is suspected of comprising one or more of the non-cell particles bound to the surface of one or more cells in the input composition; the input composition comprises or is suspected of comprising residual particles following removal of one or more non-cell particles from a cell composition; the input composition is derived from a composition containing one or more cells bound to one or more of the non-cell particles; and/or the input composition is derived from a composition containing one or more cells bound to one or more of the non-cell particles is further processed by removing one or more of the non-cell particles. In certain embodiments of any of the provided embodiments, the input composition is derived from a cell composition, said cell composition comprising one or more cells and one or more of the non-cell particles in which said one or more non-cells particles comprises a biomolecule capable of binding to a macromolecule on the surface of the one or more cells.

In particular embodiments of any of the provided embodiments, the input composition is produced by a method comprising: (1) mixing one or more cells with one or more of the non-cell particles; and (2) removing one or more of the non-cell particles from the cells. In particular embodiments of any of the provided embodiments, the input composition comprises or is likely to comprise or may comprise residual non-cell particles, said residual non-cell particles present following removal of one or more non-cell particles from a cell composition. In some embodiments of any of the provided embodiments, the one or more of the particles comprise one or more biomolecule is capable of binding to a macromolecule on the surface of a cell. In some embodiments of any of the provided embodiments, the one or more of the non-cell particles comprise one or more biomolecule is capable of binding to a macromolecule on the surface of a cell.

In certain embodiments of any of the provided embodiments, the incubating under conditions to induce lysis of cells comprises incubating the sample with a detergent and/or a bleach. In certain embodiments of any of the provided embodiments, the incubating under conditions to induce lysis of cells comprises incubating the sample with a solution comprising a bleach. In some embodiments of any of the provided embodiments, the bleach is a chlorine-based bleach. In particular embodiments of any of the provided embodiments, the detergent is one or more of Triton X-100, Triton X-114, NP-40, Brij-35, Brij-58, Tween 20, Tween 80, digitonin, octyl glucoside, octyl thioglucoside, sodium dodecyl sulfate (SDS), 3-[(3-cholamidopropyl)dimethylammonio]-1-propanesulfonate (CHAPS) and CHAPSO. In particular embodiments of any of the provided embodiments, the solution comprising bleach further comprises a detergent. In some embodiments of any of the provided embodiments, the detergent is one or more of Triton X-100, Triton X-114, NP-40, Brij-35, Brij-58, Tween 20, Tween 80, digitonin, octyl glucoside, octyl thioglucoside, sodium dodecyl sulfate (SDS), 3-[(3-cholamidopropyl)dimethylammonio]-1-propanesulfonate (CHAPS) and CHAPSO. In particular embodiments of any of the provided embodiments, the bleach is a chlorine-based bleach. In certain embodiments of any of the provided embodiments, the sample is incubated with bleach at a concentration of about 0.1%, 0.2%, 0.3%, 0.4%, 0.5%, 1%, 1.5%, 2%, 3%, 4%, 5%, 6%, 7% or 8% (v/v) bleach, or a range defined by any two of the foregoing values. In particular embodiments of any of the provided embodiments, the incubating under conditions to induce lysis of cells comprises incubating the sample with bleach wherein the sample is incubated with bleach at a concentration of about 0.1%, 0.2%, 0.3%, 0.4%, 0.5%, 1%, 1.5%, 2%, 3%, 4%, 5%, 6%, 7% or 8% (v/v) bleach, or a range defined by any two of the foregoing values. In particular embodiments of any of the provided embodiments: the incubating is carried out for at least or at least about 30 seconds, 1 minute, 2 minutes, 3 minutes, 4 minutes, 5 minutes, 10 minutes, 20 minutes or 30 minutes; or the incubating is carried out from or from about 30 seconds to 30 minutes, 1 minute to 20 minutes, 1 minute to 10 minutes or 1 minute to 5 minutes. In some embodiments of any of the provided embodiments, the particles are enriched by exposing the output composition to a magnetic field. In certain embodiments of any of the provided embodiments, the enriching reduces or removes cell debris from the output composition.

In particular embodiments of any of the provided embodiments, prior to the analyzing or capturing the method further comprises rinsing or washing the output composition. In particular embodiments of any of the provided embodiments, prior to the analyzing the method further comprises rinsing or washing the output composition with a wash solution. In some embodiments of any of the provided embodiments, the wash solution comprises a detergent. In particular embodiments of any of the provided embodiments, prior to the capturing, the method further comprises rinsing or washing the output composition with a wash solution. In some embodiments of any of the provided embodiments, the wash solution comprises a detergent. In particular embodiments of any of the provided embodiments, rinsing or washing the output composition comprises pelleting the one or more non-cell particles and removing a volume or reducing a volume of the output composition. In particular embodiments of any of the provided embodiments, the detergent is one or more of Triton X-100, Triton X-114, NP-40, Brij-35, Brij-58, Tween 20, Tween 80, digitonin, octyl glucoside, octyl thioglucoside, sodium dodecyl sulfate (SDS), 3-[(3-cholamidopropyl)dimethylammonio]-1-propanesulfonate (CHAPS) and CHAPSO. In particular embodiments of any of the provided embodiments, the detergent is or comprises Tween 20. In some embodiments of any of the provided embodiments, the concentration of cells in the sample is at least or at least about $2\times10^5$ cells/mL, at least or at least about $5\times10^5$ cells/mL, at least or at least about $1\times10^6$ cells/mL, at least or at least about $5\times10^6$ cells/mL, at least or at least about $1\times10^7$ cells/mL, at least or at least about $5\times10^7$ cells/mL, at least or at least about $1\times10^8$ cells/mL or at least or at least about $5\times10^7$ cells/mL. In particular embodiments of any of the provided embodiments, the volume of the output composition volume of the output composition is at or about or is at least at or about 10 µL, 25 µL, 50 µL, 75 µL, 100 µL, 125 µL, 200 µL, 250 µL, 500 µL, 750 µL, 1 mL, 2 mL, 3 mL, 4 mL, 5 mL, 6 mL, 7 mL, 8 mL, 9 mL, or 10 mL, or a range defined by any two of the foregoing values. In some embodiments of any of the provided embodiments, the concentration of cells in the sample of at least a portion of the input composition is at least about $2\times10^5$ cells/mL, at least or at least about $5\times10^5$ cells/mL, at least or at least about $1\times10^6$ cells/mL, at least or at least about $5\times10^6$ cells/mL, at least or at least about $1\times10^7$ cells/mL, at least or at least about $5\times10^7$ cells/mL, at least or at least about $1\times10^8$ cells/mL or at least or at least about $5\times10^7$ cells/mL. In particular embodiments of any of the provided embodiments, the volume of the output composition volume of the output composition is at or about or is at least at or about 10 µL, 25 µL, 50 µL, 75 µL, 100 µL, 125 µL, 200 µL, 250 µL, 500 µL, 750 µL, 1 mL, 2 mL, 3 mL, 4 mL, 5 mL, 6 mL, 7 mL, 8 mL, 9 mL, or 10 mL, or a range defined by any two of the foregoing values. In particular embodiments of any of the provided embodiments, the volume of the output composition or a portion thereof is at or about or is at least at or about 50 µL, 60 µL, 70 µL, 75 µL, 100 µL, 125 µL, 200 µL, 250 µL, 500 µL, 750 µL, 1 mL, 2 mL, 3 mL, 4 mL, 5 mL, 6 mL, 7 mL, 8 mL, 9 mL, or 10 mL, or a range defined by any two of the foregoing values. In particular embodiments of any of the provided embodiments, the volume of the output composition is at least at or about or is at or about 70 µL.

In particular embodiments of any of the provided embodiments, prior to the analyzing the method comprises one or more of mixing the output composition under conditions to agitate the one or more cell particles in the sample. In particular embodiments of any of the provided embodiments, during the one or more steps of the method the output composition is processed under conditions to reduce sample retention on a surface during the processing.

In certain embodiments of any of the provided embodiments, the one or more non-cell particles comprise beads. In certain embodiments of any of the provided embodiments, the one or more non-cell particles is or comprises beads. In particular embodiments of any of the provided embodiments, the one or more of the non-cell particles has a diameter of greater than 0.001 µm, greater than 0.01 µm, greater than 0.1 µm, greater than 1.0 µm, greater than 10 µm, greater than 50 µm, greater than 100 µm or greater than 1000 µm. In some embodiments of any of the provided embodiments, the one or more of the non-cell particles is a bead. In particular embodiments of any of the provided embodiments, one or more of the non-cell particles has a diameter of 1.0 µm to 500 µm, 1.0 µm to 150 µm, 1.0 µm to 30 µm, 1.0 µm to 10 µm or 1.0 µm to 5.0 µm. In some embodiments of any of the provided embodiments, the one or more of the non-cell particles is a bead. In particular embodiments of any of the provided embodiments, one or more of the non-cell particles has a diameter of 1.0 µm to 10 µm or 1.0 µm to 5.0 µm. In some embodiments of any of the provided embodiments, the one or more of the non-cell particles is a bead. In some embodiments of any of the provided embodiments, the one or more of the non-cell particles has a diameter that is substantially the same as the average diameter of a cell in the cell composition or is within 5-fold, 4-fold, 3-fold, 2-fold or 1.5-fold greater or less than the average diameter of a cell in the cell composition. In some embodiments of any of the provided embodiments, the one or more of the non-cell particles is a bead.

In certain embodiments of any of the provided embodiments, the one or more particles has a diameter that is or is about the same size as a lymphocyte or an antigen presenting cell. In some embodiments of any of the provided embodiments, the one or more of the non-cell particles is a bead. In particular embodiments of any of the provided embodiments, the one or more non-cell particles has a diameter of greater than or greater than about 3.5 µm but no more than about 9 µm or no more than about 8 µm or no more than about 7 µm or no more than about 6 µm or no more than about 5 µm. In some embodiments of any of the provided embodiments, the one or more of the non-cell particles is a bead. In particular embodiments of any of the provided embodiments, the one or more non-cell particles has a diameter, or an average diameter, of greater than or greater than about 3.5 µm but no more than about 9 µm or no more than about 8 µm or no more than about 7 µm or no more than about 6 µm or no more than about 5 µm. In some embodiments of any of the provided embodiments, the one or more of the non-cell particles is a bead. In particular embodiments of any of the provided embodiments, the one or more non-cell particles comprises a diameter of or about 4.5 µm. In some embodiments of any of the provided embodiments, the one or more of the non-cell particles is a bead. In particular embodiments of any of the provided embodiments, the one or more non-cell particles comprises a diameter, or an average diameter, of or about 4.5 µm. In certain embodiments of any of the provided embodiments, one or more of the non-cell particles comprise a core. In some embodiments of any of the provided embodiments, the one or more of the non-cell particles is a bead. In certain embodiments of any of the provided embodiments, one or more of the non-cell particles comprise a magnetic core, a paramagnetic core or a superparamagnetic core.

In particular embodiments of any of the provided embodiments, one or more of the non-cell particles comprise a superparamagnetic core. In some embodiments of any of the provided embodiments, the core is selected from among metal oxides, ferrites, metals, hematite, metal alloys, and combinations thereof. In particular embodiments of any of the provided embodiments, the one or more non-cell particles is inert. In some embodiments of any of the provided embodiments, the one or more of the non-cell particles is a bead. In particular embodiments of any of the provided embodiments, the one or more non-cell particles is or comprises a polystyrene surface. In some embodiments of any of the provided embodiments, the one or more non-cell particles is a bead. In some embodiments of any of the provided embodiments, the one or more non-cell particles is or comprises a polystyrene surface, and comprises a magnetic or superparamagnetic core. In certain embodiments of any of the provided embodiments, the polystyrene surface is autofluorescent. In certain embodiments of any of the provided embodiments, the one or more biomolecule comprise antibodies and/or are present on the surface of the one or more non-cell particles. In some embodiments of any of the provided embodiments, the one or more non-cell particles is a bead. In certain embodiments of any of the provided embodiments, the one or more biomolecule is present on, or attached to, the surface of the one or more non-cell particles. In some embodiments of any of the provided embodiments, the one or more non-cell particles is a bead. In some embodiments of any of the provided embodiments, the one or more biomolecule is a selection agent capable of selecting one or more cells in a sample or is a stimulatory agent or agents capable of stimulating one or more cells in the sample. In some embodiments of any of the provided embodiments, the one or more biomolecule is a stimulatory agent or agents capable of stimulating one or more cells in the sample. In some embodiments of any of the provided embodiments, the one or more biomolecule is an antibody or an antigen-binding fragment thereof.

In particular embodiments of any of the provided embodiments, the stimulatory agent or agents is capable of activating one or more intracellular signaling domains of one or more components of a TCR complex and/or one or more intracellular signaling domains of one or more costimulatory molecules. In particular embodiments of any of the provided embodiments, the stimulatory agent or agents comprises a primary agent that specifically binds to a member of a TCR complex and a secondary agent that specifically binds to a T cell costimulatory molecule.

In certain embodiments of any of the provided embodiments, the primary agent specifically binds to CD3 and/or the costimulatory molecule is selected from the group consisting of CD28, CD137 (4-1-BB), OX40, or ICOS. In certain embodiments of any of the provided embodiments, the primary agent specifically binds to CD3 and/or the costimulatory molecule is selected from the group consisting of CD28, CD137 (4-1-BB), OX40, and ICOS. In particular embodiments of any of the provided embodiments, the primary agent is or comprises anti-CD3 and the secondary agent is or comprises anti-CD28. In particular embodiments of any of the provided embodiments, the primary agent is or comprises an anti-CD3 antibody or antigen-binding fragment thereof and the secondary agent is or comprises an anti-CD28 antibody or antigen-binding fragment thereof. In some embodiments of any of the provided embodiments, the one or more cells has a diameter of between or about between 10 µm and 30 µm. In particular embodiments of any of the provided embodiments, the one or more cells is an animal cell or the cell composition comprises animal cells. In particular embodiments of any of the provided embodiments, the one or more cells is a human cell or the cell composition comprises human cells.

In certain embodiments of any of the provided embodiments, the one or more cells is a stem cell or the cell composition comprises stem cells. In some embodiments of any of the provided embodiments, the stem cell is an induced pluripotent stem cell (iPSC). In particular embodiments of any of the provided embodiments, the one or more cell is an immune cell or the cell composition comprises immune cells. In particular embodiments of any of the provided embodiments, the immune cell is a T cell, B cell, macrophage, neutrophil, natural killer (NK) cell or dendritic cell. In certain embodiments of any of the provided embodiments, the one or more cells have been mixed with one or more of the non-cell particles, wherein the non-cell particle comprises a stimulating agent or agents to effect stimulation and/or activation of a cell in the cell composition prior to the incubating.

In particular embodiments of any of the provided embodiments, the cell is a T cell and the stimulating agent or agents is an anti-CD3 antibody and/or anti-CD28 antibody or an antigen-binding fragment thereof. In particular embodiments of any of the provided embodiments, the cell is a T cell and the one or more non-cell particles comprises or is attached to a stimulating agent or agents, wherein said stimulating agent or agents is an anti-CD3 antibody or antigen-binding fragment thereof and/or anti-CD28 antibody or an antigen-binding fragment thereof. In some embodiments of any of the provided embodiments, the one or more cells have been mixed with one or more of the non-cell particles, wherein the non-cell particle comprises one or more affinity reagent to effect selection, isolation or enrichment of a cell from a cell composition prior to the incubating. In some embodiments of any of the provided embodiments, the one or more of the non-cell particles comprises one or more affinity reagent to effect selection, isolation or enrichment of a cell from a cell composition prior to the incubating. In particular embodiments of any of the provided embodiments, the affinity reagent comprises an antibody or antigen-binding fragment thereof that specifically binds to a cell surface protein on the one or more cells. In particular embodiments of any of the provided embodiments, the cell surface protein is selected from among CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1), CD62L (L-selectin), CD29/CD49d (VLA-4), a Notch ligand, Delta-like 1/4, Jagged 1/2, CCR1, CCR2, CCR3, CCR4, CCR5, CCR7, and CXCR3.

In certain embodiments of any of the provided embodiments, the incubating is performed at a temperature that is about 15° C. to 30° C., 18° C. to 28° C. or 20° C. to 25° C. In particular embodiments of any of the provided embodiments, the incubating is performed at a temperature that is about 23° C.

Provided herein is an article of manufacture, comprising a container comprising a solution comprising bleach and/or detergent for effecting cell lysis; packaging material; and a label or package insert comprising instructions for detecting the presence or absence of particles by any of the methods or embodiments provided herein.

Also provided herein is an article of manufacture, comprising: a container comprising a solution comprising bleach and/or detergent for effecting cell lysis; packaging material; and a label or package insert comprising instructions for detecting the presence or absence of particles in a cell composition; wherein the instructions specify the steps of: a) incubating a sample comprising at least a portion of an input composition or a sample derived from the input composition, said input composition comprising one or more cells and one or more non-cell particles, wherein the incubating is with the solution under conditions to induce lysis of cells to produce an output composition; b) analyzing the output composition or a portion thereof by fluorescence imaging to determine the presence or absence of particles in the sample.

In certain embodiments of any of the provided embodiments, the instructions specify the analyzing the output composition by fluorescence imaging comprises obtaining fluorescent micrographs of the output composition or a portion thereof. In some embodiments of any of the provided embodiments, the instructions specify the analyzing the output composition by fluorescence imaging comprises obtaining fluorescent micrographs of the output composition or a portion thereof and determining the fluorescent intensity of image objects from the fluorescent micrographs. In some embodiments of any of the provided embodiments, the fluorescent intensity is the mean fluorescent intensity. In some embodiments of any of the provided embodiments, the instructions specify further obtaining brightfield micrographs of the output composition or a portion thereof. In certain embodiments of any of the provided embodiments, the instructions specify the analyzing the output composition further comprises determining the size, area, and/or circularity of image objects from the fluorescent micrographs or brightfield micrographs.

Provided herein is an article of manufacture, comprising: a container comprising a solution comprising bleach and/or detergent for effecting cell lysis; packaging material; and a label or package insert comprising instructions for detecting the presence or absence of particles in a cell composition; wherein the instructions specify the steps of: (i) illuminating an output composition or a portion thereof with one or more light sources to generate an illuminated sample, wherein at least one light source is capable of exciting fluorescent molecules; (ii) capturing one or more images of the illuminated sample, wherein at least one image is a fluorescent image; (iii) analyzing the presence or absence of image objects from the one or more images for one or more parameters selected from size, area, fluorescent intensity (FI), brightfield intensity, and/or circularity; wherein the output composition is produced by incubating a sample comprising at least a portion of an input composition or a sample derived from the input composition, said input composition comprising one or more cells and one or more non-cell particles, wherein the incubating is with the solution under conditions to induce lysis of cells to produce an output composition. In some embodiments of any of the provided embodiments, the fluorescent intensity is the mean fluorescent intensity. In some embodiments of any of the provided embodiments, the brightfield intensity is the mean brightfield intensity.

Provided herein is an article of manufacture, comprising: a container comprising a solution comprising bleach and/or detergent for effecting cell lysis; packaging material; and a label or package insert comprising instructions for detecting the presence or absence of particles in a cell composition; wherein the instructions specify the steps of: a) incubating a sample comprising at least a portion of an input composition or a sample derived from the input composition, said input composition comprising one or more cells and one or more non-cell particles, wherein the incubating is with the solution under conditions to induce lysis of cells to produce an output composition; b) optically analyzing the output composition or portion thereof to assess the presence or absence of one or more parameters of one or more image objects, wherein the one or more parameters is selected from size, area, fluorescent intensity (FI), brightfield intensity, and/or particle circularity. In some embodiments of any of the provided embodiments, the fluorescent intensity is the mean fluorescent intensity. In some embodiments of any of the provided embodiments, the brightfield intensity is the mean brightfield intensity.

In particular embodiments of any of the provided embodiments, the output composition does not comprise an agent for detecting the particles. In particular embodiments of any of the provided embodiments, the agent is or comprises a detectable moiety or is capable of producing a detectable; signal or the instructions specify the analyzing does not comprise adding an agent for detecting the particles to the output composition. In particular embodiments of any of the provided embodiments, the agent is or comprises a detectable moiety or is capable of producing a detectable signal.

In some embodiments of any of the provided embodiments, the instructions further specify prior to the analyzing, the output composition is enriched for the one or more non-cell particles. In particular embodiments of any of the provided embodiments, the instructions further specify prior to the illuminating the output composition is enriched for the one or more non-cell particles. In certain embodiments of any of the provided embodiments, the instructions further specify prior to the analyzing the output composition is enriched for the one or more non-cell particles.

In certain embodiments of any of the provided embodiments, the one or more non-cell particles is autofluorescent; and/or the instructions further specify the steps are carried out on a sample or composition that may contain non-cell particles that are autofluorescent. In certain embodiments of any of the provided embodiments, the instructions specify the steps for detecting the presence or absence of a non-cell particle an image object is a non-cell particle if: (i) the image object comprises a circularity of at or at least 0.5, 0.6, 0.7, 0.8, or 0.9; (ii) the image object comprises a diameter of between 5 μm and 10 inclusive; and/or (iii) the image object comprises an area of between 25 $\mu m^2$ and 50 $\mu m^2$; (iv) the image object comprises a fluorescent signal; and/or (v) the image object comprises a florescent intensity (FI). In certain embodiments of any of the provided embodiments, the fluorescent intensity is a mean fluorescent intensity (MFI). In some embodiments of any of the provided embodiments, the image object comprises a fluorescent signal above a background signal in a control sample. In some embodiments of any of the provided embodiments, the FI is greater than a background signal in a control sample.

Provided herein is an article of manufacture, comprising a container comprising a solution comprising bleach and/or detergent for effecting cell lysis, packaging material, and a label or package insert comprising instructions for detecting the presence or absence of particles in a cell composition; wherein the instructions specify carrying out the steps of any of the methods provided herein.

In any of the articles of manufacture provided herein, the article of manufacture also contains instructions carrying out a method for detecting the presence or absence of non-cell particles in any of the above embodiments.

BRIEF DESCRIPTION OF THE DRAWINGS

FIG. 4A shows differences in bead counts between Method 1 ("automatic fluorescent method") and Method 2 ("manual method"), described in Example 1.J, plotted against the mean bead counts of the two methods. FIG. 4B shows the error-in-variable regression between bead counts by Method 1 and Method 2.

FIG. 5A shows plots of the residual values (expected count subtracted from actual count) at each target concentration (expected counts) for the automatic and manual methods, respectively. The dotted horizontal lines indicate the residual value of 0. FIG. 5B shows the error-in-variable regression between automatic and manual bead counts.

DETAILED DESCRIPTION

Figure 1:
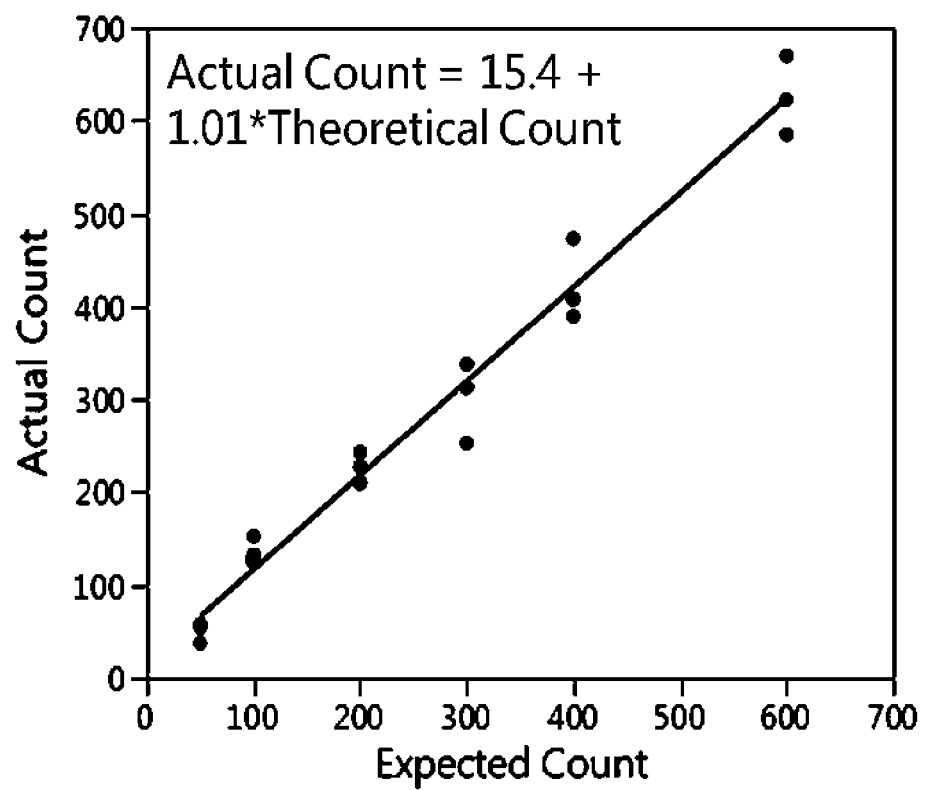
FIG. 1 shows a plot of measured bead concentrations (actual count) at target concentrations (expected count). The equation at the top left describes the linear relationship between the actual count and the expected count.

Provided herein are methods for determining or assessing the presence or absence, including the number or concentration, of particles in a sample of a cell composition. In some embodiments, the methods involve incubating a sample of a cell composition that contains or potentially contains non-cell particles (hereinafter also called "particles," e.g., bead particles) associated with the cells, wherein the one or more incubations are performed under one or more conditions sufficient to induce lysis of cells in the sample. In some embodiments, the sample comprises at least a portion of a cell composition of interest or a sample derived from a cell composition of interest. In some embodiments, the one or more incubations result in an output composition that is then measured or assessed for the presence or absence of particles (e.g., bead particles). Thus, in the provided methods, an output composition (e.g., sample after the lysis methods) is assessed to determine the presence or absence (e.g. number or concentration) of particles in the sampled cell composition. In some cases, the provided methods permit the efficient and reliable detection of particles (e.g., bead particles) in a sample of an output composition, thereby improving the accuracy and reliability of visualizing, detecting and/or identifying the particles (e.g., bead particles) in a sample. In some embodiments, the number of particles present in the output composition can be determined using any of a number of methods for visualizing, detecting, identifying and/or quantitating particles.

In some embodiments, the visualization, detection, identification and/or quantitation is performed in an automated manner, e.g., using automated and/or high-throughput methods. In some aspects, automated, high-throughput image capture coupled with automated image analysis permits enumeration of particles in multiple samples in a cost- and time-efficient manner and with accurate, precise and consistent results, while minimizing experimenter bias. In some aspects, the provided embodiments are used for particles (e.g., bead particles) that have particular properties such as autofluorescence and consistent shape and size. In some aspects, one or more non-cell particles is autofluorescent.

In some aspects, consistent shape and size of the particles (e.g., bead particles) permit the automated detection and enumeration of beads. In some aspects, the provided embodiments offer an advantage of a rapid, accurate and consistent method to determine the number of particles in a sample, without the requirement of staining or manual detection and enumeration of the particles.

In some embodiments, particles (e.g. microspheres or bead particles) and cells can exhibit physical similarities, such as similarities in size, shape and/or color. In some cases, due to the physical similarities between the particles (e.g. microspheres or bead particles) and cells, it can be difficult to assess the particle content in a cell composition comprising cells mixed with particles. In some aspects, in order to detect or determine the presence, absence, number, and/or concentration of particles (e.g. microspheres or bead particles) in a cell composition, methods must be performed to distinguish the cells in the sample from the particles desired to be enumerated.

In some cases, some methods of enumerating particles, such as magnetic bead particles, in a sample include visualization of particles (e.g., bead particles) in a non-lysed cell sample under a microscope. This is possible due to a brown or reddish color of the particles, or other physical characteristic, that differentiates the particles from cells in the sample. When using some particles, such as certain bead particles described herein, this visualization is not possible because at least some of the particles look substantially the same as cells in the sample and so enumerating the particles is not feasible. Further, in a concentrated cell/particle sample, such as provided herein, the number of cells is far greater than the number of particles, further making accurate enumeration of the particles difficult. In addition, manual visualization and enumeration of particles can be time-consuming and inconsistent due to experimenter variation.

In some cases, methods of visualizing or detecting particles requires removing intact cells from the sample, such as methods that lyse or damage the cells in solution, thereby only leaving intact particles to make it easier to visualize individual particles in the sample. In some aspects, the provided embodiments permit lysis of the cells using a variety of lysis methods, for example by chemical (e.g. detergent or bleach), thermal and physical lysis methods. In some aspects, the use of a bleach in a lysis method allows for better lysis of cells, such that intact cells and/or large cellular debris do not obscure the non-cell particles and make accurate enumeration of the particles difficult. In some aspects, the use of a detergent in a lysis method allows for better lysis of cells and separation of cellular debris, such that cellular debris does not stick or clump together. Specifically, the use of a detergent, such as a tween-based detergent, as opposed to a protein (e.g. BSA)-based detergent provides effective separation of cells and cellular debris. Cells or cellular debris that sticks or clumps together can autofluoresce, obscure non-cell particles, and/or be similar in size to non-cell particles, further making accurate enumeration of the particles difficult.

In some aspects, the provided embodiments are suitable for enumerating particles (e.g., bead particles) that are not damaged or destroyed by the lysis method, e.g., the surface or coat of the particle is intact after exposure to the lysis step. In some aspects, the method of lysis does not interfere with or affect the integrity of the particles (e.g. bead particles). In some aspects, one or more further incubations can be performed that can include a further lysis and/or rinse, to remove cell debris, thereby rendering any remaining cell debris sufficiently different from the particles (e.g., bead particles) to allow for accurate particle visualization and enumeration. In some aspects, one or more further incubations can be performed that can include a further lysis and/or one or more rinses or washes, to remove cell debris, thereby rendering any remaining cell debris sufficiently different from the particles (e.g., bead particles) to allow for accurate particle visualization and enumeration.

One or more other features of the method also offer advantages over existing methods for enumerating particles (e.g. bead particles) in a cell composition sample. In some aspects, the methods can include at least two rinsing or washing steps of the particles, to further remove cellular debris from the particles. In some aspects, the methods include mixing or agitating, e.g. vortexing, the cell composition and/or output composition. Mixing or agitating, e.g. vortexing, the cell composition improves the lysis of cells. In some cases, mixing or agitating, e.g. vortexing, the output composition after lysis of cells ensures that more particles in a sample tube are captured in the sample solution and enumerated and/or that such particles are not clumped together so that individual particles can be more easily enumerated. In some aspects, the sample to be analyzed comprises at least 50 µL of volume, allowing for enumeration of particles by automated methods. Manual methods of particle enumeration (e.g., by hemocytometer) are limited in the sample volume that can be analyzed. In some aspects, the sample to be analyzed by an automated method comprises more volume than a sample to be analyzed by a manual method can comprise, ensuring more accurate enumeration of particles. In some aspects, the methods involve the use of low-retention pipette tips. Low-retention pipette tips retain fewer particles than standard pipette tips, thereby increasing the accuracy of residual particle enumeration in the output composition.

The presently disclosed methods can preserve the integrity of the particle, rendering the particles compatible for quantification using alternative techniques, such as light microscopy, antibody-based methods, or other methods.

Thus, provided herein are methods for assessing the presence or absence of particles in a cell composition comprising a mixture of particles and cells. Such methods allow for the lysis of cells and removal of cellular material in the sample while maintaining consistent particle enumeration in an automated and/or high-throughput manner. The methods also provide accurate, precise and consistent measurements and do not require staining or manual counting. Therefore, the particles obtained by the provided methods are suitable for measurement to assess the absence or presence of particles in a sampled cell composition. Also provided are articles of manufacture and kits for use in the methods, e.g., containing the reagents or components for performing the provided methods.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Methods and Reagents for Assessing Particles, e.g., Bead Particles

Provided herein are methods for assessing particles, such as bead particles. In some embodiments, the provided methods are used to detect the presence or absence of particles, such as bead particles, in a sample that is known to contain or that potentially contains one or more non-cell particles (e.g., bead particles). In some embodiments, the sample comprises at least a portion of a cell composition or is derived from a cell composition. In aspects of the method, the sample is a sample that contains a plurality of cells, which plurality of cells is or may be associated with one or more particles (e.g., bead particles). In some embodiments, the provided methods can be used to enumerate or determine the presence, absence, number and/or concentration of the particles (e.g., bead particles) in the sample.

In some embodiments, the sample comprises at least a portion of a cell composition or is derived from a cell composition. In some aspects, the cell compositions can contain cells, e.g., T cells, engineered to express a recombinant receptor for administration to a subject for adoptive cell therapy. In some aspects, the engineered cells can be generated using process that involves incubation of cells with bead particles for stimulation and/or for enrichment of particular cells in the cell composition. In some aspects, the process also involves removal of bead particles after incubation. In some aspects, the provided automated methods can be used to enumerate residual beads that are present in the cell composition, such as beads that remain in the sample after removal steps. In some cases, the provided method can be used to determine the efficiency of removal of the bead particles and to reduce adverse or toxic effects that can result from incomplete removal of the bead particles.

In some embodiments, the provided methods involve incubating or contacting a sample containing a plurality of cells under one or more conditions sufficient to induce lysis of cells in the sample, and determining, via an automated system, the presence, absence, number and/or concentration of particles (e.g., bead particles) in the sample after lysis of the cells has occurred. In some embodiments, lysis is or includes chemical (e.g., bleach or detergent), thermal lysis, physical lysis, osmotic lysis (e.g. due to the presence of a hypotonic solution) and/or plasmolysis (e.g. due to the presence of a hypertonic solution). A sample after lysis by the methods described herein, such as by one or more incubation with detergent or bleach, is also referred to as an "output composition." As a non-limiting example, the output composition can be a lysed cell composition resulting from one or more incubations of a sample, wherein the one or more incubations of the sample are under a condition sufficient to induce lysis of one or more cells in a sample, thereby producing the output composition. As another non-limiting example, the output composition can be a composition resulting from one or more incubations of a sample to produce a lysed cell composition, wherein the lysed cell composition is further subjected to one or more incubations to reduce or remove the cell debris, thereby producing the output composition. In some embodiments, the one or more lysis and/or incubation conditions are such that they do not or do not substantially interfere with or remove the presence of intact particles in the sample, so that in general, the presence, absence, number and/or concentration of particles in the output composition is the same or substantially the same as the presence, absence number, and/or concentration of particles in the sample prior to the lysis.

In some embodiments, the methods for detecting the presence or absence of particles in a cell composition include the steps of a) incubating a sample comprising at least a portion of an input composition or a sample derived from the input composition, said input composition comprising one or more cells and one or more non-cell particles (e.g. such as a cell composition described in Section III.B below), wherein the incubating is under conditions to induce lysis of cells to produce an output composition; and b) analyzing the output composition or a portion thereof by fluorescence imaging to determine the presence or absence of particles in the sample.

In some embodiments, the methods for detecting the presence or absence of particles include analyzing an output composition or a portion thereof by fluorescence imaging to determine the presence or absence of particles in the sample, wherein the output composition is produced by incubating a sample comprising at least a portion of an input composition or a sample derived from the input composition, said input composition comprising cells and one or more non-cell particles, under conditions to induce lysis of cells.

In some embodiments, the methods can include the steps of a) incubating a sample comprising at least a portion of an input composition or a sample derived from the input composition, said input composition comprising cells and one or more non-cell particles (e.g., those described in Section III.A below), wherein the incubating is under conditions to induce lysis of cells to produce an output composition; and b) analyzing the output composition, e.g., enriched output composition, by fluorescence imaging to determine the presence or absence of particles in the sample.

In some embodiments, the methods can include the steps of a) performing one or more incubations to produce an output composition, where the one or more incubations in step a) comprises i) incubating a sample of an input composition that does or potentially does contain particles (e.g. such as a cell composition described in Section III.B below) under one or more conditions sufficient to induce lysis (e.g., bleach or detergent) of one or more cells in the sample, thereby producing the output composition; and b) determining the presence, absence, number and/or concentration of non-cell particles (e.g., bead particles) in the output composition, e.g., enriched output composition.

In particular aspects of any of the described methods, the fluorescence imaging is capable of detecting autofluorescence of the one or more non-cell particles (e.g. beads) in the sample.

In some embodiments, the analyzing step and/or determining the presence, absence, number and/or concentration of particles can be carried out by automated and/or high-throughput methods, e.g., automated, high-throughput image capture and/or automated image analysis.

In some embodiments, the methods involve (i) illuminating an output composition or a portion thereof with one or more light sources to generate an illuminated sample, wherein at least one light source is capable of exciting or causing a fluorescence signal of the particles, e.g. an autofluorescence; (ii) capturing one or more images of the illuminated sample, wherein at least one image is a fluorescent image; (iii) analyzing the presence or absence of image objects from the one or more images for one or more parameters selected from size, area, fluorescent intensity (FI), brightfield intensity, and/or circularity, wherein the output composition is produced by incubating a sample comprising at least a portion of an input composition or a sample derived from the input composition, said input composition comprising one or more cells and one or more non-cell particles under conditions to induce lysis of the cells. In some embodiments, the light source is capable of exciting or excites an autofluorescence. In some embodiments, the fluorescent intensity is the mean fluorescent intensity. In some embodiments, the brightfield intensity is the mean brightfield intensity.

In some embodiments, the methods involve a) incubating a sample comprising at least a portion of an input composition or a sample derived from the input composition, said input composition comprising one or more cells and one or more non-cell particles, wherein the incubating is under conditions to induce lysis of cells to produce an output composition; and b) optically analyzing the output composition or portion thereof to assess the presence or absence of one or more parameters of one or more image objects, wherein the one or more parameters is selected from size, area, fluorescent intensity (FI), brightfield intensity, and/or particle circularity. In some embodiments, the fluorescent intensity is the mean fluorescent intensity. In some embodiments, the brightfield intensity is the mean brightfield intensity.

In some embodiments, the methods involve optically analyzing an output composition or portion thereof to assess the presence or absence of one or more parameters of one or more image objects, said one or more parameters selected from size, area, fluorescent intensity (FI), brightfield intensity, and/or particle circularity, wherein the output composition is produced by incubating a sample comprising at least a portion of an input composition or a sample derived from the input composition under conditions to induce lysis of cells, said input composition comprising cells and one or more non-cell particles. In some embodiments, the fluorescent intensity is the mean fluorescent intensity. In some embodiments, the brightfield intensity is the mean brightfield intensity.

In particular embodiments, fluorescence detection is based on autofluorescent properties of the particles, e.g. bead particles. In some embodiments, the output composition does not comprise an agent for detecting the particles, optionally does not comprise an agent for detecting the particles that is or comprises a detectable moiety or is capable of producing a detectable signal. In some embodiments of the provided methods, the analyzing does not comprise adding an agent for detecting the particles to the output composition, optionally does not comprise an agent for detecting the particles that is or comprises a detectable moiety or is capable of producing a detectable signal.

In some embodiments, lysis, such as in the presence of a detergent and/or a bleach, can result in a lysed composition that includes cell debris and/or that may be sticky, for example, due to the release of lipids, DNA and other molecules from the cell. Thus, in some embodiments, after incubating or contacting cells with a detergent and/or a bleach, the method generally includes at least one further step in order to remove cell debris or other components that may impact the ability to detect the number, presence of concentration of the particles (e.g., bead particles). In some embodiments, after incubating or contacting cells with a detergent and/or a bleach, the method generally includes at least one further step of enriching for the non-cell particles (e.g., bead particles), such as by exposure of the output composition to a magnetic field. In some embodiments, the further step can include sonication, rinsing or washing of the output composition (which can be a lysed cell composition), an incubation or further incubation of the lysed cell composition with solutions or buffers for washing or other method to reduce, lessen or remove cell debris in the output composition, resulting in an enriched output composition. In some embodiments, the method for generating the output composition, e.g., enriched output composition, does not damage the non-cell particles (e.g., bead particles). In some embodiments, prior to the analyzing or illuminating the output composition is enriched for the one or more non-cell particles.

In some embodiments, determining the number of particles (e.g., bead particles) in the output composition can be by any method in which such particles can be visualized, detected, and/or presence, absence, number or concentration determined. In some embodiments, such methods can include microscopy (e.g., fluorescent and/or bright field microscopy), flow cytometry and fluorescence-activated cell sorting (FACS), and other methods. In some embodiments, the determining the presence, absence, number and/or concentration of particles can be carried out by automated and/or high-throughput methods, e.g., automated, high-throughput image capture and/or automated image analysis. In some embodiments, the ability to assess, detect or identify particles (e.g., bead particles) by automated and/or high-throughput methods can result in more reliable results and, in some cases, can be performed in a fraction of the time or labor compared to manual visualization methods, such as using a hemocytometer.

In some embodiments, the provided lysis methods are selectively lyse the cells, and thereby do not result in adverse structural or physical damage to the non-cell particles (e.g. microspheres or bead particles). In some cases, the provided methods permit detection or identification of the affinity reagents associated with the particles (e.g., bead particles) using affinity-based reagents, such as antibody reagents or other binding agents.

In some embodiments, the method is performed on a sample of cells that is derived from a cell composition or that contains at least a portion of a cell composition. In some embodiments, the cell composition is one that has undergone at least one processing step in the presence of at least one particle (e.g., bead particles) that produces or potentially produces a composition comprising at least one cell specifically associated or that had been associated with at least one particle (e.g. bead particle), such as a composition in which at least one particle (e.g. bead particle) is still present or potentially present (e.g. a residual particle after a removal step) in a composition with the at least one cell. In some embodiments, the processing step is or includes one or more of enrichment, separation, selection, isolation, stimulation, activation and/or expansion of the at least one cell in a population or sample of cells.

In some embodiments, the cell composition is one that is intended for use in cell therapy, in which the cell therapy composition contains or potentially contains one or more particles (e.g., bead particles) associated with or that had been associated with one or more cells in the composition of cells or contained in the same composition as the one or more cells, such as a composition in which at least one particle (e.g. bead particle) is still present or potentially present (e.g. a residual particle after a removal step) in a composition with the at least one cell. As an example, adoptive cell therapy employing immune cells (e.g. T cells) is used a treatment for cancer and other diseases or conditions. In some cases, immune cells (e.g. T cells) to be used in adoptive transfer are obtained from blood or tissue sites and are subsequently engineered with a recombinant receptor that binds to a target antigen associated with the disease or condition prior to reintroduction to the subject. In general, such methods involve selection, isolation, activation and/or expansion of cells using various types of affinity-based particle reagents. For example, use of antibodies against CD3, a multimeric protein complex that serves as a T cell co-receptor to activate T cells, is commonly used in ex vivo T cell proliferation methods for the expansion of T cells along with a costimulatory signal, such as by using anti-CD28 antibodies. When anti-CD3 and anti-CD28 antibodies are immobilized on a surface (e.g. a bead particle), they simultaneously deliver a proliferative signal and a costimulatory signal in order to increase T cell proliferation. See Li et al. (2010) J Transl Med., 8:104.

Exemplary methods of processing cells in the presence of particles, such as microspheres or bead particles, that may result or potentially result in a cells associated with, or being present in the same composition with, at least one such particle is described in Section III. For certain methods, particles (e.g. magnetic bead particles) are used as a surface for immobilization of affinity reagents (e.g. antibodies) for use in various methods, such as in detection, selection, enrichment, isolation, activation and/or stimulation of cells. For example, particles coated with such antibodies have been used as reagents to expand functional T cells for subsequent delivery to a subject, such as by infusion.

In some embodiments, particles used for T cell stimulation and expansion are usually uniformly round-shaped and have about the same size as cells. These particle characteristics can result in some disadvantages in the production and safety of cell adoptive therapy such as T cell adoptive therapy. For example, due to the similarity in size between particles and the cells they have been incubated with, complete removal of the particles from a cell composition comprising a cell population and particles is a significant challenge. The actual number of residual particles left behind in a cell composition after a particle removal process is an important factor to consider when assessing the risk for toxic effects of stimulatory particles that are left behind in a cell composition subsequently used for administration in an individual during cell adoptive therapy. In some embodiments, the process of removing particles (e.g., bead particles, including magnetic beads) after separation from cells can result in a cell composition that may contain residual particles. For example, in some cases where magnetic beads are employed for selection, enrichment and/or stimulation of cells (e.g. T cells), removal of particles often requires the passing of the cell/bead solution over a magnet. This process can greatly reduce the quantity of particles remaining with the cells (e.g. T-cells), but may not completely eliminate the particles. An incomplete bead removal can result in some particles being infused into patients, which can cause toxic effects. Thus, it is necessary to be able to accurately, reliably and/or efficiently determine or assess the presence or absence of non-cell particles (e.g., bead particles) present in such cell compositions intended for cell therapy.

In some embodiments, after determining the presence, absence, number, and/or concentration of particles in the sample, the method further includes calculating or determining the number of cells present in the cell composition. Thus, in some aspects, the method can provide information about the presence, absence, number, and/or concentration of particles in a larger cell composition from which the sample has been obtained or derived. In some cases, the method can be used to determine or assess if a cell composition is suitable for administration as a cell therapy, such as in connection with adoptive cell therapy methods.

In some embodiments, the provided methods result in a high consistent and/or repeatable enumeration of particles (e.g. microspheres or bead particles) in the sample after the lysis methods (e.g., output composition, such as an enriched output composition).

In some embodiments, the provided methods result in particles that preserve the integrity of the particles, sufficient for detection and analysis of the particles by fluorescence imaging. In some embodiments, the number of intact particles that do not have a degraded or damaged surface (e.g. intact microsphere or bead particles) in the sample after the lysis methods (e.g., such as in the output composition, such as an enriched output composition) is greater than or greater than about 10%, 15%, 20%, 25%, 30%, 35%, 40%, 45%, 50%, 55%, 60%, 65%, 70%, 75%, 80% or 85% as compared to or of the total number of particles and/or expected number of particles in the sample prior to lysis. In some embodiments, the number of intact particles that do not have a degraded or damaged surface (e.g. intact microsphere or bead particles) in the sample after the lysis methods (e.g., in the output composition such as enriched output composition) is greater than or greater than about 85%, 86%, 87%, 88%, 89%, 90%, 91%, 92%, 93%, 94%, 95%, 96%, 97%, 98%, 99% or 100% as compared to the total number of particles and/or expected number of particles in the sample prior to lysis. In some embodiments, the number of particles (e.g. microspheres or bead particles) is generally from or from about 40% to 100%, such as generally greater than 40%, 45%, 50%, 55%, 60%, 65% or 70%.

In some embodiments, by virtue of the automated and/or high-throughput analysis of the fluorescent imaging, the provided methods result in an improved or greater accuracy in detecting or assessing particles in a sample or cell composition compared to other methods. In some embodiments, since the instant methods result in lysis of substantially all or all of the cells in the sample, and optionally removal of residual cell debris, there is a reduced or lower likelihood of a false positive where a cell is counted or identified as a particle. In some embodiments, since the method does not damage the surface of the particle (e.g. microsphere or bead particle) and the size, area and/or circularity of the images of the particles can be detected using computer-implemented image analysis in a consistent and accurate manner. In some embodiments, since the method does not damage the surface of the particle (e.g. microsphere or bead particle), methods for detecting or identifying a particle can be reliably employed, thereby reducing or minimizing false negatives.

In some embodiments, the precision of the detection or enumeration (e.g., closeness of agreement between a series of measurements) is generally greater than or greater than about 10%, 15%, 20%, 25%, 30%, 35%, 40%, 45%, 50%, 55%, 60%, 65%, 70%, 75%, 80% or 85%. In some embodiments, the precision of the detection or enumeration (e.g., closeness of agreement between a series of measurements) is generally greater than or greater than about 85%, 86%, 87%, 88%, 89%, 90%, 91%, 92%, 93%, 94%, 95%, 96%, 97%, 98%, 99% or 100%. In some embodiments, the precision of detecting or enumerating particles (e.g., microspheres or bead particles) in a cell sample or cell composition is generally from or from about 95% to 100%, such as generally greater than 97%, 98% or 99%. In some embodiments, the precision of detection or enumeration of particles (e.g., microspheres or bead particles) from a cell sample or cell composition by the provided methods is improved (e.g. by at least 1.2-fold, 1.3-fold, 1.4-fold, 1.5-fold, 1.6-fold, 1.7-fold, 1.8-fold, 2-fold, 3-fold, 4-fold, 5-fold or more) compared to other methods that are known or available for enumerating particles, such as other methods involving manual detection and enumeration. In some embodiments, the coefficient of variation (CV) is reduced (e.g. by at least 1.2-fold, 1.3-fold, 1.4-fold, 1.5-fold, 1.6-fold, 1.7-fold, 1.8-fold, 2-fold, 3-fold, 4-fold, 5-fold or more) compared to other methods that are known or available for enumerating particles, such as other methods involving manual detection and enumeration.

In some embodiments, the accuracy of the detection or enumeration (e.g., closeness of agreement between true value/accepted reference value and the value determined by the method) is generally greater than or greater than about 10%, 15%, 20%, 25%, 30%, 35%, 40%, 45%, 50%, 55%, 60%, 65%, 70%, 75%, 80% or 85%. In some embodiments, the accuracy of the detection or enumeration (e.g., closeness of agreement between true value/accepted reference value and the value determined by the method) is generally greater than or greater than about 85%, 86%, 87%, 88%, 89%, 90%, 91%, 92%, 93%, 94%, 95%, 96%, 97%, 98%, 99% or 100%. In some embodiments, the percent recovery (% recovery) is generally greater than or greater than about 85%, 86%, 87%, 88%, 89%, 90%, 91%, 92%, 93%, 94%, 95%, 96%, 97%, 98%, 99% or 100%. In some embodiments, the accuracy of detecting or enumerating particles (e.g., microspheres or bead particles) in a cell sample or cell composition or percent recovery is generally from or from about 95% to 100%, such as generally greater than 97%, 98% or 99%. In some embodiments, the accuracy of detection or enumeration of particles (e.g., microspheres or bead particles) from a cell sample or cell composition by the provided methods is improved (e.g. by at least 1.2-fold, 1.3-fold, 1.4-fold, 1.5-fold, 1.6-fold, 1.7-fold, 1.8-fold, 2-fold, 3-fold, 4-fold, 5-fold or more) compared to other methods that are known or available for enumerating particles, such as other methods involving manual detection and enumeration.

In some embodiments, the specificity of the detection or enumeration (e.g., ability to specifically separate the particular analyte in the presence of other components) is generally greater than or greater than about 10%, 15%, 20%, 25%, 30%, 35%, 40%, 45%, 50%, 55%, 60%, 65%, 70%, 75%, 80% or 85%. In some embodiments, the specificity of the detection or enumeration (e.g., ability to specifically separate the particular analyte in the presence of other components) is generally greater than or greater than about 85%, 86%, 87%, 88%, 89%, 90%, 91%, 92%, 93%, 94%, 95%, 96%, 97%, 98%, 99% or 100%. In some embodiments, the specificity of detecting or enumerating particles (e.g., microspheres or bead particles) in a cell sample or cell composition is generally from or from about 95% to 100%, such as generally greater than 97%, 98% or 99%. In some embodiments, the specificity of detection or enumeration of particles (e.g., microspheres or bead particles) from a cell sample or cell composition by the provided methods is improved (e.g. by at least 1.2-fold, 1.3-fold, 1.4-fold, 1.5-fold, 1.6-fold, 1.7-fold, 1.8-fold, 2-fold, 3-fold, 4-fold, 5-fold or more) compared to other methods that are known or available for enumerating particles, such as other methods involving manual detection and enumeration.

In some embodiments, the linearity of the detection or enumeration (e.g., ability (within a given range) to obtain test results that are directly proportional to the concentration (amount) of the analyte in the sample), such as represented by the coefficient of determination ($R^2$), is generally greater than or greater than about 0.10, 0.15, 0.20, 0.25, 0.30, 0.35, 0.40, 0.45, 0.50, 0.55, 0.60, 0.65, 0.70, 0.75, 0.80 or 0.85. In some embodiments, the linearity of the detection or enumeration (e.g., ability (within a given range) to obtain test results that are directly proportional to the concentration (amount) of the analyte in the sample), such as represented by the coefficient of determination ($R^2$), is generally greater than or greater than about 0.85, 0.86, 0.87, 0.88, 0.89, 0.90, 0.91, 0.92, 0.93, 0.94, 0.95, 0.96, 0.97, 0.98, 0.99 or 1.00. In some embodiments, the linearity of detecting or enumerating particles (e.g., microspheres or bead particles) in a cell sample or cell composition, such as represented by the coefficient of determination ($R^2$), is generally from or from about 0.95 to 1.00, such as generally greater than 0.97, 0.98, 0.99 or 1.00. In some embodiments, the linearity of detection or enumeration of particles (e.g., microspheres or bead particles) from a cell sample or cell composition by the provided methods is improved (e.g. by at least 1.2-fold, 1.3-fold, 1.4-fold, 1.5-fold, 1.6-fold, 1.7-fold, 1.8-fold, 2-fold, 3-fold, 4-fold, 5-fold or more) compared to other methods that are known or available for enumerating particles, such as other methods involving manual detection and enumeration.

In some embodiments, the range of the method, the limit of range of detection and/or enumeration with acceptable precision and accuracy, is within the required limit to detect the number of residual beads in a therapeutic composition, e.g., therapeutic compositions containing engineered cells for adoptive cell therapy. In some embodiments, the range of detection or enumeration of particles (e.g., microspheres or bead particles) from a cell sample or cell composition by the provided methods is improved (e.g. by at least 1.2-fold, 1.3-fold, 1.4-fold, 1.5-fold, 1.6-fold, 1.7-fold, 1.8-fold, 2-fold, 3-fold, 4-fold, 5-fold or more) compared to other methods that are known or available for enumerating particles, such as other methods involving manual detection and enumeration.

In some embodiments, the methods can be used to assess or determine if the presence, absence, number, and/or concentration of particles (e.g. microsphere or bead particles) in a cell composition is within an acceptable level or range, such as is or is not greater than a desired threshold or predetermined value. For example, for certain applications or uses of a cell sample or composition, it may not be desirable to have a large number of particles (e.g. microsphere or particle) present in a cell composition. In some cases, even where biodegradable non-cell particles are employed, it may be necessary to monitor or determine the extent, number or presence of such particles in cell compositions used for cell therapies for administration to subjects for treating a disease or condition. In some aspects, a cell composition for cell therapy typically contains no more than 100 particles (e.g. microspheres or bead particles) per $3 \times 10^6$ cells, no more than 75 particles per $3 \times 10^6$ cells, or no more than 50 particles per $3 \times 10^6$ cells. In some aspects, a cell composition for cell therapy typically contains no more than 200 particles per mL, no more than 250 particles per mL, no more than 300 particles per mL, no more than 400 particles per mL, no more than 500 particles per mL, no more than 1000 particles per mL, no more than 2000 particles per mL, or no more than 2500 particles per mL.

In some embodiments, if the method determines that the presence, absence, number, and/or concentration of particles (e.g. microspheres or bead particles) is greater than a predetermined or threshold value for a particular application of a cell composition, the cell composition can be further processed to remove or reduce the number of particles (e.g. microspheres or bead particles) and/or is not released or not validated for use in such application (e.g. cell therapy). In some embodiments, if the method determines that the presence, absence, number, and/or concentration of non-cell particles (e.g. microspheres or bead particles) meets or is below a threshold or predetermined value for a particular application, the cell composition can be released or validated for use in such application (e.g. cell therapy). In some embodiments, for example where it is suspected or known that a certain amount of particles are lost during the sample processing, the threshold can be set to account for a known or suspected bead loss.

II. Incubation(s), Cell Lysis and Detection of Particles

The methods provided herein for detecting the presence, absence, number, amount, or concentration of particles, such as bead particles, include one or more steps of lysing cells in a sample that is known to contain or that potentially contains one or more particles (e.g., bead particles). In some embodiments, the sample contains at least a portion of an input composition, and/or is derived from an input composition, that contains or potentially contains particles, e.g., bead particles.

In particular embodiments, the methods provided herein contain one or more steps for determining the presence, absence, number, and/or concentration of particles (e.g. microspheres or bead particles) present in a cell composition, for example, by determining the presence, absence, number, and/or concentration of particles in an output composition, e.g., a composition resulting from lysis of the cells in a sample comprising at least a portion of an input composition or a sample derived from the input composition, generated by incubating the sample containing at least a portion of the input composition or derived from the input composition under conditions for lysis of cells. In some aspects, the output composition is further enriched or processed, e.g., resulting in an enriched output composition. In certain embodiments, the methods provided herein include one or more steps of lysing cells in a sample from a composition, e.g., an input composition, that is known to contain or that potentially contains one or more particles (e.g., bead particles) and detecting the presence, absence, number, amount, or concentration of particles in the sample.

A. Incubation and Cell Lysis

In some embodiments, the sample used in the methods provided herein comprises at least a portion of an input composition or is derived from the input composition, where the input composition comprises one or more cells and one or more non-cell particles. In some embodiments, the incubation of the sample is under conditions to induce lysis of cells in the sample to produce an output composition. In some embodiments, an output composition is a composition, e.g., a sample and/or an input composition, that have been subject to lysis and/or have been incubated under conditions to induce lysis of cells in the sample and/or input composition. In some embodiments, the output composition can include compositions that have been further subject to enrichment, separation and/or washing, resulting in an enriched output composition. In some aspects, the output composition, e.g., enriched output composition, is analyzed using the methods provided herein.

In some embodiments, the cells in a sample comprising at least a portion of an input composition that does or potentially does contain particles (e.g. such as a cell composition described herein in Section III) or a sample derived from such an input composition are mixed, incubated, contacted or re-suspended to expose the cells to a condition (e.g., one or more condition) sufficient to induce lysis of cells in the sample. In some embodiments, the sample of cells is provided as a suspension of cells and the method includes subjecting the suspension of cells to one or more conditions that induces lysis of the cells. In some embodiments, the lysis method is one that maintains the particles intact, such that the particles can be easily identified, visualized and/or detected, such as using automated or high-throughput analysis. In some embodiments, the lysis method does not destroy the coating or the surface of the particles, which, in some cases, can facilitate their detection. In some aspects, known methods for cell lysis can be used. In some embodiments, prior to the analyzing the output composition is enriched for the one or more non-cell particles. In some embodiments, the output composition does not comprise an agent for detecting the particles, optionally wherein the agent is or comprises a detectable moiety or is capable of producing a detectable; signal or the analyzing does not comprise adding an agent for detecting the particles to the output composition, optionally wherein the agent is or comprises a detectable moiety or is capable of producing a detectable signal.

In some embodiments, the sample (or the input composition from which the sample is derived from) contains cells, such as engineered cells. In some embodiments, the concentration of the cells in the sample or the input composition is at least or at least about $2\times10^5$ cells/mL, at least or at least about $5\times10^5$ cells/mL, at least or at least about $1\times10^6$ cells/mL, at least or at least about $5\times10^6$ cells/mL, at least or at least about $1\times10^7$ cells/mL, at least or at least about $5\times10^7$ cells/mL, at least or at least about $1\times10^8$ cells/mL or at least or at least about $5\times10^7$ cells/mL. In some aspects, the condition for lysis is sufficient to induce lysis of all or substantially all of the cells in the sample containing any of the described cell concentrations.

1. Lysis with Bleach and/or Detergent

In some embodiments, the sample is incubated in a condition sufficient to induce lysis of the cells in a sample, where the condition comprises incubation with agents capable of lysing cells, e.g., one or more bleach and/or one or more surfactant, e.g., a detergent. In some aspects, the sample is incubated with a solution containing one or more bleach. In some embodiments, the sample is incubated with a solution containing one or more surfactant, e.g., a detergent. In some embodiments, the sample is incubated with a solution containing both bleach and a surfactant, e.g., a detergent. In some embodiments, the cells in the sample are lysed using known cell lysis methods using bleach and/or detergent.

In some embodiments, the sample is incubated with one or more surfactant(s), such as a detergent. In some embodiments, the one or more detergent is selected from Triton X-100, Triton X-114, NP-40, Brij-35, Brij-58, Tween 20, Tween 80, digitonin, octyl glucoside, octyl thioglucoside, sodium dodecyl sulfate (SDS), 3-[(3-cholamidopropyl)dimethylammonio]-1-propanesulfonate (CHAPS) and CHAPSO. In some embodiments, the detergent is one or more of polyethylene glycol p-(1,1,3,3-tetramethylbutyl)-phenyl ether (Triton X-100®), polyoxyethylene-polyoxypropylene block copolymer (Pluronic® F-68), poly(ethylene glycol)-block-poly(propylene glycol)-block-poly(ethylene glycol) (Pluronic® L-121), poloxamer 407 (Pluronic® F127), and/or polyethylene glycol dodecyl ether (Brij® 35).

In some embodiments, the sample is incubated with a detergent at a final concentration (w/v) of at least or at least about 0.001%, 0.002%, 0.005%, 0.01%, 0.02%, 0.03%, 0.035%, 0.04%, 0.045%, 0.05%, 0.055%, 0.06%, 0.065%, 0.07%, 0.075%, 0.08%, 0.085%, 0.09%, 0.095%, 0.10%, 0.2%, 0.3%, 0.35%, 0.4%, 0.45%, 0.5%, 0.55%, 0.6%, 0.65%, 0.7%, 0.75%, 0.8%, 0.85%, 0.9%, 0.95% or 1% or more. In some embodiments, the sample is incubated with a detergent at a final concentration (w/v) of between 0.001% and 0.5%, between 0.001% and 0.1%, between 0.001% and 0.075%, between 0.001% and 0.05%, between 0.001% and 0.01%, between 0.001% and 0.005%, between 0.005% and 0.5%, between 0.005% and 0.1%, between 0.005% and 0.075%, between 0.005% and 0.05%, between 0.005% and 0.01%, between 0.01% and 0.5%, between 0.01% and 0.1%, between 0.01% and 0.075%, between 0.01% and 0.05%, between 0.05% and 0.01%, between 0.05% and 0.075% and between 0.075% and 0.5%, each inclusive.

In some embodiments, the sample is incubated with one or more bleach. In some embodiments, the bleach is a chlorine-based bleach, a peroxide-based bleach, a reducing bleach and/or a miscellaneous bleach. In some embodiments, the bleach is a peroxide-based bleach. In some embodiments, the bleach is one or more of hydrogen peroxide, organic peroxide, sodium percarbonate or sodium borate. In some embodiments, the bleach is a reducing bleach, such as sodium dithionite or sodium hydrosulfite.

In some embodiments, the bleach is a chlorine-based bleach. In some aspects, the bleach is a chlorine-based bleach containing a hypochlorite, chlorine or chlorine dioxide. In some embodiments, the bleach is sodium hypochlorite. In some embodiments, the sample is incubated with bleach at a final bleach concentration of about 0.1%, 0.2%, 0.3%, 0.4%, 0.5%, 1%, 1.5%, 2%, 3%, 4%, 5%, 6%, 7% or 8% (v/v) bleach, or a range defined by any two of the foregoing values.

In some embodiments, the sample is incubated with a concentrated or undiluted bleach solution, at a volume of approximately 1/10, 1/8, 1/5, 1/4, 1/3 or 1/2, or a range defined by any of the foregoing values, of the volume of the sample. In some embodiments, the volume of the concentrated or undiluted bleach solution to the volume of the sample is between at or about 10:1 and at or about 10:1 (or greater than about 1:10 and less than about 10:1), between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 10:1; 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, 1:5 or 1:10. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, the incubation is performed from about 30 seconds to about 5 hours, such as 1 minute to 30 minutes, 1 minute to 15 minutes or 1 minute to 5 minutes. In some embodiments, the incubation is performed for at least or at least about 1 minute, 2 minutes, 3 minutes, 4 minutes, 5 minutes, 6 minutes, 7 minutes, 8 minutes, 9 minutes, 10 minutes, 15 minutes or 30 minutes. In some embodiments, during the incubation, the cells can be mixed or gently shaken in order to mix the cells with the agents for lysis, e.g., a bleach and/or detergent.

In some embodiments, the incubation is performed at a temperature of from or from about 0° C. to 50° C. In some embodiments, the temperature can be at or with a particular range associated with refrigerated temperatures (e.g., 2° C. to 8° C.), ambient temperature (e.g., 16° C. to 25° C.) or physiological temperature (e.g., 35° C. to 38° C.). In some embodiments, the temperature is about 15° C. to about 30° C., about 18° C. to about 28° C. or about 20° C. to about 25° C. In some embodiments, the temperature is at least or at least about or is or is about 4° C.±2° C., 23° C.±0.2° C., 25° C.±2° C., or 37° C.±2° C.

2. Osmotic Lysis

In some cases, the one or more condition induces osmotic lysis of the cells in the sample. In some embodiments, the method involves mixing, incubating, exposing, contacting or resuspending a sample of cells that does or that may contain one or more particles (e.g., microsphere or bead particles) with one or more conditions that create a change in osmotic pressure in the cells, resulting in an osmotic imbalance that causes water to transfer into the cell so that a substantial number of cells in the sample lyse. A variety of known techniques can be used to create a change in an osmotic pressure in the cells. In some aspects of the method, a sample of cells is provided and osmotic lysis is induced by mixing, incubating, exposing, contacting or resuspending the cells with a hypotonic solution to result in a hypotonic cell suspension having an osmolarity that is reduced to less than the osmolarity of the inside of the cells, such as generally to less than the physiological osmolarity. Typically, the physiological osmolarity to which cells are exposed is approximately 290 mOsm/L to 300 mOsm/L. In general, cell culture media and other cell buffers are designed to maintain an osmolarity of between 270 mOsm/L and 330 mOsm/L, such as to mimic the physiological osmolarity of serum. Thus, changes in the osmolarity caused by exposure of cells to the hypotonic solution, and the resulting changes in osmotic pressure in the cells mixed, contacted or suspended in the solution, can lead to lysis of substantially all of the cells in the composition, while leaving the particles (e.g., bead particles) intact.

In some aspects, cells typically lyse due to osmotic pressure if the total volume of the cell swells to approximately 150% of the original volume, although the percentage may vary somewhat with cell type and other factors (Kinosita et al. (1977) Proc. Natl. Acad. Sci., 74:1923-7). In some embodiments, the method includes subjecting a sample, such as a suspension of cells having a standard osmolarity (e.g. 270 mOsm/L-330 mOsm/L), to a hypotonic solution such that the osmolarity of the hypotonic cell suspension is sufficiently reduced so that the total volume expansion of the cells in the suspension exceeds about 150% of the volume of the cell when under standard physiological osmolarity conditions. In general, the particular osmolarity of the hypotonic solution to effect a reduction in osmolarity of the resulting hypotonic cell suspension can be empirically determined, such as based on the particular cell type or cell types in the sample, the density of cells in the sample, the volume of the resulting hypotonic cell suspension, the length of incubation, the temperature of incubation and other known factors. In some cases, cells with small nuclear to cell diameter ratios can lyse at osmolarities that are much higher than cells where the nuclear to cell diameter is greater (published PCT Appl. No. WO1999054439).

In some embodiments, a hypotonic solution is added to a solution-free cell sample, for example as obtained after centrifugation of the cells into a pellet and discarding of the supernatant or after collection of the cells on a filtration membrane. Alternatively, the solution-free cell sample (or a fraction thereof) may be added to the hypotonic solution. In both cases above, the hypotonic solution can be mixed with the cells to result in a hypotonic cell suspension in which the cells are suspended under hypotonic conditions. In some embodiments, a predetermined volume of a hypotonic solution is added to cells suspended in a standard physiological osmolarity solution (e.g. standard cell media or buffer) to form the hypotonic cell suspension. In such embodiments, a predetermined volume of the hypotonic solution having a predetermined osmolarity is dispensed into, such as mixed with, the cell suspension (or, equivalently, the cell suspension may be dispensed or mixed into the hypotonic solution) in order to result in a hypotonic cell suspension with a reduced osmolarity compared to the osmolarity of the initial suspension of cells.

In some embodiments, the hypotonic solution is any liquid that can be mixed with cells or a cell suspension to effect a change in osmotic pressure in the cells. In some embodiments, the hypotonic solution can include, but is not limited to, a solution containing one or more solutes in a solvent or mixture of solvents, generally pure solvents (e.g. distilled deionized water), or mixtures of essentially pure solvents, so long as the hypotonic solution has an osmolarity that is different from an osmolarity of the cells to which it is contacted, mixed or suspended. In general, the hypotonic solution is one that, when contacted, mixed or suspended with cells or a cell suspension, can result in a suspension of cells that has a solution osmolarity that is hypotonic.

In some embodiments, the hypotonic solution is solute-free. In some embodiments, the hypotonic solution can be sterile water for injection, such as distilled/deionized water (DDI water).

In some embodiments, the hypotonic solution is or can be formulated in the presence of solutes. In some embodiments, the concentration of solute present in the hypotonic solution is such that the osmolarity of the hypotonic solution or the osmolarity of the resulting hypotonic cell suspension is less than the physiological osmolarity, such as generally less than 270 mOsm/L. In some cases, the solute or solutes that can be present include any that may be present in standard reagents, such as in standard cell media or buffers. In some embodiments, the solutes in a hypotonic solution can include salts such as sodium chloride (NaCl), ammonium chloride, potassium chloride, sodium citrate, and sugars such as dextrose, glucose and sucrose. In some embodiments, a solute can be one that is provided or present in standard media, such as phosphate buffered saline (PBS), Iscove's Modified Dulbecco's Medium (IMDM) and other standard cell culture media, which generally have a standard physiological osmolarity of about 300 mOsm/L. In some embodiments, a hypotonic solution can be obtained by dilution of a solute-providing media or buffer, such as PBS or IMDM, with a solvent. In some cases, distilled/deionized water can be used as the solvent for such dilution. The pH of the hypotonic solution can be adjusted as needed, generally to a pH that does not damage the particles described herein.

In some embodiments, the hypotonic solution comprises a solute concentration of between or between about 0 mM and 140 mM. In some embodiments, the hypotonic solution comprises a solute concentration of less than or about less than 140 mM, 100 mM, 50 mM or 10 mM. In some embodiments herein, the hypotonic solution comprises a weight percent (% w/v) of solute of between about 0% and about 0.8% or between about 0% and about 0.5%. In some embodiments, the hypotonic solution comprises a weight percent (% w/v) of solute of less than about 0.8%, less than about 0.7%, less than about 0.6%, less than about 0.5%, less than about 0.4%, less than about 0.3% or less than about 0.2%. In some of the embodiments, the hypotonic solution or resulting hypotonic cell suspension has an osmolarity between about 0 mOsm/L and about 270 mOsm/L, such as between about 0 mOsm/L and 200 mOsm/L, 0 mOsm/L and 140 mOsm/L, 0 mOsm/L and 100 mOsm/L, 10 mOsm/L and 200 mOsm/L, 10 mOsm/L and 140 mOsm/L, 10 mOsm/L and 100 mOsm/L, 50 mOsm/L and 200 mOsm/L, 50 mOsm/L and 140 mOsm/L, 50 mOsm/L and 100 mOsm/L, 100 mOsm/L and 200 mOsm/L, 100 mOsm/L and 140 mOsm/L or 140 mOsm/L and 200 mOsm/L. In some embodiments, the hypotonic solution or resulting hypotonic cell suspension has an osmolarity of less than about 270 mOsm/L, less than about 250 mOsm/L, less than about 225 mOsm/L, less than about 200 mOsm/L, less than about 175 mOsm/L, less than about 150 mOsm/L, less than about 140 mOsm/L, less than about 125 mOsm/L, less than about 100 mOsm/L, less than about 75 mOsm/L, less than about 50 mOsm/L, less than about 25 mOsm/L or less than about 10 mOsm/L.

In some embodiments, additionally or alternatively, the one or more conditions to induce lysis of cells in the sample includes any that induces or causes plasmolysis of cells in the sample and/or involves mixing, incubating, exposing, contacting or resuspending cells or a cell suspension with a hypertonic solution. In some embodiments, a hypertonic solution can cause the lysis (death by internal bursting) of one or many cells by causing the cells to swell from abnormal osmosis and putting too much pressure upon the internal walls of the cell that then bursts, and thus dies. In some embodiments, the method includes subjecting a sample, such as a sample comprising a suspension of cells, to a hypertonic solution that has an osmolarity that is greater or higher than the inside of the cells or cell suspension prior to incubation or contacting with the hypertonic solution, thereby causing the cell to swell from abnormal osmosis leading to internal bursting. In general, the particular osmolarity of the hypertonic solution to effect an increase in osmolarity of the resulting hypertonic cell suspension can be empirically determined, such as based on the osmolarity of the cell or cell suspension prior to contacting or incubation with the hypertonic solution (e.g. if the cell or cell suspension has been previously incubated or contacted with a hypotonic solution), the particular cell type or cell types in the sample, the density of cells in the sample, the volume of the resulting hypertonic cell suspension, the length of incubation, the temperature of incubation and other known factors.

In some embodiments, the one or more incubations to induce cell lysis (e.g. by incubation with a hypotonic solution) results in a lysed cell composition that can be directly assessed as the output composition for measuring, determining or assessing the presence, absence, number or concentration of particles in the sample. In other embodiments, the lysed cell composition is further processed by one or more additional incubations, enrichment, separation, rinses and/or washes prior to obtaining an enriched output composition for measuring, determining or assessing the presence, absence, number or concentration of particles in the sample. For example, in some cases, incubation of a cell sample with a hypotonic solution can lead to a hypotonic lysis that can generate cellular debris that can interfere with the determination of the presence or number of particles in the lysed cell composition. In some embodiments, after the hypotonic lysis, the method can further include reducing, lessening or removing cell debris in the hypotonic lysed cell composition prior to determining the presence, absence, number, and/or concentration of particles (e.g., bead particles or microspheres) present in the lysed sample.

In some embodiments, incubation with a hypertonic solution can be employed in the context of the provided method to reduce, lessen or remove cell debris in a lysed cell composition described herein. In some embodiments, reducing or removing cell debris in a lysed cell composition can include: i) contacting or incubating the lysed cell composition, such as a hypotonic lysed cell composition, in the presence of a hypertonic solution, thereby producing the output composition; and ii) enriching, rinsing or washing the output composition, wherein cell debris is reduced or removed (e.g., to obtain an enriched output composition). In some embodiments, provided herein is a method of detecting the presence or absence of particles (e.g., bead particles or microspheres) in a sample of a cell composition, such as to enumerate particles in the cell composition, that includes: i) incubating or contacting a sample with a hypotonic solution, thereby producing a lysed cell composition (or hypotonic lysed cell composition); ii) incubating or contacting the lysed cell composition with a hypertonic solution, thereby producing an output composition; iii) optionally enriching, rinsing or washing the output composition (e.g., to obtain an enriched output composition); and determining the presence, absence, number, and/or concentration of particles (e.g. microspheres or bead particles) in the output composition or the washed/rinsed output composition.

In some embodiments, a hypertonic solution is added to a solution-free cell sample, for example as obtained after centrifugation of the cells into a pellet and discarding of the supernatant or after collection of the cells on a filtration membrane. Alternatively, the solution-free cell sample (or a fraction thereof) may be added to the hypertonic solution. In both cases above, the hypertonic solution can be mixed with the cells to result in a hypertonic cell suspension in which the cells are suspended under hypertonic conditions. In some embodiments, the hypertonic cell suspension is formed by adding a predetermined volume of a hypertonic solution to a cell suspension having a lower osmolarity, such as cells suspended in a standard physiological osmolarity solution (e.g. standard cell media or buffer) or cells suspended in a hypotonic solution (e.g. a hypotonic lysed cell composition). In such embodiments, a predetermined volume of the hypertonic solution having a predetermined osmolarity is dispensed into, such as mixed with, the cell suspension (or, equivalently, the cell suspension may be dispensed or mixed into the hypertonic solution) in order to result in a hypertonic cell suspension with an increased or greater osmolarity compared to the osmolarity of the initial suspension of cells prior to the addition of the hypertonic solution.

In some embodiments, the osmolarity of a hypertonic solution is greater than the physiological osmolarity of a cell, such as is generally greater than or greater than about 300 mOsm/L. In some embodiments, the hypertonic solution can be any solution that has a greater concentration of solute as compared to the inside of the cell. In some embodiments, a hypertonic solution has an appropriate concentration of a solute that is effective at reducing or removing cell debris in a lysed cell composition.

In some embodiments, a solute for use in a hypertonic solution includes, but is not limited to, salts such as sodium chloride (NaCl), ammonium chloride, potassium chloride, sodium citrate, and sugars such as dextrose, glucose and sucrose. In some embodiments, a hypertonic solution for use in a method described herein can comprise one or more of sodium chloride, ammonium chloride, potassium chloride, or sodium citrate. In some embodiments, the hypertonic solution comprises sodium chloride. In some embodiments, the hypertonic solution comprises sucrose. Hypertonic solutions may comprise further agents such as, but not limited to, buffering agents (e.g., HEPES) and protease inhibitors. The pH of the hypertonic solution can be adjusted as needed, preferably to a pH that does not damage the non-cell particles (e.g. microspheres or bead particles) described herein.

In some embodiments, the hypertonic solution comprises a weight percent (% w/v) of solute of between about 1.5% and about 15% or between about 2.5% and about 12%. In some embodiments, the hypertonic solution has an osmolarity of between about 300 mOsm/L and about 5000 mOsm/L or between about 1800 mM and about 2000 mM. In some embodiments, the hypertonic solution has an osmolarity greater than about 300 mOsm/L or greater than about 4000 mOsm/L.

In some embodiments, the volumes of the hypertonic solution can be chosen or adjusted as needed to optimize cell lysis and/or removal of cell debris from the lysed cell compositions described herein. For instance, when higher cell numbers are used, the reagent volumes and total volumes can be scaled up accordingly. In some embodiments, the volume of the hypertonic cell suspension that is incubated is 1 mL to 1000 mL, or at least or about at least 1 mL, 5 mL, 10 mL, 25 mL, 50 mL, 75 mL, 100 mL, 200 mL, 300 mL, 400 mL or 500 mL.

3. Enrichment and Washing

In some embodiments, prior to analyzing, determining or detecting the presence, absence, number, and/or concentration of particles (e.g., bead particles) in the output composition, the method can further include one or more steps for enriching the samples for the particles (e.g., bead particles) and/or removing or reducing the cell debris in the output composition, such as by performing one or more enrichment and/or separation steps, wash steps or rinse steps of the output composition, resulting in an enriched output composition. In some embodiments, the wash steps or rinse steps comprise a plurality or washes or rinses, such as two, three, four times or more.

In some embodiments herein, after performing the lysis, the output composition is further processed to wash, rinse and/or enrich or separate the particles (e.g. microspheres or bead particles) from other material or debris that may be present in the lysed composition, resulting in an enriched output composition. In some embodiments, the output composition is washed or rinsed a plurality of times, such as two, three, four, or more times. In some embodiments, enriching comprises increasing the number or percentage of the particular component, e.g., compared to the total number of the particular component and one or more other components in the composition or volume of the composition, such as by positive selection based on one or more feature or property of the particular component, or by negative selection based on one or more feature or property not exhibited by the particular component. In some embodiments, a non-cell particle (e.g. bead) is enriched in a composition that contains cells or cell debris (e.g. lysed cells), in that its percentage in the composition can be increased, by selection of the non-cell particle based on a property or feature of the non-cell particle that is not exhibited by one or more cells in the composition. As one non-limiting example, where the particle (e.g. bead) is magnetic, such as contains a magnetic, paramagnetic core or supraparamagnetic core, the enriching comprises using magnetic selection. In some embodiments, enriching does not comprise complete removal of the one or more other components from the composition. In some embodiments, enriching does not comprise the particular component is present at or near 100% in the enriched composition.

In some embodiments, after performing the lysis, the output composition is processed to pellet (e.g., by centrifugation), if present, any particles (e.g. microspheres or bead particles) in the output composition, resulting in an enriched output composition. In some embodiments, the output composition is an enriched output composition.

In some aspects, after performing the lysis, the output composition is further processed to enrich for and/or separate the particles (e.g. microspheres or bead particles) from other material or debris that may be present in the cell composition. In some embodiments, the particles are magnetic particles, and the enrichment step involves exposing the lysed composition, e.g., output composition, to a magnetic field. In some aspects, the output composition is exposed to a magnetic field, and particles that are magnetically responsive or magnetizable bead particles attached thereto will be attracted to the magnet and separated from other material or debris that may be present in the lysed composition, e.g., output composition. In some embodiments, the output composition after lysis is exposed to a magnet that is specifically designed to attract and separate the magnetic particles, e.g., magnetic bead particles, that can be present in the sample. In some embodiments, the type of magnet used in the enrichment step depends on the type, size and/or magneticity of the bead particles that are contained in the sample or the input composition. In some embodiments, exemplary magnets for enriching or separating magnetic particles include DynaMag™-2 Magnet (Invitrogen), DynaMag™ CTS™ Magnet (Invitrogen), CliniMACS® System (Miltenyi Biotec) EasySep™ Magnet (STEMCELL Technologies), MojoSort™ Magnetic system (BioLegend), or other known magnets or systems used to separate magnetic particles.

In some embodiments, after performing the lysis, the output composition can be further processed to pellet (e.g., by centrifugation), if present, any particles (e.g. microspheres or bead particles) in the output composition. Methods for pelleting particles in compositions are well known. In some embodiments, an output composition can be spun in a centrifuge at a centrifugation speed sufficient to pellet, if present, any particles. In some embodiments, the centrifugation speed is sufficient to pellet the particles (e.g. microspheres or bead particles) without damaging such particles. In some embodiments, the centrifugation speed can be adjusted to take into account the model of the centrifuge and/or centrifuge rotor radius. In some embodiments, centrifugation is at a speed of from or from about 200×g to 1000×g, such as generally at least or about at least 400×g, 450×g, 500×g or 600×g. The centrifugation can proceed for a time sufficient to pellet the particles. In some embodiments, the output composition is centrifuged from 1 minutes to 60 minutes, such as generally 1 minute to 30 minutes, 1 minute to 15 minutes or 1 minute to 5 minutes, for example, at least or at least about 1 minute, 2 minutes, 3 minutes, 4 minutes, 5 minutes, 6 minutes, 7 minutes, 8 minutes, 9 minutes, 10 minutes, 15 minutes or 30 minutes.

In some embodiments, after pelleting, the volume of the output composition can be adjusted as desired, such as by completely or partially removing the supernatant solution and/or resuspending the pellet in a specified volume of a solution suitable for subsequent analysis. In some embodiments, after pelleting, all or substantially all of the supernatant can be removed and replaced with fresh buffer or media to a desired volume. In general, the buffer or media can be any that is compatible with the particles and/or does not interfere with subsequent visualization or detection of the particles. In other embodiments, after pelleting, the volume of the output composition can be reduced (e.g., by removing a volume of the supernatant in the centrifuged output composition or reducing the volume or the total centrifuged output composition) to a desired volume prior to determining the presence or number of particles (e.g. microspheres or bead particles). In some embodiments, the volume of the output composition can be reduced by less than about 100% but greater than about 50%, about 60%, about 70%, about 80%, about 90% or about 95% compared to the volume of the output composition prior to the pelleting (e.g. centrifugation).

In some embodiments, replacing, reducing or removing supernatant from the output composition effects rinsing or washing of the output composition prior to determining the presence, absence, number, and/or concentration of particles (e.g., bead particles). In some embodiments, replacing, reducing or removing supernatant from the output composition and/or resuspension in a specified volume effects concentration or dilution (as appropriate) of the output composition prior to determining the presence, absence, number, and/or concentration of particles. In some embodiments, the steps of pelleting (e.g. by centrifugation) and replacing, washing or removing supernatant of the output composition and/or resuspension in a specified volume can be repeated a plurality of times. In some aspects, multiple sequential resuspension can be used to obtain all or substantially all of the bead particles present in the output composition. For example, in some embodiments, one particular volume of the solution can be added to a container (e.g., test tube) containing the pelleted particles, to resuspend the pellet, transferred to a different container for analysis (e.g., a well of a multi-well plate), and another volume of fresh solution can be added to the initial container to resuspend and transfer any remaining particles to the container for analysis.

In some embodiments, the total volume of the output composition after replacing, reducing or removing supernatant and/or resuspending is a volume that permits detection of the particles in the sample (e.g., suitable concentration for subsequent detection methods, such as automated fluorescence imaging and/or analysis). In some aspects, one or more steps of the analysis or detection is carried out by a machine, a robot and/or a computer-implemented algorithm. In some embodiments, the desired volume is a volume required or desired for optimal performance of the machine, robot and/or computer-implemented algorithm.

In some aspects, exemplary volume of the output composition, e.g., enriched output composition, at or prior to analysis, is from at or about 10 μL to at or about 10 mL, such as 10 μL to 1 mL, 25 μL to 500 μL, 50 μL to 250 μL or 75 μL to 125 μL. In some aspects, exemplary volume of the composition, at or prior to analysis, is at or about or is at least at or about 10 μL, 25 μL, 50 μL, 75 μL, 100 μL, 125 μL, 200 μL, 250 μL, 500 μL, 750 μL, 1 mL, 2 mL, 3 mL, 4 mL, 5 mL, 6 mL, 7 mL, 8 mL, 9 mL, or 10 mL. In some embodiments, the volume is from or from about 0.25 mL to at or about 50 mL, such as from or from about 0.5 mL to at or about 50 mL, 0.5 mL to 25 mL, 0.5 mL to 10 mL, 0.5 mL to 5 mL, 0.5 mL to 1 mL, 1 mL to 50 mL, 1 mL to 25 mL, 1 mL to 10 mL, 1 mL to 5 mL, 5 mL to 50 mL, 5 mL to 25 mL, 5 mL to 10 mL, 10 mL to 50 mL, 10 mL to 25 mL or 25 mL to 50 mL. In some embodiments, the volume is at least or at least about or 0.5 mL, 1 mL, 1.5 mL, 2 mL, 3 mL, 4 mL, 5 mL, 6 mL, 7 mL, 8 mL, 9 mL, 10 mL, 15 mL, 20 mL, 30 mL, 40 mL or 50 mL.

B. Methods of Detecting or Counting (Enumerating) Particles

In some embodiments, the methods involve analyzing the output composition, e.g., enriched output composition, to determine the presence or absence of particles in the output composition, e.g., enriched output composition. In some embodiments, the analyzing step involves obtaining fluorescence images. In some embodiments, the analyzing step involves analysis of obtained fluorescence images to determine presence, absence, number, and/or concentration of particles (e.g. microspheres or bead particles) present in the output composition, e.g., enriched output composition.

Methods for determining the presence of (e.g. concentration or number) and/or detecting particles in an output composition, e.g., a sample after the lysis methods have been performed and optionally further enriched, can be performed using techniques well known. In some embodiments, methods for determining the presence, absence, number, and/or concentration of particles (e.g. microspheres or bead particles) in an output composition can include manual counting, electronic counting, microscopy (e.g., fluorescent microscopy), affinity-based detection, or sorting (e.g., magnetic bead sorting). Techniques for use in such methods include, but are not limited to, flow cytometry (e.g., fluorescence-activated cell sorting (FACS)), spectrophotometry, microscopy such as bright field microscopy (e.g., using a hemocytometer), phase contrast microscopy, fluorescent microscopy, and electron microscopy, and biosensor arrays. See Giouroudi et al., Int J Mol Sci., 2013, 14(9):18535-18556.

In some embodiments, the analyzing is carried out using a computer-implemented image analysis. In some embodiments, one or more steps of the method is high-throughput and/or automated. In some embodiments, one or more steps of the method is carried out by a machine, a robot and/or a computer-implemented algorithm. In some embodiments, the technique can be manual or automated. In some cases, a particle count (e.g., bead count) can be obtained using such techniques and the particle count can be repeated. After the particle count is repeated, the obtained particle counts can be averaged and a standard deviation can be determined.

In some embodiments, the output composition, such as the output composition after lysis of the sample, can be prepared by one or more processing steps prior to analyzing the output composition by fluorescence imaging, e.g., determining the presence, absence, number, and/or concentration of particles in the methods described herein. In some cases, the one or more processing steps of the output composition involve separation, centrifugation, washing, and/or incubation, such as any enrichment and/or washing steps described in Section II.A.3 above, resulting in an enriched output composition.

In some embodiments, the output composition, e.g., enriched output composition, does not contain additional agent for detecting the particles, e.g., where the additional agent comprises a detectable moiety or is capable of producing a detectable signal. In some embodiments, the output composition is not incubated with any additional detectable reagent or moiety for detecting the one or more non-cell particles is added to the output composition prior to the analyzing step.

In some embodiments, the one or more non-cell particles (e.g., bead particles) are autoflourescent. In some embodiments, the one or more non-cell particles do not comprise an additional detectable reagent or moiety. In some embodiments, the analyzing, e.g., determining the presence, absence, number, and/or concentration of particles, is performed without adding detectable reagent or moiety for detecting the one or more non-cell particles. In some aspects, the autofluorescence of the particles can be used for detection and analysis, without the requirement of additional detectable reagents or moieties. In some embodiments, provided is a method of enumerating or detecting the presence or absence of particles in a cell composition, wherein the method comprises the steps of determining the presence, absence, number and/or concentration of particles in the output composition without using any binding agents that specifically binds to the material on surface of the particle and/or an additional agent comprising a detectable moiety or an additional agent that is capable of producing a detectable signal.

In some embodiments of any of the provided embodiments, the analyzing comprises detecting the autofluorescence of one or more non-cell particles at between about 650 nm and about 700 nm. In some embodiments of any of the provided embodiments, the analyzing comprises detecting the autofluorescence of one or more non-cell particles at about 685 nm.

In some embodiments, the presence, absence, amount, or concentration of particles, e.g., bead particles, in a sample, such as a cell sample and/or a cell composition, is detected, and/or assessed with the use of a machine and/or apparatus suitable or cell and/or microscopic particle imaging. In some embodiments, the particles are assessed and/or detected by the machine and/or apparatus optically in a sample, e.g., by visible light imaging, fluorescence imaging, chemiluminescence imaging, and/or absorbance imaging. In particular embodiments, the machine and/or apparatus may include, but is not limited to, microscopes, such as fluorescence microscopes and confocal microscopes, plate readers, and microplate readers. In particular embodiments, the machine or apparatus is capable of wide-field microscopy. In some embodiments, the detection and/or assessment of the particles with the machine or apparatus is manual. In certain embodiments, the detection and/or assessment of the particles with the machine or apparatus is automated.

In particular embodiments, the particles, e.g., bead particles, are detected with a machine or apparatus capable of imaging, e.g., fluorescence imaging. In certain embodiments, the machine or apparatus includes a light source, such as one or more of xenon arc lamps or mercury-vapor lamps with an excitation filter, lasers, supercontinuum sources, and/or high-power LEDs. In certain embodiments, the machine and/or apparatus is capable of UV-visual light absorbance, fluorescence, luminescence, fluorescence polarization, time-resolved fluorescence, and/or alpha detection. In particular embodiments, the machine and/or apparatus is capable of fluorescence, brightfield, color brightfield, and/or phase contrast imaging. In some embodiments, the light source emits light that excites one or more non-cell particles. In some embodiments, the light source is capable of exciting or excites an autofluorescence. In some embodiments of any of the provided embodiments, the light source emits light with a wavelength of between about 600 nm and about 650 nm. In some embodiments of any of the provided embodiments, the light source emits light with a wavelength of about 628 nm.

In some embodiments, the machine or apparatus contains one or more lens. In some embodiments, the machine and/or apparatus contains one or more objectives. In some embodiments, the objectives include one or more of 1.25×, 2.5×, 2.5×, 4×, 10×, 12×, 20×, 25× 30×, 40×, 50×, 60×, 70×, 75×, and 100×. In some embodiments, the machine and/or apparatus contains one or more imaging filters, e.g., imaging filter cubes. In some embodiments, the imaging filters include one or more of DAPI, CFP, GFP, YFP, RFP, Texas Red, CY5, CY7, Acridine Orange (ACR OR), CFP-YFP FRET, propidium, Iodide, chlorophyll, phycoerythrin, CY5.5, TagBFP, Alexa568, and Ex377/Em647 filters. In some embodiments, the machine or apparatus includes one or more imaging LED. In some embodiments, the imaging LED emits a wavelength of between 365 nm and 850 nm, between 365 and 750 nm, inclusive, or at or about 365 nm, 390 nm, 465 nm, 505 nm, 523 nm, 590 nm, 623 nm, 655 nm, and/or 740 nm.

In some embodiments, fluorescence imaging comprises obtaining fluorescent micrographs of an output composition or a portion thereof by detecting autofluorescence of one or more non-cell particles in a Cy5, red, and/or far red channel, and determining the fluorescent intensity of image objects from the fluorescent micrographs. In some embodiments, fluorescence imaging comprises obtaining fluorescent micrographs of an output composition or a portion thereof by detecting autofluorescence of one or more non-cell particles after exciting the output composition with light at a wavelength of about 628 nm, and determining the fluorescent intensity of image objects from the fluorescent micrographs. In some aspects, fluorescence imaging comprises obtaining fluorescent micrographs of an output composition or a portion thereof by detecting autofluorescence of one or more non-cell particles in a Cy5, red, and/or far red channel, after exciting the output composition with light at a wavelength of about 628 nm, and determining the fluorescent intensity of image objects from the fluorescent micrographs. In some cases, the fluorescent intensity is the mean fluorescent intensity.

In some embodiments of any of the provided embodiments, methods of visualizing or detecting non-cell particles comprises detecting the autofluorescence of one or more non-cell particles. In some embodiments of any of the provided embodiments, methods of visualizing or detecting non-cell particles comprises detecting the autofluorescence of one or more non-cell particles that has been illuminated by a light source. In some cases, the non-cell particles autoflouresce more strongly than cells or cellular debris at a particular wavelength, allowing for differentiation between particles and cells or cellular debris. In some cases, the non-cell particles autofluoresce at a different wavelength than cells or cellular debris, allowing for differentiation between particles and cells or cellular debris. In some cases, the image objects in the fluorescent micrographs comprise one or more non-cell particles that can be identified and enumerated.

In certain embodiments, the machine or apparatus is equipped with a camera capable of capturing images, e.g., digital images, of a sample for suitable for analysis. In some embodiments, the camera is capable of autofocus, e.g., automatically focus images collected from a sample without any user input. In some embodiments, the autofocus may be image based autofocus, user trained autofocus, and/or laser autofocus. In some embodiments, the images are images of fluorescence signal, brightfield images, and/or phase contrast images. In particular embodiments, the images may be analyzed to detect objects by measuring one or more parameters, e.g., size, fluorescence, area, or shape.

In some embodiments, the machine or apparatus is capable of capturing one or more brightfield images from a sample. In certain embodiments, the machine or apparatus is capable of capturing one/or more fluorescent images from the sample. In particular embodiments, the machine and/or apparatus is capable of capturing a brightfield image and a fluorescent image from the same sample. In particular embodiments, the images are collected in a manner that allows for the images to be overlaid, such that the same objects, e.g., cells and/or particles, are imaged in the sample are imaged in brightfield and fluorescence. In some embodiments, the image captures an area of the sample between or between about 1 μm to 1,000 μm by between or between about 1 μm and 1,000 μm. In some embodiments, the image captures between or between about 1 μm and 2,000 μm, 1 μm and 100 μm, 10 μm and 500 μm, 100 μm and 1,000 μm, 400 μm and 600 μm, 500 μm and 1,000 μm, 400 μm and 800 μm, 600 μm and 800 μm, or 250 μm and 750 μm by between or between about 1 μm and 2,000 μm, 1 μm and 100 μm, 10 μm and 500 μm, 100 μm and 1,000 μm, 400 μm and 600 μm, 500 μm and 1,000 μm, 400 μm and 800 μm, 600 μm and 800 μm, or 250 μm and 750 μm of the sample.

Suitable machines and/or apparatus for use with the provided methods are known, and include but are not limited to microscopes, fluorescence microscopes, confocal microscopes, plate readers and multiplate readers. In some embodiments, the machine or apparatus is a microplate reader. In some embodiments, the machine or apparatus is a plate reader, e.g., a microplate reader. In some embodiments, the plate reader and/or microplate reader images samples on microscope slides, petri dishes, cell culture dishes, cell culture flasks, counting chambers, such as a hemocytometer, and plates, such as 6-well, 12-well, 24-well, 48-well, 96-well, 384-well plates, and/or plates with up to 6, 12, 24, 48, 96, 386, or 1536 wells. Suitable microplate readers for use with the provided methods include those described in U.S. Pat. Nos. 8,218,141 and 9,557,217, hereby incorporated by reference in their entirety.

In particular embodiments, images, e.g., fluorescent images, are analyzed to detect the presence or absence of objects with one or more properties. In certain embodiments, the images are analyzed manually, such as by a technician. In particular embodiments, the image analysis is automated, such as performed by software. Suitable imaging software is known, and includes but is not limited to Gen5 software (BIOTEK, Winooski, VT, U.S.A.). In some embodiments, it is contemplated that one of skill will understand how to use, tailor, and/or program available software to detect parameters, e.g., parameters of objects, captured in an image.

In particular embodiments, fluorescing imaging is used to detect the presence of absence of objects with one or more properties. In particular embodiments, the objects are one or more non-cell particles. In particular embodiments, one or more non-cell particles is autofluorescent. In particular embodiments, one or more autofluorescent non-cell particles is capable of exhibiting autofluorescence and/or emitting an autofluorescent signal. In particular embodiments, one or more autofluorescent non-cell particles exhibits autofluorescence and/or emits an autofluorescent signal when it absorbs light emitted from a light source. In particular embodiments, fluorescence imaging comprises a light source that illuminates one or more non-cell particles, causing it to exhibit autofluorescence. In particular embodiments, the non-cell particles exhibit autofluorescence when illuminated by a light source during fluorescence imaging. In some embodiments, one or more non-cell particles exhibits autofluorescence at a wavelength of between about 450 and about 750 nm when it absorbs light. In some embodiments, one or more non-cell particles exhibits autofluorescence at a wavelength of between about 600 nm and about 750 nm when it absorbs light. In some embodiments, one or more non-cell particles exhibits autofluorescence at a wavelength of between about 660 nm and about 720 nm when it absorbs light. In some embodiments, one or more non-cell particles exhibits autofluorescence at a wavelength of between about 660 nm and about 700 nm when it absorbs light. In some embodiments, one or more non-cell particles exhibits autofluorescence at a wavelength of between about 675 nm and about 700 nm when it absorbs light. In some embodiments, one or more non-cell particles exhibits autofluorescence at a wavelength of about 685 nm when it absorbs light.

In some embodiments, one or more non-cell particles exhibits autofluorescence when it absorbs light with a wavelength of between about 450 nm and about 700 nm. In some embodiments, one or more non-cell particles exhibits autofluorescence when it absorbs light with a wavelength of between about 500 nm and about 700 nm. In some embodiments, one or more non-cell particles exhibits autofluorescence when it absorbs light with a wavelength of between about 600 nm and about 700 nm. In some embodiments, one or more non-cell particles exhibits autofluorescence when it absorbs light with a wavelength of between about 600 nm and about 650 nm. In some embodiments, one or more non-cell particles exhibits autofluorescence when it absorbs light with a wavelength of about 628 nm.

In some aspects, one or more non-cell particles exhibits autofluorescence at a different wavelength than cells or cellular debris. In some embodiments, cells or cellular debris exhibit less autofluorescence than one or more non-cell particles upon excitation with light that is between 600 and 650 nm. In some embodiments, cells or cellular debris exhibit less autofluorescence than do one or more non-cell particles upon excitation with light that is about 628 nm. In some embodiments, one or more non-cell particles exhibits more autofluorescence than do cells or cellular debris upon excitation with light that is between 600 and 650 nm. In some embodiments, one or more non-cell particles exhibits more autofluorescence than do cells or cellular debris upon excitation with light that is about 628 nm. In some embodiments, one or more non-cell particles exhibits more autofluorescence that can be detected in a Cy5 channel than do cells or cellular debris upon excitation with light that is about 628 nm. In some embodiments, one or more non-cell particles exhibits more autofluorescence that can be detected in a red channel than do cells or cellular debris upon excitation with light that is about 628 nm. In some embodiments, one or more non-cell particles exhibit more autofluorescence that can be detected in a far-red channel than do cells or cellular debris upon excitation with light that is about 628 nm.

In some embodiments, the autofluorescence of one of more non-cell particles can be detected at about 685 nm. In some embodiments, the autofluorescence of one of more non-cell particles can be detected in a Cy5 channel. In some embodiments, the autofluorescence of one of more non-cell particles can be detected in a red channel. In some embodiments, the autofluorescence of one of more non-cell particles can be detected in a far-red channel. In some embodiments, the autofluorescence of one or more non-cell particles can be detected when it absorbs light with a wavelength of about 628 nm. In some embodiments, one or more non-cell particles exhibits autofluorescence at a wavelength of about 685 nm when it absorbs light with a wavelength about 628 nm.

In particular embodiments, images, e.g., brightfield images, are analyzed to detect the presence or absence of objects with one or more properties. In certain embodiments, the images are analyzed manually, such as by a technician. In particular embodiments, the image analysis is automated, such as performed by software. Suitable imaging software is known, and includes but is not limited to Gen5 software (BIOTEK, Winooski, VT, U.S.A.). In some embodiments, it is contemplated that one of skill will understand how to use, tailor, and/or program available software to detect parameters, e.g., parameters of objects, captured in an image.

In particular embodiments, images, e.g., digital images, are analyzed for objects with one or more parameters, e.g., area and/or size, fluorescent intensity (FI), brightfield intensity, and a shape factor, e.g., circulatory. In some embodiments, the images are analyzed for objects having one or more parameters have a value within a range and/or above or below a threshold values. In some embodiments, the fluorescent intensity is the mean fluorescent intensity. In some embodiments, the brightfield intensity is the mean brightfield intensity.

In some embodiments, the image is analyzed to determine the presence or absence of objects. Objects in the image may be identified by detecting signal over background, or by comparing phase contrast and fluorescent images of the sample, such as overlaid phase contrast and florescent images. The objects may then be qualified, quantified, and/or characterized by detect the values of one or more parameters. For example, an object may be detected, e.g., by manual, automated, and/or software analysis, and may be identified as a cell or a non-cell based on the value of one or more parameters. For example, in some embodiments, non-cell particles might display higher or lower fluorescent intensity than cells, and/or may have more circular appearance. In some embodiments, an image object can be classified as a single ("singlet"), double ("doublet"), or other multiple of non-cell particle. In some embodiments, an image object is classified as a single, double, or other multiple of non-cell particle based on one or more parameters, such as diameter, area, circularity, and fluorescence.

In some embodiments, the one or more parameters is or includes a shape factor. In some embodiments the shape factor is selected from one or more of circularity, elongation, compactness, and/or waviness.

In some embodiments, the shape factor is circularity and/or isoperimetric quotient. In some embodiments, the circularity and/or isoperimetric quotient is a function of the perimeter P and the area A: Circularity=$4 \pi A/P^2$, wherein a mathematically or geometrically perfect circle has a circularity of 1.0. In some embodiments, an object that is determined to be a non-cell particle, e.g., a bead, has circularity of or of at least 0.1. 0.2, 0.3, 0.4, 0.5, 0.6, 0.7, 0.8, 0.9, or 1.0. In some embodiments, the an object that is determined to be a non-cell particle, e.g., a bead, has a circularity of between 0.1 and 1, 0.3 and 0.6, 0.4 and 1.0, 0.6 and 1.0, 0.6 and 0.8, 0.3 and 0.7, 0.4 and 0.6, or 0.7 and 1.0, inclusive. In some embodiments, objects on an image are determined to be a non-cell particle, e.g., a bead, if the object has a circularity of or of at least 0.1. 0.2, 0.3, 0.4, 0.5, 0.6, 0.7, 0.8, 0.9, or 1.0. In some embodiments, and object is determined to be a non-cell particle, e.g., a bead, if it has a circularity of between 0.1 and 1, 0.3 and 0.6, 0.4 and 1.0, 0.6 and 1.0, 0.6 and 0.8, 0.3 and 0.7, 0.4 and 0.6, or 0.7 and 1.0, inclusive.

In some embodiments, an image object is determined to be a single non-cell particle, e.g., a single bead or a "singlet," if the image object has a circularity of between or between about 0.1 and 1, 0.3 and 0.6, 0.4 and 1.0, 0.6 and 1.0, 0.6 and 0.8, 0.3 and 0.7, or 0.7 and 1.0, inclusive. In some embodiments, an image object is determined to be a single non-cell particle, e.g., a single bead or a "singlet," if the image object has a circularity of between or between about 0.7 and 1.0, inclusive. In some embodiments, an image object is determined to be two non-cell particles, e.g., two beads or a "doublet," if the image object has a circularity of between or between about 0.1 and 1, 0.3 and 0.7, or 0.4 and 6.0. In some embodiments, an image object is determined to be two non-cell particles, e.g., two beads or a "doublet," if the image object has a circularity of between or between about 0.4 and 0.6.

In certain embodiments, the one or more parameters is or includes size. In some embodiments, the size is determined by measuring diameter and/or radius of the object. In particular embodiments, an object that is determined to be a bead has a diameter of between or between about 0.1 μm and 25 μm, 0.5 μm and 20 μm, 3 μm and 15 μm, 1 μm and 10 μm, 2 μm and 10 μm, 3 μm and 10 μm, 1 μm and 5 μm, 6 μm and 8 μm, 6.5 μm and 8.5 μm, or 5 μm and 10 μm. In some embodiments, the an object that is determined to be a bead has a diameter of between or between about 0.1 μm and 25 μm, 0.5 μm and 20 μm, 3 μm and 15 μm, 1 μm and 10 μm, 2 μm and 10 μm, 3 μm and 10 μm, 1 μm and 5 μm, 6 μm and 8 μm, 6.5 μm and 8.5 μm, or 5 μm and 10 μm. In particular embodiments, an object that is determined to be a bead has a diameter of between or between or between about 3 μm and 15 μm. In particular embodiments, an object that is determined to be a bead has a diameter of between or between or between about 1 μm and 5 μm.

In some embodiments, an image object is determined to be a single non-cell particle, e.g., a single bead or a "singlet," if the object has a diameter of between or between about 0.1 μm and 25 μm, 0.5 μm and 20 μm, 3 μm and 15 μm, 1 μm and 10 μm, 2 μm and 10 μm, 3 μm and 10 μm, 1 μm and 5 μm, 6 μm and 8 μm, 6.5 μm and 8.5 μm, or 5 μm and 10 μm. In some embodiments, an image object is determined to be a single non-cell particle, e.g., a single bead or a "singlet," if the image object has a diameter of between about 1 μm and about 10 μm. In some embodiments, an image object is determined to be a single non-cell particle, e.g., a single bead or a "singlet," if the image object has a diameter of between about 1 μm and about 7 μm. In some embodiments, an image object is determined to be a single non-cell particle, e.g., a single bead or a "singlet," if the image object has a diameter of between about 1 μm and about 5 inn. In some embodiments, an image object is determined to be two non-cell particles, e.g., two beads or a "doublet," if the image object has a diameter of between or between about 0.2 μm and 50 μm, 1 μm and 40 μm, 1 μm and 5 μm, 3 μm and 15 μm, 6 μm and 30 μm, 2 μm and 20 μm, 4 μm and 20 μm, 6 μm and 20 μm, 2 μm and 10 μm, 12 μm and 16 μm, 13 μm and 17 μm, or 10 μm and 20 μm. In some embodiments, an image object is determined to be two non-cell particles, e.g., two beads or a "doublet," if the image object has a diameter of between about 10 inn and about 20 μm.

In some embodiments, the one or more parameters is or includes the area of the object. In some embodiments, an object that is determined to be a bead has an area of between 0.5 μm², 1 μm² and 500 μm², 10 μm² and 100 μm², 25 μm² and 100 μm², 25 μm² and 75 μm², 40 μm² and 60 μm², or 50 μm² and 60 μm², inclusive. In some embodiments, an object that is determined to be a bead has an area of less than 500 μm², 200 μm², 100 μm², 90 μm², 80 μm², 70 μm², 60 μm², or 50 μm². In particular embodiments, an object that is determined to be a bead has an area greater than 10 μm², 25 μm², 50 μm², 40 μm², 80 μm², 70 μm², 60 μm², or 50 μm². In some embodiments, an object is determined to be a bead if the object has an area of between 0.5 μm² and 500 μm², 1 μm² and 500 μm², 10 μm² and 100 μm², 25 μm² and 100 μm², 25 μm² and 75 μm², 40 μm² and 60 μm², or 50 μm² and 60 μm², inclusive. In some embodiments, an object is determined to be a bead if it has an area of less than 500 μm², 200 inn, 100 μm², 90 μm², 80 μm², 70 μm², 60 μm², or 50 μm². In particular embodiments, an object is determined to be a bead if it has an area greater than 10 μm², 25 μm², 50 μm², 40 μm², 80 μm², 70 μm², 60 μm, or 50 μm. In particular embodiments, an object is determined to be a bead if it has an area less than 130 μm². In particular embodiments, an object is determined to be a bead if it has an area less than 65 μm².

In some embodiments, an image object is determined to be a single non-cell particle, e.g., a single bead or a "singlet," if the object has an area of between or between about 1 μm² and 500 μm², 10 μm² and 100 μm², 25 μm² and 100 μm², 25 μm² and 75 μm², 40 μm² and 70 μm², or 50 μm² and 65 μm², inclusive. In some embodiments, an image object is determined to be a single non-cell particle, e.g., a single bead or a "singlet," if the image object has an area of less than about 65 μm². In some embodiments, an image object is determined to be two non-cell particles, e.g., two beads or a "doublet," if the object has an area of between or between about 2 μm² and 1000 μm², 20 μm² and 200 μm², 50 μm² and 200 μm², 50 μm² and 150 μm², 60 μm² and 140 μm², or 65 μm² and 130 μm², inclusive. In some embodiments, an image object is determined to be two non-cell particles, e.g., two beads or a "doublet," if the image object has an area of between or between about 65 μm² and 130 μm².

In some embodiments, the one or more parameters is or includes the area of the object. In some embodiments, an object that is determined to be a bead has an area of between 1 μm² and 500 μm², 10 μm² and 100 μm², 25 μm² and 100 μm², 25 μm² and 75 μm², 40 μm² and 60 μm², or 50 μm² and 60 μm², inclusive. In some embodiments, an object that is determined to be a bead has an area of less than 500 μm², 200 μm², 100 μm², 90 μm², 80 μm², 70 μm², 60 μm², or 50 μm². In particular embodiments, an object that is determined to be a bead has an area greater than 10 μm², 25 μm², 50 μm², 40 μm², 80 μm², 70 μm², 60 μm², or 50 μm². In some embodiments, an object is determined to be a bead if the object has an area of between 1 μm² and 500 μm², 10 μm² and 100 μm², 25 μm² and 100 μm², 25 μm² and 75 μm², 40 μm² and 60 μm², or 50 μm² and 60 μm², inclusive. In some embodiments, an object is determined to be a bead if it has an area of less than 500 μm², 200 μm², 100 μm², 90 μm², 80 μm², 70 μm², 60 μm², or 50 μm². In particular embodiments, an object is determined to be a bead if it has an area greater than 10 μm², 25 μm², 50 μm², 40 μm², 80 μm², 70 μm², 60 μm², or 50 μm².

In some embodiments, the object has a fluorescent intensity (FI). In particular embodiments, the FI is measured from light reflected from imaging filters. In some embodiments, the imaging filter is or includes DAPI, CFP, GFP, YFP, RFP, Texas Red, CY5, CY7, Acridine Orange (ACR OR), CFP-YFP FRET, propidium, Iodide, chlorophyll, phycoerythrin, CY5.5, TagBFP, Alexa568, or Ex377/Em647. The fluorescent intensity is measured from between 365 nm and 850 nm, between 365 and 750 nm, between 366 and 578 nm, between 250 and 1,000 nm, between 350 and 1,000 nm, between 457 and 514 nm, between 453 and 633 nm, between 658 and 747, or between 658 and 647 nm. In some embodiments, the fluorescent intensity is measured by and/or from stimulation with a mercury arc lamp, xenon arc lamp, tungsten-halogen lamp, blue diode laster, helium-cadmium laser, Nd:YAG laser, helium-neon laser, yellow diode later, krypton ion laser, and/or a red diode laser source. In some embodiments, the fluorescent intensity is the mean fluorescent intensity.

In certain embodiments, the object has a FI that is above background detection. In certain embodiments, the object has a FI that is at least 1-fold, 2-fold, 5-fold, 10-fold, 50-fold, 100-fold, 200-fold, 300-fold, 400-fold, 500-fold, 1,000-fold, 5,000-fold, 20,000-fold, 50,000-fold, or 50,000-fold greater than background, e.g., the detected background signal. In some embodiments, an object that is a bead has an FI that is at least 1-fold, 2-fold, 5-fold, 10-fold, 50-fold, 100-fold, 200-fold, 300-fold, 400-fold, 500-fold, 1,000-fold, 5,000-fold, 20,000-fold, 50,000-fold, or 50,000-fold greater than background. In some embodiments, the fluorescent intensity is the mean fluorescent intensity. In some embodiments, an object that is determined to be a bead has a FI at or above a threshold FI. In certain embodiments, the threshold FI is a mean, median, average, and/or upper bound FI measured from a plurality of objects that are not beads, e.g., cellular debris. In some embodiments, an object that is determined to be a bead has at least 5%, 10%, 20%, 25%, 30%, 40%, 50%, 60%, 70%, 80%, 90%, 100%, 150%, 1-fold, 2-fold, 3-fold, 4-fold, 5-fold, 10-fold, 20-fold, 50-fold, or 100-fold higher FI as compared to mean, median, average, and/or upper bound FI measured from a plurality of objects that are not beads. In particular embodiments, an object is determined to be a bead if the object has an FI at or above a threshold FI. In some embodiments, an object is determined to be a bead if the object has an FI of at least 5%, 10%, 20%, 25%, 30%, 40%, 50%, 60%, 70%, 80%, 90%, 100%, 150%, 1-fold, 2-fold, 3-fold, 4-fold, 5-fold, 10-fold, 20-fold, 50-fold, or 100-fold higher FI as compared to mean, median, average, and/or upper bound FI measured from a plurality of objects that are not beads. In some embodiments, the fluorescent intensity is the mean fluorescent intensity.

In certain embodiments, an object that is determined to be a bead has an FI at or below a threshold FI. In certain embodiments, the threshold FI is a mean, median, average, and/or lower bound FI measured from a plurality of cells. In some embodiments, an object that is determined to be a bead has at least 5%, 10%, 20%, 25%, 30%, 40%, 50%, 60%, 70%, 80%, 90%, 95%, 99%, or 99.9% less FI as compared to mean, median, average, and/or lower bound FI measured from a plurality or particles that are not beads, e.g. cellular debris. In particular embodiments, an object is determined to be a bead if the object has an FI at or below the threshold FI. In some embodiments, an object is determined to be a bead if the object has at least 5%, 10%, 20%, 25%, 30%, 40%, 50%, 60%, 70%, 80%, 90%, 95%, 99%, or 99.9% less FI as compared to mean, median, average, and/or lower bound FI measured from a plurality of objects that are not beads. In some embodiments, the fluorescent intensity is the mean fluorescent intensity.

In some embodiments, an image object is a non-cell particle if: (i) the image object comprises a circularity of at or at least 0.5, 0.6, 0.7, 0.8, or 0.9; (ii) the image object comprises a diameter of between 5 μm and 10 μm, inclusive; and/or (iii) the image object comprises an area of between 25 μm2 and 50 μm2; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity. In some embodiments, the control sample is composition produced by incubating a cell composition comprising the one or more cells but not comprising, or not likely comprising, the one or more non-cell particles, wherein the incubating is under conditions to induce lysis of cells to produce an output composition.

In some embodiments, an image object is a non-cell particle if: (i) the image object comprises a circularity of between or between about 0.4 and 1.0, inclusive; (ii) the image object comprises a diameter of between 1 μm and 15 μm, inclusive; (iii) the image object comprises an area of between 0.5 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is a non-cell particle if: (i) the image object comprises a circularity of between or between about 0.4 and 1.0, inclusive; (ii) the image object comprises a diameter of between 3 μm and 15 μm, inclusive; (iii) the image object comprises an area of between 0.5 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is a non-cell particle if: (i) the image object comprises a circularity of between or between about 0.4 and 1.0, inclusive; (ii) the image object comprises a diameter of between 1 μm and 5 μm, inclusive; (iii) the image object comprises an area of between 0.5 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is a non-cell particle if: (i) the image object comprises a circularity of between or between about 0.4 and 0.6, inclusive; (ii) the image object comprises a diameter of between 1 μm and 15 μm, inclusive; (iii) the image object comprises an area of between 0.5 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is a non-cell particle if: (i) the image object comprises a circularity of between or between about 0.4 and 0.6, inclusive; (ii) the image object comprises a diameter of between 3 μm and 15 μm, inclusive; (iii) the image object comprises an area of between 0.5 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is a non-cell particle if: (i) the image object comprises a circularity of between or between about 0.4 and 0.6, inclusive; (ii) the image object comprises a diameter of between 1 μm and 5 μm, inclusive; (iii) the image object comprises an area of between 0.5 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is a non-cell particle if: (i) the image object comprises a circularity of between or between about 0.7 and 1.0, inclusive; (ii) the image object comprises a diameter of between 1 μm and 15 μm, inclusive; (iii) the image object comprises an area of between 0.5 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is a non-cell particle if: (i) the image object comprises a circularity of between or between about 0.7 and 1.0, inclusive; (ii) the image object comprises a diameter of between 3 μm and 15 μm, inclusive; (iii) the image object comprises an area of between 0.5 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is a non-cell particle if: (i) the image object comprises a circularity of between or between about 0.7 and 1.0, inclusive; (ii) the image object comprises a diameter of between 1 μm and 5 μm, inclusive; (iii) the image object comprises an area of between 0.5 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is classified as a single ("singlet"), double ("doublet"), or other multiple of non-cell particle. In some embodiments, an image object is classified as a single, double, or other multiple of non-cell particle based on one or more parameters. In some embodiments, an image object is classified as a single ("singlet"), double ("doublet"), or other multiple of non-cell particle based on the circularity of the object. In some embodiments, an image object is classified as a single non-cell particle if the image object comprises a circularity of between about 0.7 and about 1.0. In some embodiments, an image object is classified as a double non-cell particle if the image object comprises a circularity of between about 0.4 and about 0.6. In some embodiments, an image object is classified as more than two non-cell particles if the image object comprises a circularity of 0.4 or less.

In some embodiments, an image object is classified as a single ("singlet"), double ("doublet"), or other multiple of non-cell particle based on the diameter of the object. In some embodiments, an image object is classified as a single non-cell particle if the image object comprises a diameter of between about 1.0 μm and about 7.5 μm. In some embodiments, an image object is classified as a double non-cell particle if the image object comprises a diameter of between about 7.5 μm and about 15 μm. In some embodiments, an image object is classified as more than two non-cell particles if the image object comprises a diameter of more than about 15 μm.

In some embodiments, an image object is classified as a single ("singlet"), double ("doublet"), or other multiple of non-cell particle based on the area of the object. In some embodiments, an image object is classified as a single non-cell particle if the image object comprises an area of less than about 65 μm$^2$. In some embodiments, an image object is classified as a double non-cell particle if the image object comprises an area of between or between about 65 μm$^2$ and 130 μm$^2$. In some embodiments, an image object is classified as more than two non-cell particles if the image object comprises an area of more than about 130 μm$^2$.

In some embodiments, an image object is classified as a single ("singlet"), double ("doublet"), or other multiple of non-cell particle based on the circularity, diameter, and/or area of the object. In some embodiments, an image object is a single non-cell particle ("singlet") if: (i) the image object comprises a circularity of between or between about 0.7 and 1.0; (ii) the image object comprises a diameter of between 1 μm and 7.5 μm, inclusive; (iii) the image object comprises an area of less than 65 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is a double non-cell particle ("doublet"), e.g. two non-cell particles, if: (i) the image object comprises a circularity of between or between about 0.4 and 0.6; (ii) the image object comprises a diameter of between 7.5 μm and 15 μm, inclusive; (iii) the image object comprises an area of between or between about 65 μm$^2$ and 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, an image object is more than two non-cell particles if: (i) the image object comprises a circularity of less than about 0.4; (ii) the image object comprises a diameter of more than about 15 μm; (iii) the image object comprises an area of more than about 130 μm$^2$; (iv) the image object comprises a fluorescent signal, optionally above a background signal in a control sample; and/or (v) the image object comprises a florescent intensity (FI), optionally wherein the FI is greater than a background signal in a control sample. In some embodiments, the fluorescent intensity is the mean fluorescent intensity.

In some embodiments, the number of non-cell particles is enumerated by determining the number of single non-cell particles and the number of non-single non-cell particles, e.g., doublets or other multiples of non-cell particles. In some embodiments, the number of non-cell particles is enumerated by adding together the number of single non-cell particles and the number of non-single non-cell particles, e.g., doublets or other multiples of non-cell particles. In some embodiments, the number of non-cell particles is enumerated by determining the number of single non-cell particles and the number of double non-cell particles. In some embodiments, the number of double non-cell particles is multiplied by two to determine the number of single non-cell particles represented by the number of double non-cell particles. In some embodiments, the number of non-cell particles is enumerated by adding together the number of single non-cell particles and the number of double non-cell particles multiplied by two.

In some embodiments, the absence or presence of particles in a particular composition can be detected by method or technique such as by Western blot, flow cytometry (e.g., FACS), or microscopy (e.g., fluorescent microscopy). In some embodiments, the binding agent allows for the enumeration or determining of the number and/or concentration of particles by methods or techniques such as Western blot, flow cytometry (e.g., FACS), or microscopy (e.g., fluorescent microscopy).

In some embodiments, the methods provided herein involve determining the presence, absence, number, and/or concentration of particles in an output composition by particle (e.g., bead particle) counting by fluorescence activated cell sorting (FACS) using a flow cytometry device (e.g., Beckman Coulter Z2 Coulter Counter, Beckman Coulter Inc.). In some of the embodiments herein, FACS allows for detection of particles by detection of fluorescence of the particle (e.g., autofluorescence) or any detectable reagent or moiety present on the surface of the particles. In some embodiments, a FACS based method comprises the step of preparing the output composition for detection by flow cytometry before the presence, absence, number and/or concentration of particles can be determined. For example, the output composition can analyzed using a flow cytometer without the addition of any additional detectable reagents and/or moiety. In some embodiments, an additional detectable reagent or moiety is added, e.g., fluorescent label or fluorescently labeled antibody. In flow cytometry, cells and/or particles bound by fluorescently labeled affinity reagents are carried in a fluidic stream, are separated based on size and/or fluorescent signal and are subsequently analyzed and counted using a FACS software program (e.g., FlowJo software). The number or approximate number of particles can be determined by detection of the fluorescent signal, which optionally can be determined or processed by the FACS software program to provide the total or approximate number of particles in the output composition.

In some embodiments, other methods for determining or assessing particles in a sample can be employed. In some embodiments, the methods provided herein involve determining the presence, absence, number, and/or concentration of particles in an output composition by detection of particles using an automated cell counter (e.g., TC10 automated cell counter, Bio-Rad Laboratories Inc.). Such a method can further comprise the step of preparing the output composition for detection by an automated cell counter before the presence, absence, number and/or concentration of particles can be determined.

In some embodiments, the methods provided herein involve determining the presence, absence, number, and/or concentration of particles in an output composition by detection of particles using a hemocytometer (e.g., Hausser Nageotte Bright-Line™ Hemocytometer, Fischer Scientific), such as fitted to a microscope (e.g., Olympus IX70 inverted microscope). In some embodiments, such a method further comprises the step of preparing the output composition for detection before the presence, absence, number and/or concentration of particles can be determined. In some embodiments, particles present in a grid or region of a hemocytometer field can be visualized and/or counted, which, in some cases, can be performed manually. As an example, an exemplary hemocytometer is the Hausser Nageotte Bright-Line™ Hemocytometer, which contains approximately 40 rectangles and holds approximately a total of or about 50 µL liquid. Particles that are visualized in the 40 rectangles, including particles touching the rectangle lines, of the hemocytometer grid can be counted to obtain a particle count.

In some embodiments, counting can be repeated a plurality of times, such as two times, three times, four times, five times or more from an aliquot volume of the same sample (e.g. output composition) and the plurality of counts can be averaged and a standard deviation can be determined. In some embodiments, the number of particles per 0_, of the output composition can be calculated by dividing the averaged particle counts by the total volume of the sample added to the hemocytometer (e.g. 50 µL). In some embodiments, the average, standard deviation and coefficient of variation (100×(standard deviation/average)) of total particles (e.g., bead particles) per cell composition can be calculated from at least three replicate samples. In some embodiments, the number of particles per µL of the output composition can be calculated as described in Example 1.

In some embodiments, from the number or concentration of particles as determined in the output composition, the method further includes calculating the presence, absence, number, and/or concentration of particles in the cell composition from which the sample before lysis was derived or obtained. In some embodiments, to calculate the number of total particles (e.g., bead particles) in the cell composition from which the sample was derived or obtained, the concentration of particles (e.g. number of particles per µL) as determined to be present in the output composition can be multiplied by the volume of the cell composition from which the sample was obtained or derived prior to performing the lysis methods.

In some embodiments, the methods involve incubation of the output composition with an additional detectable reagent or moiety. In some embodiments, the output composition is incubated with a reagent that detects the particles. In some embodiments, fluorescence-based method or technique can be used to detect and/or enumerate the particles of the methods described herein. In some aspects, the provided methods do not alter or substantially alter any materials, moieties or molecules attached to, present or otherwise associated with the particles, thereby permitting direct or indirect detection of such materials, moieties or molecules using a binding agent (e.g. antibody, ligand or other binding molecule) that specifically binds or recognizes such material, moiety or molecule. In some embodiments, the binding agent is an antibody or an antigen-binding fragment thereof. For example, the binding agent may be an antibody or antigen-binding fragment thereof that recognizes a material on the particle (e.g., polymer) on the coating of a particle, an affinity reagent (e.g. antibody) attached to a particle or other material or moiety present on and/or associated with the particle. In some embodiments, the extent or level of detection by the binding agent of a material on or associated with the particle and/or an affinity reagent attached to the particle in particles of an output composition, on average, is at least or about at least 50%, 60%, 70%, 75%, 80%, 85%, 90%, 95% or more the extent or level of detection of the same material or affinity reagent by the binding agent, on average, in a reference composition that comprises substantially the same or the same particles but that was not exposed or subjected to the one or more incubations in accord with the provided methods. In some embodiments, the extent or level of detection by a binding agent of a material on or associated with the particle and/or an affinity reagent attached to the particle in particles of an output composition, on average, is about or about at least 2-fold, 3-fold, 4-fold, 5-fold, 6-fold, 7-fold, 8-fold, 9-fold, 10-fold, 20-fold, 30-fold, 40-fold, 50-fold or more greater than the extent or level of detection of the same material or affinity reagent by the binding agent, on average, in a reference composition comprising substantially the same or the same particles but that has been treated with bleach instead of subjected to the one or more incubations in accord with the provided method.

In some embodiments, the binding agent binds to a polymer, a polysaccharide, a silica, a fatty acid, and/or a carbon on the particle, such as on the coating of the particle. In some embodiments, the binding agent can be an antibody or antigen-binding fragment thereof that binds to the polymer present on the particle coat. In some embodiments, the binding agent binds to an affinity reagent conjugated, linked and/or coupled to the particle, such as to an affinity reagent conjugated, linked and/or coupled to the coating of the particle. In some embodiments, the affinity reagent is a nucleic acid (e.g., DNA), protein, antibody or antigen-binding fragment thereof, antigen, or any other molecules such as affinity reagents as described herein.

In some embodiments, the binding agent can be one that detects an affinity reagent attached to the particle. In some embodiments, the affinity reagent is an antibody (e.g. anti-CD3 and/or anti-CD28 antibody or other as described herein or known). In some embodiments, the binding agent for detecting the affinity reagent (e.g. antibody) is an anti-idiotypic antibody against an antibody on the surface of the particle. In some embodiments, the binding agent for detecting the affinity reagent (e.g. antibody) is an anti-isotypic antibody against a class, subclass, type or subtype of the heavy or light chain of the antibody. In some embodiments, the binding agent is an antibody that recognizes or specifically binds an IgG class, such as directed against IgG1, IgG2a, IgG2b, IgG3 or IgG4. In some embodiments, the affinity reagent is an antibody that is a mouse, rabbit, rat, goat, sheep, donkey or human antibody and the binding agent recognizes such species (e.g. the affinity reagent is a mouse antibody and the affinity reagent is an anti-mouse IgG1, anti-mouse IgG2a, etc.).

In some embodiments, the binding agent may be labeled such as with a florescent dye, a fluorescent protein, a gold particle, a silver particle, particles with different scattering spectra as compared to the particles in the output composition, polypeptides (e.g., FLAG™ tag, human influenza hemagglutinin (HA) tag, etc.), enzymes, streptavidin, biotin, chemiluminescent substrates, and other labels well known the art that are used for visualizing or detecting an affinity reagent bound to its target.

In some embodiments, provided is a method of enumerating or detecting the presence or absence of particles in a cell composition, wherein the method comprises the steps determining the presence, absence, number and/or concentration of particles in the output composition using a binding agent that specifically binds to the material on surface of the particle (e.g. polymer) and/or an affinity reagent attached to the particle, thereby enumerating or detecting the presence or absence of particles in the cell composition. In some embodiments, the binding agent is an antibody or antigen-binding fragment thereof. In some embodiments, the particle comprises a coat containing a polymer and the binding agent is an antibody that recognizes the polymer. In some embodiments, the particle comprises a coat containing an antibody (e.g., mouse antibody) and the binding agent is an antibody (e.g., anti-mouse antibody). In some embodiments, the particle comprises a coat containing streptavidin and the binding agent is an anti-streptavidin antibody or a biotinylated molecule.

As an example of the one or more processing steps, the output composition may comprise particles, wherein one or more of the particles further comprises a coat that contains a polymer and/or one or more affinity reagents (e.g., antibody) against a cell surface protein (e.g. anti-CD3, anti-CD28 or other antibody). In some embodiments, the output composition is washed and/or centrifuged to remove or reduce cell debris. The output composition may subsequently be incubated with a binding agent (e.g., fluorescently labeled antibody) that recognizes a polymer and/or a binding agent (e.g. fluorescently labeled anti-isotypic antibody) that recognizes an antibody (e.g. anti-CD3 or anti-CD28) under a condition sufficient to allow the binding agent to bind the polymer or affinity reagent. The output composition can be incubated with a blocking solution, such as a solution comprising a protein such as human serum albumin. In some cases, the blocking solution aids in preventing non-specific binding by the binding agent to other components of the cell composition. In some embodiments, the output composition may be incubated with the blocking solution, prior to, concurrently with or subsequently to the incubation with the binding agent. The output composition may be further washed and/or centrifuged to remove excess binding agent and/or binding agent that is not specifically bound to the polymer or affinity reagent on the particle. The output composition may be washed a plurality of times, such as two, three, four times or more.

III. Methods of Processing Cells in the Presence of Particles and Cell Compositions Containing Particles In some aspects, the provided methods can be used to detect the presence or absence of non-cell particles, e.g. bead particles, in a cell composition. In some embodiments, the sample used in the methods provided herein comprises at least a portion of a cell composition or is derived from a cell composition. In some aspects, the cell compositions can contain cells, e.g., T cells, engineered to express a recombinant receptor for administration to a subject for adoptive cell therapy. In some aspects, the engineered cells can be generated using process that involves incubation of cells with non-cell particles, e.g. bead particles, for stimulation and/or for enrichment of particular cells in the cell composition. In some aspects, the process also involves removal of such non-cell particles, e.g. bead particles, after incubation. In some aspects, the provided automated methods can be used to enumerate residual non-cell particles, e.g. beads, that are present in the cell composition, such as beads that remain in the sample after removal steps. In some cases, the provided method can be used to determine the efficiency of removal of the non-cell particles, e.g. bead particles, and to reduce adverse or toxic effects that can result from incomplete removal of the bead particles.

In some embodiments, the provided methods can be used for determining the presence, absence, number and/or concentration of particles (e.g., microspheres or bead particles) in a sample that is derived from or obtained from a cell composition. In some embodiments, the cell composition can be a pharmaceutical composition and/or formulated for administration to a subject. In some embodiments, the sample contains at least a portion of the cell composition. In some embodiments, the sample that is assessed for the presence, absence, number and/or concentration of particles includes or is a portion of the cell composition. In some embodiments, the sample represents no more than 0.1%, 0.25%, 0.5%, 0.75%, 1%, 1.5%, 2%, 2.5%, 5.0%, 10.0%, 20.0%, 30.0%, 40.0%, or 50.0% of the cell composition.

In some embodiments, the cell composition can be a cell preparation that has been processed in the presence of one or more particles (such as one or more microspheres or bead particles), such as for enrichment, separation, selection, isolation, stimulation, activation and/or expansion of one or more cells in a population of cells. In some embodiments, one or more particles (e.g., microspheres or bead particles) are mixed with cells, such as by incubating or contacting particles with a population of cells, thereby producing a cell composition. In some embodiments, the one or more particles are capable of binding one or more cells in the population. In some embodiments, the processing produces a cell composition that contains or potentially contains one or more cells specifically associated or that had been specifically associated with one or more particles (e.g., microspheres or bead particles) and still present or potentially present in the cell composition.

In some embodiments, the mixing, such as incubating or contacting, of the particles (e.g., microspheres or bead particles) with a population of cells facilitates or results in enrichment, separation, selection, isolation, activation, stimulation and/or expansion of cells in the population. In some embodiments, typically, the enrichment, separation, selection, isolation, activation, stimulation and/or expansion is achieved due to the presence of one or more biomolecules, such as one or more affinity reagents (e.g. protein, such as an antibody) present on the surface of the particles (e.g., microspheres or bead particles) that specifically interact with, such as bind or engage, one or more macromolecules (e.g., cell surface receptor) on the surface of one or more cells in the cell population. In some embodiments, presentation of the biomolecule, e.g. affinity reagent, on the particle can create a multivalent ligand in which several macromolecules on a cell or cells can bind or engage with an affinity reagent present on the particle. In some embodiments, the cell composition is processed by removal of one or more particles from the mixture containing the cells and the particles.

In some embodiments, the processing produces a cell composition containing or potentially containing one or more cells specifically associated, or that had been specifically associated, with one or more particles, for example, via the specific interaction between the affinity reagent on the particle (e.g. microsphere or bead particle) and the macromolecule on the surface of the cell. In some embodiments, cell compositions, such as therapeutic cell compositions, are processed as described herein, including by incubation with one or more non-cell particles and further by removing the one or more particles. In some embodiments, the cell composition is produced by a method comprising mixing a population of cells with one or more particles to produce an input composition that is further processed by removing one or more of the particles from the cells. In some embodiments, the described methods, kits and reagents can be used to assess the presence or absence of residual particles present in the processed cell compositions. In some embodiments, the cell compositions, e.g., therapeutic cell compositions, can be assessed using the methods described herein.

In some embodiments, an input composition comprises one or more cells and one or more non-cell particles. In some embodiments, an input composition comprises one or more cells and one or more non-cell particles. In some embodiments, an input composition is produced from mixing a population of cells with one or more particles, e.g., can be an intermediate composition in the cell engineering process.

In some embodiments, an input composition comprises at least a portion of the cell compositions described herein, or at least a portion of one stage of the cell composition during the engineering process. In some embodiments, the input composition is an intermediate composition produced during the engineering process of cells in a cell composition.

In some aspects, a sample comprising at least a portion of an input composition or a sample derived from the input composition is used in connection with the methods provided herein, e.g., are subject to incubation to induce lysis to generate an output composition, which is then analyzed and assessed by fluorescence imaging and/or other analysis methods. In some embodiments, the sample used in the methods provided herein is at least a portion of the input composition or is derived from the input composition.

In some embodiments, the input composition derived from a composition containing one or more cells bound to one or more of the non-cell particles further processed by removing one or more of the non-cell particles. In some embodiments, the input composition is a composition that had been subject to removal of the particles, therefore is thought to be free of or substantially free of particles. In some aspects, the removal process does not completely remove all of the particles in the composition, and the input composition may contain residual particles. Thus, in some embodiments, the input composition is a composition for testing the presence or absence of residual particles, using the methods provided herein; and a sample is obtained or derived from the input composition. In some embodiments, the input composition comprises or is suspected of comprising one or more of the non-cell particles bound to, or that had been bound to, the surface of one or more cells in the input composition such as following incubation with one or more non-cell particles, in which such one or more non-cell particles is present in a composition with the one or more cells. In some embodiments, the input composition comprises or is suspected of comprising residual particles following a step of removing or reducing non-cell particles from a cell composition in which it is not known or it is likely or suspected that some particles may remain in the composition with the one or more cells. In some embodiments, the input composition is derived from a cell composition containing one or more cells and one or more non-cell particles, in which such one or more cells is bound to, or had been bound to, one or more of the non-cell particles. In some embodiments, the input composition is derived from a cell composition containing one or more cells and one or more non-cell particles, in which such one or more cells is bound to, or had been bound to, one or more of the non-cell particles, in which such cell composition had been further processed by a step to remove or reduce one or more of the non-cell particles from the cell composition.

In some embodiments, the cell composition is a cell preparation that has been processed in the presence of one or more particles and is further subjected to one or more steps for removal of the particles from the cell preparation. In some cases, the removal of particles is incomplete or it is otherwise not known if the removal of particles is complete, and the resulting cell composition contains or may contain residual particles. In some embodiments, a cell composition provided herein comprises or is suspected of comprising residual particles.

In some embodiments, the particle (e.g., bead particle) to cell ratio in a cell composition provided herein, such as for stimulation and/or expansion of a cell or a cell population, is about any of 1:1, 1:2, 1:3, 1:4, 1:5, 1:6, 1:7, 1:8, 1:9, 1:10, 1:12, 1:14; 1:16, 1:18, 1:20, 1:25, 1:30, 1:35, 1:40, 1:45, 1:50, 2:1, 2:2, 2:3, 2:4, 2:5, 2:6, 2:7, 2:8, 2:9, 2:10, 3:1, 3:2, 3:3, 3:4, 3:5, 3:6, 3:7, 3:8, 3:9, 3:10, 4:1, 4:2, 4:3, 4:4, 4:5, 4:6, 4:7, 4:8, 4:9, 4:10, 5:1, 5:2, 5:3, 5:4, 5:5, 5:6, 5:7, 5:8, 5:9, 5:10, 6:1, 6:2, 6:3, 6:4, 6:5, 6:6, 6:7, 6:8, 6:9, 6:10, 7:1, 7:2, 7:3, 7:4, 7:5, 7:6, 7:7, 7:8, 7:9, 7:10, 8:1, 8:2, 8:3, 8:4, 8:5, 8:6, 8:7, 8:8, 8:9, 8:10, 9:1, 9:2, 9:3, 9:4, 9:5, 9:6, 9:7, 9:8, 9:9, 9:10, 10:1, 10:2, 10:3, 10:4, 10:5, 10:6, 10:7, 10:8, 10:9, or 10:10. In some embodiments, the particle (e.g., bead particle) to cell ratio in a composition provided herein (e.g., for stimulation and/or expansion of a cell or a cell population) is about 1:1, about 1:2, about 1:10, about 4:1, or about 3:1.

In some embodiments, the cell composition comprises a plurality of particles with the same size (e.g., the same diameter). In some embodiments, the cell composition comprises a plurality of particles with at least two different sizes. For example, the cell composition may comprise one or more particles with a diameter of about 3 µm, one or more particles with a diameter of about 4 µm, one or more particles with a diameter of about 5 µm, one or more particles with a diameter of about 6 µm, one or more particles with a diameter of about 7 µm, one or more particles with a diameter of about 8 µm, one or more particles with a diameter of about 9 µm, one or more particles with a diameter of about 10 µm, one or more particles with a diameter of about 11 µm, one or more particles with a diameter of about 12 µm, one or more particles with a diameter of about 13 µm, one or more particles with a diameter of about 14 µm and/or one or more particles with a diameter of about 15 µm.

In some embodiments, the size of a cell in the cell composition is about 1.0 µm to about 30 µm, about 1.0 µm to about 25 µm, about 1.0 µm to about 20 µm, about 1.0 µm to about 15 µm, about 1.0 µm to about 10 µm, about 1.0 µm to about 5.0 µm, about 10 µm to about 15 µm, about 6 µm to about 12 µm, or about 7 µm to about 8 µm. In some embodiments, the size of the at least one cell is about at least or is at least 1 µm, 1.5 µm, 2.0 µm, 2.5 µm, 3.0 µm, 3.5 µm, 4.0 µm, 4.5 µm, 5.0 µm, 5.5 µm, 6.0 µm, 6.5 µm, 7.0 µm, 7.5 µm, 8.0 µm, 8.5 µm, 9.0 µm, 9.5 µm, 10 µm, 11 µm, 12 µm, 13 µm, 14 µm, 15 µm, 16 µm, 17 µm, 18 µm, 19 µm, 20 µm, 21 inn, 22 µm, 23 µm, 24 µm, or 25 µm.

In some embodiments, a concentration of cells in a cell composition or a sample obtained from or derived from the cell composition or an input composition is at least about $2\times10^5$ cells/mL, at least about $5\times10^5$ cells/mL, at least about $1\times10^6$ cells/mL, at least about $2.5\times10^6$ cells/mL, at least about $5\times10^6$ cells/mL, at least about $1\times10^7$ cells/mL, at least about $5\times10^7$ cells/mL, at least about $1\times10^8$ cells/mL, or at least about $5\times10^8$ cells/mL. In some embodiments, the concentration of the cells in the sample, cell composition or input composition is at least or at least about $2\times10^5$ cells/mL, at least or at least about $5\times10^5$ cells/mL, at least or at least about $1\times10^6$ cells/mL, at least or at least about $5\times10^6$ cells/mL, at least or at least about $1\times10^7$ cells/mL, at least or at least about $5\times10^7$ cells/mL, at least or at least about $1\times10^8$ cells/mL or at least or at least about $5\times10^7$ cells/mL. In some embodiments, the concentration of the cells in the sample, cell composition or input composition is between or between about $1\times10^2$ cells/mL and $1\times10^8$ cells, such as $1\times10^4$ cells/mL to $1\times10^8$ cells/mL, $1\times10^4$ cells/mL to $1\times10^7$ cells/mL, or $1\times10^6$ cells/mL to $7\times10^7$ cells/mL. In some embodiments, the concentration of the cells in the sample, cell composition or input composition is greater than or greater than about $10\times10^6$ cells, greater than or greater than about $15\times10^6$ cells, greater than or greater than about $25\times10^6$ cells. In some embodiments, the concentration of the cells in the sample, cell composition or input composition is between about 10 million cells per mL and about 70 million cells per mL, between about 10 million cells per mL and about 50 million cells per mL, between about 10 million cells per mL and about 25 million cells per mL, between about 10 million cells per mL and about 15 million cells per mL, 15 million cells per mL and about 70 million cells per mL, between about 15 million cells per mL and about 50 million cells per mL, between about 15 million cells per mL and about 25 million cells per mL, between about 25 million cells per mL and about 70 million cells per mL, between about 25 million cells per mL and about 50 million cells per mL, and between about 50 million cells per mL and about 70 million cells per mL. In some aspects, the condition for lysis is sufficient to induce lysis of some or all of the cells in the sample containing any of the described cell concentrations.

In some embodiments, the volume of the input composition or a sample obtained or derived from the input composition described herein is from any of about 0.2 mL to 50 mL, 0.2 mL to 20 mL, 0.5 mL to 10 mL, 0.5 mL to 5 mL, or 0.75 mL to 1.5 mL. In some embodiments, the volume of the cell composition or a sample obtained or derived from the cell composition described herein is at least about or is at least 0.2 mL, about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, about 1.5 mL, about 1.6 mL, about 1.7 mL, about 1.8 mL, about 1.9 mL, about 2.0 mL, about 5.0 mL, about 10.0 mL, about 20 mL, or about 50 mL but no more than 100 mL.

A. Non-Cell Particles, e.g., Bead Particles

In some embodiments, the cells are incubated with or contacted with one or more particles (one or more non-cell particles). In some cases, a particle described herein (e.g., bead particle) provides a solid support or matrix to which a biomolecule, such as an affinity reagent, such as an affinity reagent described herein (e.g., an antibody), can be bound, thereby facilitating separation, enrichment, selection, isolation, activation, stimulation and/or expansion of one more cell types in a cell population based on expression or expression level of one or more macromolecule on the surface of a cell, e.g. cell surface protein. In some embodiments, the cells can be incubated or contacted with a particle, which typically is conjugated or linked to a biomolecule, such as an affinity reagent, that is capable of specifically binding to a macromolecule on the surface of a cell. In some embodiments, the particle is or comprises a solid surface. In some embodiments, the particle is a bead particle. In some embodiments, the particle is an autofluorescent particle. In some embodiments, the autofluorescent particle can be detected and analyzed, e.g., using fluorescence imaging to determine presence, absence, number, and/or concentration of particles (e.g. microspheres or bead particles) present in the sample obtained and/or derived from a cell composition.

In some embodiments, the particle is an autofluorescent particle. In some embodiments, the one or more non-cell particles comprises autofluorescent bead particles. In some embodiments, the particle is autofluorescent. In some aspects, the autofluorescence of a non-cell particles can be detected at a wavelength of at between about 650 nm and about 700 nm. In some embodiments of any of the provided embodiments, the autofluorescence of one or more non-cell particles can be detected at a wavelength of at about 685 nm. In some embodiments, autofluorescent particles can be detected by their natural emission of light when they have absorbed light, e.g., light from a light source from a fluorescent imaging apparatus such as a microscope or a fluorescent plate reader. In some embodiments, the autofluorescent particles can be detected without the addition of any additional detectable reagent or moiety for detecting the one or more non-cell particles. In some aspects, the provided embodiments offer an advantage that the additional reagents are not required for detection of the particles, reducing the cost and time required for assessment and/or reducing experimental variation and/or operator variation.

In some embodiments, the one or more non-cell particles do not comprise an additional detectable reagent or moiety, e.g., does not comprise an additional fluorescent label. In some embodiments, the one or more non-cell particles are autofluorescent, but are not additionally contacted with or incubated with using a different additional detectable reagent or moiety, prior to performing the analysis step.

In some embodiments, the particle can be a composite particle containing an inner core. In some embodiments, the inner core is a magnetic core, a paramagnetic core or a superparamagnetic core. In some embodiments, the inner core (e.g., magnetic core) is or contains any suitable metal. In some embodiments, the metal can be, but is not limited to, iron, nickel, copper, cobalt, gadolinium, manganese, tantalum, zinc, zirconium or any combinations thereof. Suitable substances that may be included in an inner core described herein (e.g., a magnetic core) includes, but is not limited to, metal oxides (e.g., iron oxides), ferrites (e.g., manganese ferrites, cobalt ferrites, nickel ferrites, etc.), hematite and metal alloys (e.g., CoTaZr). In some embodiments, the inner core comprises one or more of a ferrite, a metal, a metal alloy, an iron oxide, or chromium dioxide. In some embodiments, the inner core comprises elemental iron or a compound thereof. In some embodiments, the inner core comprises one or more of magnetite ($Fe_3O_4$), maghemite ($\gamma Fe_2O_3$), or greigite ($Fe_3S_4$). In some embodiments, the inner core comprises an iron oxide (e.g., $Fe_3O_4$). In some embodiments, the inner core comprises colloidal iron (e.g., colloidal iron oxide).

In some embodiments, the particle (e.g., bead particle) reacts in a magnetic field. In some embodiments, the particle is a magnetic particle (e.g., magnetic bead particle).

In some embodiments, the inner core can further contain a polymer, a polysaccharide, a silica, a fatty acid, a protein, a carbon or a combination thereof. In some embodiments, the polymer is one or more selected from the group consisting of: a polyethylene glycol, poly(lactic-co-glycolic acid), polyglutaraldehyde, polyurethane, polystyrene, cyclo-olefin polymer (COP) and polyvinyl alcohol. In some embodiments, the polymer is polystyrene. In some embodiments, the polymer is polyglutaraldehyde. In some embodiments, the polymer is a biodegradable polymer. In some embodiments, the polysaccharide can be chitosan, agarose, starch, dextran, or a dextran derivative. In some embodiments, the silica is silicon oxide. In some embodiments, the protein is an albumin (e.g., human serum albumin). In some embodiments, the carbon is one or more selected from the group consisting of: an acrylamide and maleic acid. In some embodiments, the inner core comprises a metal oxide (e.g., an iron oxide) and a polymer (e.g., polystyrene). In some embodiments, the inner core comprises colloidal iron (e.g., colloidal iron oxide) and a polymer (e.g., polystyrene).

In some embodiments, the inner core comprises nanoparticles. In some embodiments, the inner core comprises microbeads. Such nanoparticles or microbeads can each have their own inner core comprising a metal and/or polymer described herein and, optionally further comprise a coat such as a coat described herein. In some embodiments, an inner core described herein comprises nanoparticles and a polymer (e.g., silica). In some embodiments, an inner core described herein comprises microbeads and a polymer (e.g., silica).

In some the embodiments, an inner core described herein has a diameter of less than about 3000 nm, about 2000 nm, about 1000 nm, about 900 nm, about 800 nm, about 700 nm, about 600 nm, about 500 nm, about 400 nm, about 300 nm, about 200 nm, about 100 nm, about 90 nm, about 80 nm, about 70 nm, about 60 nm, about 50 nm, about 40 nm, about 30 nm, about 20 nm, or about 10 nm. In some the embodiments, the inner core has a diameter of about any of 3000 nm, about 2000 nm, about 1000 nm, about 900 nm, about 800 nm, about 700 nm, about 600 nm, about 500 nm, about 400 nm, about 300 nm, about 200 nm, about 100 nm, about 90 nm, about 80 nm, about 70 nm, about 60 nm, about 50 nm, about 40 nm, about 30 nm, about 20 nm, or about 10 nm. In some embodiments, the inner core has a diameter of about 100 nm or less. In some embodiments, the inner core has a diameter of about 50 nm or less.

In some of the embodiments, the particle can further contain one or more coat or coating such as one or more coat or coating on a surface of the particle (e.g., surface coating). In some embodiments, one or more coat or coating protects the inner core, provides a material for conjugation or coupling to an affinity reagent and/or provides a biodegradable surface.

In some embodiments, a coat or coating (e.g., surface coating) described herein provides a protective coat. In some embodiments, the coat (e.g., protective coat) or coating (e.g., protective coating) protects, reduces or prevents oxidation of an inner core (e.g., magnetic core). For example, the coat may protect, reduce or prevent the magnetic core from oxidation. In some embodiments, the coat or coating retains an inner core to the particle (e.g., bead particle). In some embodiments, the coat or coating prevents deterioration of an inner core. In some embodiments, the particle, e.g., bead particle, is inert. In some embodiments, the coat (e.g., protective coat) or coating (e.g., protective coating) protects, renders the particle (e.g., bead particle) inert.

In some embodiments, the coat contains at least one material that can be coupled, linked or conjugated to an affinity reagent. In some embodiments, the material can be coupled, linked or conjugated to one or more affinity reagent such as a nucleic acid (e.g., DNA), protein, antibody, antigen, or any other affinity reagent for a desired target (e.g., T cells).

In some embodiments, the coat can contain a material that can include, but is not limited to, a polymer, a polysaccharide, a silica, a fatty acid, a protein, a carbon, or a combination thereof. In some embodiments, the polymer can be a polyethylene glycol, poly(lactic-co-glycolic acid), polyglutaraldehyde, polyurethane, polystyrene, cyclo-olefin polymer (COP), polycarbonate (PC), poly(methyl methacrylate) (PMMA), poly(dimethylsiloxane) (PDMS), cyclo-olefin copolymer (COC) or a polyvinyl alcohol. In some embodiments, the polymer is polystyrene.

In some embodiments, the coat can contain a material that can include, but is not limited to, a polysaccharide, a silica, a fatty acid, a protein or a combination thereof. In some embodiments, the polymer is a biodegradable polymer. In some embodiments, the polysaccharide can be chitosan, agarose, starch, dextran, or a dextran derivative. In some embodiments, the silica is silicon oxide. In some embodiments, the silica is silicon oxide. Methods of producing silicon oxide for coating an inner core are well known. See U.S. Pat. No. 8,398,741. In some embodiments, the coat contains or includes a material that is or includes a protein that is an albumin (e.g., human serum albumin), Protein A, and Protein G. In some embodiments, the carbon is an acrylamide or maleic acid. In some embodiments, the material is coupled, linked or conjugated to an affinity reagent described herein.

In some embodiments, the coat can contain a polymer. In some embodiments, the polymer is one or more selected from the group consisting of: a polyethylene glycol, poly (lactic-co-glycolic acid), polyglutaraldehyde, polyurethane, polystyrene, cyclo-olefin polymer (COP), polycarbonate (PC), poly(methyl methacrylate) (PMMA), poly(dimethylsiloxane) (PDMS), cyclo-olefin copolymer (COC), and polyvinyl alcohol. In some embodiments, the polymer is a thermoplastic. In some embodiments, the polymer is a biocompatible polymer. In some embodiments, the polymer renders the particle containing and/or coated with the polymer autofluorescent (see, e.g., Young et al., (2013) Anal Chem. 85(1): 44-49). In some embodiments, the polymer is polystyrene.

In some embodiments, a coat or coating described herein (e.g., a protective coat) has a thickness of less than about 500 nm, less than about 450 nm, less than about 400 nm, less than about 350 nm, less than about 300 nm, less than about 250 nm, less than about 200 nm, less than about 150 nm, less than about 100 nm, less than about 75 nm, less than about 50 nm, or less than about 25 nm. In some embodiments, a coat or coating described herein (e.g., a protective coat) has a thickness of about 500 nm, about 450 nm, about 400 nm, about 350 nm, about 300 nm, about 250 nm, about 200 nm, about 150 nm, about 100 nm, about 75 nm, about 50 nm, or about 25 nm.

In some embodiments, a particle described herein (e.g., a bead particle) can have an inner core and a coat (e.g., protective coat) wherein the coat contains one or more material described herein. In some embodiments, a particle described herein (e.g., a bead particle) comprises a metal oxide core (e.g., an iron oxide inner core) and a coat (e.g., a protective coat), wherein the coat comprises at least one polymer. In some embodiments, a particle described herein (e.g., a bead particle) comprises a metal oxide core (e.g., an iron oxide inner core) and a coat (e.g., a protective coat), wherein the coat comprises at least one polymer (e.g., polystyrene). In some embodiments, a particle described herein (e.g., a bead particle) has a metal oxide core (e.g., an iron oxide inner core) and a coat (e.g., a protective coat), wherein the coat comprises at least one polymer (e.g., polystyrene) and silica. In some of any such embodiments herein, the metal oxide core is an iron oxide core comprising colloidal iron (e.g., colloidal iron oxide inner core). In some of any such embodiments herein, the metal oxide core comprises a polymer and colloidal iron. In some of any such embodiments, the coat has a thickness of about 400 nm.

In some of the embodiments herein, the particle (e.g., bead particle) has a diameter of greater than about 0.001 μm, greater than about 0.01 μm, greater than about 0.1 μm, greater than about 1.0 μm, greater than about 10 μm, greater than about 50 μm, greater than about 100 μm or greater than about 1000 μm and no more than about 1500 μm. In some embodiments, the particle (e.g., bead particle) has a diameter of about 1.0 μm to about 500 μm, about 1.0 μm to about 150 μm, about 1.0 μm to about 30 μm, about 1.0 μm to about 10 μm, about 1.0 μm to about 5.0 μm, about 2.0 μm to about 5.0 μm, or about 3.0 μm to about 5.0 μm. In some embodiments, the particle (e.g., bead particle) has a diameter of about 3 μm to about 5 μm. In some embodiments, the particle (e.g., bead particle) has a diameter of at least or at least about or about 0.001 μm, 0.01 μm, 0.1 μm, 0.5 μm, 1.0 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 10 μm, 12 μm, 14 μm, 16 μm, 18 μm or 20 μm.

In some embodiments, the particle (e.g., bead particle) has a diameter that is greater than about 1.5-fold, greater than about 2-fold, greater than about 3-fold, greater than about 4-fold, or greater than about 5-fold the diameter of the cell and no more than 10-fold the diameter of a cell in a cell composition or sample described herein. In some embodiments, the particle (e.g., bead particle) has a diameter that is less than 1.5-fold, less than 2-fold, less than 3-fold, less than 4-fold, or less than 5-fold the diameter of a cell in a cell composition or sample described herein. In some embodiments, the particle (e.g., bead particle) is substantially the same or about the same size as a cell in a cell composition or sample described herein such as within 1.5-fold the size of the cell (greater or less than no more than 1.5-fold the size of the cell).

In some embodiments, the particle (e.g., bead particle) can further contain one or more biomolecule, such as an affinity reagent, such as one or more biomolecule, e.g. affinity reagent, that is coupled, conjugated or linked (directly or indirectly) to the coat or coating of the particle. In some embodiments, biomolecules, such as affinity reagents, contemplated herein can include, but are not limited to, RNA, DNA, proteins (e.g., enzymes), antigens, polyclonal antibodies, monoclonal antibodies, antibody fragments, carbohydrates, lipids lectins, or any other affinity reagent (e.g., streptavidin) with an affinity (e.g., affinity reagent) for a desired target. The one or more biomolecule, such as an affinity reagent, may be attached directly or indirectly to the particle (e.g., bead particle) by a variety of methods known and available. The attachment may be covalent, noncovalent, electrostatic, or hydrophobic and may be accomplished by a variety of attachment means, including for example, a chemical means, a mechanical means, or an enzymatic means. In some embodiments, an affinity reagent (e.g., biotinylated anti-CD3 antibody) may be attached indirectly to the particle via another affinity reagent (e.g., anti-biotin antibody) that is directly attached to the particle.

In some embodiments, the biomolecule is an affinity reagent that is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). In some embodiments, the affinity reagent is an antibody fragment (including antigen-binding fragment), e.g., a Fab, Fab'-SH, Fv, scFv, or (Fab')$_2$ fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species).

In some embodiments, the antibody is an anti-biotin antibody or an anti-IgG antibody. In some embodiments, the antibody or antigen-binding fragment thereof is biotinylated (e.g., biotinylated anti-CD3 antibody).

In some embodiments, the molecule, such as an affinity reagent, specifically binds to a target on a cell. In some embodiments, the target is one or more macromolecule on the surface of a cell. Cells contemplated herein include, but are not limited to, T cells (e.g., CD4+ T cells, CD8+ T cells, etc.), B cells (e.g., memory B cells, plasma B cells, etc.), natural killer cells, eosinophils, mast cells, basophils, macrophages, and dendritic cells.

In some cases, a particle described herein (e.g., bead particle) provides a solid support or matrix to which a biomolecule, such as an affinity reagent, such as an affinity reagent described herein (e.g., an antibody), can be bound, thereby facilitating separation, enrichment, selection, isolation, activation, stimulation and/or expansion of one more cell types in a cell population based on expression or expression level of one or more macromolecule on the surface of a cell, e.g. cell surface protein. Among biomolecules, such as affinity reagents, that can be employed, include, but are not limited to RNA, DNA, proteins (e.g., enzymes), antigens, polyclonal antibodies, monoclonal antibodies, antibody fragments, carbohydrates, lipids lectins, or any other affinity reagent (e.g., streptavidin) that is capable of specifically binding one or more macromolecule on the surface of a cell. In certain embodiments, the particle (e.g., a magnetic bead particle) comprises one or more biomolecule, such as an affinity reagent (e.g., an antibody) that binds directly or indirectly to one or more macromolecule on the surface of a cell.

In some embodiments, the particle comprises one or more affinity reagent that directly interact with a macromolecule on the surface of a cell. In certain embodiments, the particle (e.g., a magnetic bead particle) interacts with a cell via one or more affinity reagent (e.g., an antibody) specific for one or more macromolecules on the cell (e.g., one or more cell surface protein). In certain embodiments, the particle (e.g., a magnetic bead particle) is labeled with a first affinity reagent described herein, such as a primary antibody (e.g., an anti-biotin antibody) or other first affinity reagent, and then a second affinity reagent, such as a secondary antibody (e.g., a biotinylated anti-CD3 antibody) or other second affinity reagent (e.g., streptavidin), is added, whereby the secondary antibody or other second affinity reagent specifically binds to such primary antibodies or other first affinity reagent on the particle.

In some embodiments, the particle comprises an affinity reagent that indirectly interacts with a macromolecule on the surface of a cell. In certain embodiments, the cell, rather than a particle described herein (e.g., a magnetic bead particle), is labeled with one or more affinity reagent described herein. In certain embodiments, the cell is labeled with a first affinity reagent described herein, such as a primary antibody (e.g., a biotinylated anti-CD3 antibody) or other first affinity reagent (e.g., streptavidin), and then a particle carrying a second affinity reagent, such as a secondary antibody (e.g., an anti-biotin antibody) or other second affinity reagent, are added, whereby the secondary antibody or other second affinity reagent specifically binds to such primary antibodies or other first affinity reagent. In some embodiments, the one or more affinity reagent is an antibody. In some embodiments, the one or more affinity reagent is an anti-biotin antibody.

In some embodiments, an affinity reagent (e.g. antibody) attached to a particle (e.g., bead particle) specifically binds to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3 or fragment thereof including the corresponding ligands to these macromolecules or fragments thereof. In some embodiments, an affinity reagent (e.g. antibody) attached to a particle (e.g. bead particle) specifically binds to one or more of the following macromolecules on a cell (e.g. a T cell): CD28, CD62L, CCR7, CD27, CD127, CD3, CD4, CD8, CD45RA, and/or CD45RO.

In some embodiments, the affinity reagent delivers a signal to a cell or acts as stimulating agent. For example, an antibody or antigen-binding fragment thereof (e.g., Fab) that is attached to a particle (e.g., bead particle) can provide a stimulation signal to a cell (e.g., a T cell) and induce cell stimulation and/or cell expansion. Such antibodies contemplated herein include, but are not limited to, an anti-CD2 antibody, an anti-CD3 antibody, an anti-CD28 antibody, an anti-CD137 antibody, an anti-CD134 antibody, or combinations thereof including antigen-binding fragments thereof. In some embodiments, such antibodies or antigen-binding fragments thereof are biotinylated (e.g., biotinylated anti-CD3 antibody).

In some embodiments, the one or more affinity reagent is one or more antibody selected from the group consisting of: an anti-CD2 antibody, an anti-CD3 antibody, an anti-CD28 antibody, an anti-CD137 antibody, and an anti-CD134 antibody. In some embodiments, the one or more affinity reagent is an anti-CD3 antibody and an anti-CD28 antibody. In some embodiments, the one or more affinity reagent is an anti-CD2 antibody, an anti-CD3 antibody and an anti-CD28 antibody. In some embodiments, the one or more affinity reagent is an anti-CD2 antibody, an anti-CD3 antibody, anti-CD28 antibody, and an anti-biotin antibody. In some embodiments, the one or more affinity reagent is an anti-CD3 antibody, anti-CD28 antibody, and an anti-biotin antibody.

In some embodiments, the particle (e.g., bead particle) comprises a metal oxide core (e.g., an iron oxide core) and a coat, wherein the metal oxide core comprises at least one polymer, and wherein the coat comprises at least one polymer, at least one polymer (e.g., polystyrene) and silica. In some embodiments herein, the metal oxide core is a colloidal iron oxide core. In a further embodiment, the particle comprises one or more affinity reagent that binds to a macromolecule (e.g., protein) on the surface of a cell, thereby causing association or binding of the particle to the cell in the cell composition or a sample of the cell composition.

In some embodiments, the one or more biomolecule, such as an affinity reagent, is selected from the group consisting of: RNA, DNA, proteins, antigens, polyclonal antibodies, monoclonal antibodies, carbohydrates, lipids or any other affinity reagent (e.g., streptavidin) with an affinity (e.g., affinity reagent) for a desired target. In some embodiments, the affinity reagent is an antibody or antigen-binding fragment thereof. In some embodiments, the particle comprises an anti-CD3 antibody and an anti-CD28 antibody. In some embodiments, the particle comprises an anti-CD2 antibody, an anti-CD3 antibody and an anti-CD28 antibody. In some embodiments, the particle comprises an anti-CD2 antibody, an anti-CD3 antibody, anti-CD28 antibody, and an anti-biotin antibody. In some embodiments, the particle comprises an anti-CD3 antibody, anti-CD28 antibody, and an anti-biotin antibody. In some embodiments, the particle comprises an anti-biotin antibody. In some embodiments, the bead particle has a diameter of about 3 μm to about 10 μm. In some embodiments, the bead particle has a diameter of about 3 μm to about 5 μm.

The particles (e.g., bead particles) used in the methods described herein can be produced or obtained commercially. Particles, including methods of producing particles, are well known. See, for example, U.S. Pat. Nos. 6,074,884; 5,834,121; 5,395,688; 5,356,713; 5,318,797; 5,283,079; 5,232,782; 5,091,206; 4,774,265; 4,654,267; 4,554,088; 4,490,436; 4,452,773; U.S. Patent Application Publication No. 20100207051; and Sharpe, Pau T., Methods of Cell Separation, Elsevier, 1988. Commercially available particles (e.g., bead particles) include, but are not limited to, Pro-Mag™ (PolySciences, Inc.); COMPEL™ (PolySciences, Inc.); BioMag® (PolySciences, Inc.), including BioMag® Plus (PolySciences, Inc.) and BioMag® Maxi (Bang Laboratories, Inc.); M-PVA (Cehmagen Biopolymer Technologie AG); SiMAG (Chemicell GmbH); beadMAG (Chemicell GmbH); MagaPhase® (Cortex Biochem); Dynabeads® (Invitrogen), including Dynabeads® M-280 Sheep Anti-rabbit IgG (Invitrogen), Dynabeads® FlowComp™ (e.g., Dynabeads® FlowComp™ Human CD3, Invitrogen), Dynabeads® M-450 (e.g., Dynabeads® M-450 Tosylactivated, Invitrogen), Dynabeads® Untouched™ (e.g., Dynabeads® Untouched™ Human CD8 T Cells, Invitrogen), and Dynabeads® that bind, expand and/or activate T cells (e.g., Dynabeads® Human T-Activator CD3/CD28 for T Cell Expansion and Activation, Invitrogen); Estapor® M (Merk Chimie SAS); Estapor® EM (Merk Chimie SAS); MACSi-Beads™ Particles (e.g., anti-biotin MACSiBead Particles, Miltenyi Biotec, catalog #130-091-147); Streptamer® Magnetic Beads (IBA BioTAGnology); Strep-Tactin® Magnetic Beads (IBA BioTAGnology); Sicastar®-M (Micormod Partikeltechnologie GmbH) Micromer®-M (Micromod Partikeltechnologie); MagneSil™ (Promega GmbH); MGP (Roche Applied Science Inc.); Pierce™ Protein G Magnetic Beads (Thermo Fisher Scientific Inc.); Pierce™ Protein A Magnetic Beads (Thermo Fisher Scientific Inc.); Pierce™ Protein A/G Magnetic Beads (Thermo Fisher Scientific Inc.); Pierce™ NHS-Activated Magnetic Beads (Thermo Fisher Scientific Inc.); Pierce™ Protein L Magnetic Beads (Thermo Fisher Scientific Inc.); Pierce™ Anti-HA Magnetic Beads (Thermo Fisher Scientific Inc.); Pierce™ Anti-c-Myc Magnetic Beads (Thermo Fisher Scientific Inc.); Pierce™ Glutathione Magnetic Beads (Thermo Fisher Scientific Inc.); Pierce™ Streptavidin Magnetic Beads (Thermo Fisher Scientific Inc.); MagnaBind™ Magnetic Beads (Thermo Fisher Scientific Inc.); Sera-Mag™ Magnetic Beads (Thermo Fisher Scientific Inc.); Anti-FLAG® M2 Magnetic Beads (Sigma-Aldrich); SPHERO™ Magnetic Particles (Spherotech Inc.); and HisPur™ Ni-NTA Magnetic Beads (Thermo Fisher Scientific Inc.).

In some embodiments, the cells can be incubated and/or contacted with a stimulatory reagent that is capable of activating and/or expanding T cells. In certain embodiments, the stimulatory reagent comprises a particle, e.g., a bead, that is conjugated or linked to one or more agents, e.g., affinity reagents, that are capable of activating and/or expanding cells, e.g., T cells. In some embodiments, the one or more agents are bound to a bead. In some embodiments, the bead is biocompatible, i.e., composed of a material that is suitable for biological use. In some embodiments, the beads are non-toxic to cultured cells, e.g., cultured T cells. In some embodiments, the beads may be any particles which are capable of attaching agents in a manner that permits an interaction between the agent and a cell.

In some embodiments, a stimulatory reagent comprises one or more agents that are capable of activating and/or expanding cells, e.g., T cells, that are bound to or otherwise attached to a bead, for example to the surface of the bead. In certain embodiments, the bead is a non-cell particle. In particular embodiments, the bead may include a colloidal particle, a microsphere, nanoparticle, a magnetic bead, or the like. In some embodiments the beads are agarose beads. In certain embodiments, the beads are sepharose beads.

In particular embodiments, the stimulatory reagent comprises beads that are monodisperse. In certain embodiments, beads that are monodisperse comprise size dispersions having a diameter standard deviation of less than 5% from each other.

In some embodiments, the bead contains one or more agents, such as an agent that is coupled, conjugated, or linked (directly or indirectly) to the surface of the bead. In some embodiments, an agent as contemplated herein can include, but is not limited to, RNA, DNA, proteins (e.g., enzymes), antigens, polyclonal antibodies, monoclonal antibodies, antibody fragments, carbohydrates, lipids lectins, or any other affinity reagent with an affinity for a desired target. In some embodiments, the desired target is a T cell receptor and/or a component of a T cell receptor. In certain embodiments, the desired target is CD3. In certain embodiment, the desired target is a costimulatory molecule, e.g., CD28. The one or more agents may be attached directly or indirectly to the bead by a variety of methods known and available. The attachment may be covalent, noncovalent, electrostatic, or hydrophobic and may be accomplished by a variety of attachment means, including for example, a chemical means, a mechanical means, or an enzymatic means. In some embodiments, an affinity reagent (e.g., a biotinylated anti-CD3 antibody) may be attached indirectly to the bead via another affinity reagent (e.g., anti-biotin antibody) that is directly attached to the bead.

In some embodiments, one or more of the agents attached to the bead is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). In some embodiments, the stimulatory reagent is an antibody fragment (including antigen-binding fragment), e.g., a Fab, Fab'-SH, Fv, scFv, or (Fab')2 fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species). In some embodiments, the agent is an antibody that binds to and/or recognizes one or more components of a T cell receptor. In particular embodiments, the agent is an anti-CD3 antibody. In certain embodiments, the agent is an antibody that binds to and/or recognizes a co-receptor. In some embodiments, the stimulatory reagent comprises an anti-CD28 antibody.

In some embodiments, the bead has a diameter of greater than about 0.001 µm, greater than about 0.01 µm, greater than about 0.1 µm, greater than about 1.0 µm, greater than about 10 µm, greater than about 50 µm, greater than about 100 µm or greater than about 1000 µm and no more than about 1500 µm. In some embodiments, the bead has a diameter of about 1.0 µm to about 500 µm, about 1.0 µm to about 150 µm, about 1.0 µm to about 30 µm, about 1.0 µm to about 10 µm, about 1.0 µm to about 5.0 µm, about 2.0 µm to about 5.0 µm, or about 3.0 µm to about 5.0 µm. In some embodiments, the bead has a diameter of about 3 µm to about 5 µm. In some embodiments, the bead has a diameter of at least or at least about or about 0.001 µm, 0.01 µm, 0.1

µm, 0.5 µm, 1.0 µm, 1.5 µm, 2.0 µm, 2.5 µm, 3.0 µm, 3.5 µm, 4.0 µm, 4.5 µm, 5.0 µm, 5.5 µm, 6.0 µm, 6.5 µm, 7.0 µm, 7.5 µm, 8.0 µm, 8.5 µm, 9.0 µm, 9.5 µm, 10 µm, 12 µm, 14 µm, 16 µm, 18 µm or 20 µm. In certain embodiments, the bead has a diameter of or about 4.5 µm. In certain embodiments, the bead has a diameter of or about 2.8 µm.

In some embodiments, the beads have a density of greater than 0.001 g/cm$^3$, greater than 0.01 g/cm$^3$, greater than 0.05 g/cm$^3$, greater than 0.1 g/cm$^3$, greater than 0.5 g/cm$^3$, greater than 0.6 g/cm$^3$, greater than 0.7 g/cm$^3$, greater than 0.8 g/cm$^3$, greater than 0.9 g/cm$^3$, greater than 1 g/cm$^3$, greater than 1.1 g/cm$^3$, greater than 1.2 g/cm$^3$, greater than 1.3 g/cm$^3$, greater than 1.4 g/cm$^3$, greater than 1.5 g/cm$^3$, greater than 2 g/cm$^3$, greater than 3 g/cm$^3$, greater than 4 g/cm$^3$, or greater than 5 g/cm$^3$. In some embodiments, the beads have a density of between about 0.001 g/cm$^3$ and about 100 g/cm$^3$, about 0.01 g/cm$^3$ and about 50 g/cm$^3$, about 0.1 g/cm$^3$ and about 10 g/cm$^3$, about 0.1 g/cm$^3$ and about 0.5 g/cm$^3$, about 0.5 g/cm$^3$ and about 1 g/cm$^3$, about 0.5 g/cm$^3$ and about 1.5 g/cm$^3$, about 1 g/cm$^3$ and about 1.5 g/cm$^3$, about 1 g/cm$^3$ and about 2 g/cm$^3$, or about 1 g/cm$^3$ and about 5 g/cm$^3$. In some embodiments, the beads have a density of about 0.5 g/cm$^3$, about 0.5 g/cm$^3$, about 0.6 g/cm$^3$, about 0.7 g/cm$^3$, about 0.8 g/cm$^3$, about 0.9 g/cm$^3$, about 1.0 g/cm$^3$, about 1.1 g/cm$^3$, about 1.2 g/cm$^3$, about 1.3 g/cm$^3$, about 1.4 g/cm$^3$, about 1.5 g/cm$^3$, about 1.6 g/cm$^3$, about 1.7 g/cm$^3$, about 1.8 g/cm$^3$, about 1.9 g/cm$^3$, or about 2.0 g/cm$^3$. In certain embodiments, the beads have a density of about 1.6 g/cm$^3$. In particular embodiments, the beads or particles have a density of about 1.5 g/cm$^3$. In certain embodiments, the particles have a density of about 1.3 g/cm$^3$.

In certain embodiments, a plurality of the beads has a uniform density. In certain embodiments, a uniform density comprises a density standard deviation of less than 10%, less than 5%, or less than 1% of the mean bead density.

In some embodiments, the beads have a surface area of between about 0.001 m$^2$ per each gram of particles (m$^2$/g) to about 1,000 m$^2$/g, about 0.010 m$^2$/g to about 100 m$^2$/g, about 0.1 m$^2$/g to about 10 m$^2$/g, about 0.1 m$^2$/g to about 1 m$^2$/g, about 1 m$^2$/g to about 10 m$^2$/g, about 10 m$^2$/g to about 100 m$^2$/g, about 0.5 m$^2$/g to about 20 m$^2$/g, about 0.5 m$^2$/g to about 5 m$^2$/g, or about 1 m$^2$/g to about 4 m$^2$/g. In some embodiments, the particles or beads have a surface area of about 1 m$^2$/g to about 4 m$^2$/g.

In some embodiments, the bead contains at least one material at or near the bead surface that can be coupled, linked, or conjugated to an agent. In some embodiments, the bead is surface functionalized, i.e. comprises functional groups that are capable of forming a covalent bond with a binding molecule, e.g., a polynucleotide or a polypeptide. In particular embodiments, the bead comprises surface-exposed carboxyl, amino, hydroxyl, tosyl, epoxy, and/or chloromethyl groups. In particular embodiments, the beads comprise surface exposed agarose and/or sepharose. In certain embodiments, the bead surface comprises attached stimulatory reagents that can bind or attach binding molecules. In particular embodiments, the affinity reagents are polypeptides. In some embodiments, the beads comprise surface exposed protein A, protein G, or biotin.

In some embodiments, the bead reacts in a magnetic field. In some embodiments, the bead is a magnetic bead. In some embodiments, the magnetic bead is paramagnetic. In particular embodiments, the magnetic bead is superparamagnetic. In certain embodiments, the beads do not display any magnetic properties unless they are exposed to a magnetic field.

In particular embodiments, the bead comprises a magnetic core, a paramagnetic core, or a superparamagnetic core. In some embodiments, the magnetic core contains a metal. In some embodiments, the metal can be, but is not limited to, iron, nickel, copper, cobalt, gadolinium, manganese, tantalum, zinc, zirconium or any combinations thereof. In certain embodiments, the magnetic core comprises metal oxides (e.g., iron oxides), ferrites (e.g., manganese ferrites, cobalt ferrites, nickel ferrites, etc.), hematite and metal alloys (e.g., CoTaZn). In some embodiments, the magnetic core comprises one or more of a ferrite, a metal, a metal alloy, an iron oxide, or chromium dioxide. In some embodiments, the magnetic core comprises elemental iron or a compound thereof. In some embodiments, the magnetic core comprises one or more of magnetite (Fe3O4), maghemite (γFe2O3), or greigite (Fe3S4). In some embodiments, the inner core comprises an iron oxide (e.g., $Fe_3O_4$).

In certain embodiments, the bead contains a magnetic, paramagnetic, and/or superparamagnetic core that is covered by a surface functionalized coat or coating. In some embodiments, the coat can contain a material that can include, but is not limited to, a polymer, a polysaccharide, a silica, a fatty acid, a protein, a carbon, agarose, sepharose, or a combination thereof. In some embodiments, the polymer can be a polyethylene glycol, poly (lactic-co-glycolic acid), polyglutaraldehyde, polyurethane, polystyrene, cyclo-olefin polymer (COP) or a polyvinyl alcohol. In certain embodiments, the outer coat or coating comprises polystyrene. In particular embodiments, the outer coating is surface functionalized.

In some embodiments, the stimulatory reagent comprises one or more agents that are attached to a bead comprising a metal oxide core (e.g., an iron oxide inner core) and a coat (e.g., a protective coat), wherein the coat comprises polystyrene. In certain embodiments, the beads are monodisperse, superparamagnetic beads comprising a superparamagnetic iron core, e.g., a core comprising magnetite ($Fe_3O_4$) and/or maghemite ($\gamma Fe_2O_3$) c and a polystyrene coat or coating. In some embodiments, the bead is non-porous. In some embodiments, the beads contain a functionalized surface to which the one or more agents are attached. In certain embodiments, the one or more agents are covalently bound to the beads at the surface. In some embodiments, the one or more agents include an antibody or antigen-binding fragment thereof. In some embodiments, the one or more agents include an anti-CD3 antibody and an anti-CD28 antibody. In certain embodiments, the beads have a density of about 1.5 g/cm$^3$ and a surface area of about 1 m$^2$/g to about 4 m$^2$/g. In particular embodiments; the beads are monodisperse superparamagnetic beads that have a diameter of about 4.5 µm and a density of about 1.5 g/cm$^3$. In some embodiments, the beads the beads are monodisperse superparamagnetic beads that have a mean diameter of about 2.8 µm and a density of about 1.3 g/cm$^3$. In some embodiments, a stimulatory reagent comprises superparamagnetic, non-porous, monodispersed 4.5 µm polystyrene coated beads with a maghemite and magnetite core, with surface conjugated monoclonal anti-CD3 epsilon and anti-CD28 antibodies. In some embodiments, the stimulatory reagent is or contains Dynabeads® (Invitrogen).

In some embodiments, the stimulatory reagent comprises a bead that contains a metal oxide core (e.g., an iron oxide core) and a coat, wherein the metal oxide core comprises at least one polysaccharide (e.g., dextran), and wherein the coat comprises at least one polysaccharide (e.g., amino dextran), at least one polymer (e.g., polyurethane) and silica. In some embodiments the metal oxide core is a colloidal iron oxide core. In certain embodiments, the one or more agents include an antibody or antigen-binding fragment thereof. In particular embodiments, the one or more agents include an anti-CD3 antibody and an anti-CD28 antibody. In some embodiments, the stimulatory reagent comprises an anti-CD3 antibody, anti-CD28 antibody, and an anti-biotin antibody. In some embodiments, the stimulatory reagent comprises an anti-biotin antibody. In some embodiments, the bead has a diameter of about 3 μm to about 10 μm. In some embodiments, the bead has a diameter of about 3 μm to about 5 μm. In certain embodiments, the bead has a diameter of about 3.5 μm. In some embodiments, the stimulatory reagent comprises a composition of silica 3.5 μm chromatography beads with paramagnetic iron and dextran microbeads and surface conjugated anti-CD28 and anti-biotin antibodies.

B. Cells and Processing of Cells in the Presence of Particles

In some embodiments, the cells in a cell composition or processed for the preparation of a cell composition described herein generally are eukaryotic cells, such as mammalian cells, and typically are human cells. In some embodiments, the cells are or include cells of the immune system, such as cells of the innate or adaptive immunity, e.g., myeloid or lymphoid cells, including lymphocytes, typically T cells and/or NK cells. In some embodiments, the cell of the immune system (e.g., immune cell) is a T cell, B cell, macrophage, neutrophil, natural killer (NK) cell or dendritic cell. In some embodiments, cell composition comprises one or more cells of the immune system, such as CD4+ or CD8+ T cells. In some embodiments, the cell is or the cell composition comprises monocytes or granulocytes, e.g., myeloid cells, macrophages, neutrophils, dendritic cells, mast cells, eosinophils, and/or basophils. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells are primary cells, e.g., primary human cells.

In some embodiments, the cells in the cell composition are obtained from a biological sample. A biological sample includes a tissue sample, a fluid sample, and other biological sample taken directly from a subject, as well as a biological sample resulting from one or more processing steps, such as separation, centrifugation, genetic engineering (e.g., transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom. In some aspects, the biological sample from which the cells are derived, obtained or isolated is blood or a blood-derived sample, or is derived from an apheresis or leukapheresis product. In some embodiments, the cells from the circulating blood of a subject is obtained, e.g., by apheresis or leukapheresis. In some embodiments, the cells are immune cells (e.g., myeloid or lymphoid cells, including lymphocytes, typically T cells and/or NK cells) obtained or derived from the blood, bone marrow, lymph, or lymphoid organs. Exemplary biological samples also include, but are not limited to, whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. In some embodiments, the biological sample, contains lymphocytes, including T cells, monocytes, granulocytes, B cells, other nucleated white blood cells, red blood cells, and/or platelets, and in some aspects contains cells other than red blood cells and platelets.

In some embodiments, cells in a blood sample collected from a subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished with a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, Ca++/Mg++ free PBS. In certain embodiments, components of a blood sample are removed and the cells are directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the cells are derived from cell lines, e.g., T cell lines. The cells in some embodiments are obtained from a xenogeneic source, for example, from mouse, rat, non-human primate, and pig.

In some embodiments, the cells in the cell composition are or include cells for use in the context of cell therapy, e.g. adoptive cell therapy. In some cases, the biological sample is from an autologous source. In some cases, the biological sample is from an allogeneic source. In some embodiments, the methods described herein include isolating cells from a subject, preparing, processing, culturing, and/or engineering the cells, and re-introducing the cells into the same subject, before or after cryopreservation.

In some embodiments, the cells in the cell composition are or include cells obtained from a biological sample that has undergone one or more preparation and/or cell separation steps. In some examples, the cells or the cell population has been washed, centrifuged and/or incubated in the presence of one or more reagents, for example, to remove unwanted components, enrich for desired components, lyse or remove cells sensitive to particular reagents. In some examples, the cells or the cell population is prepared or obtained based on one or more property, such as density, adherent properties, size, sensitivity and/or resistance to particular components.

In some embodiments, a particle (e.g., bead particle) comprising an affinity reagent described herein can be used in affinity- or immunoaffinity-based separation methods, such as during processing of a cell composition. Typically, the affinity reagent, such as an antibody, is specific for one or more macromolecule (e.g., cell surface receptor) that is expressed or present on the surface of a cell. In some embodiments, the cell composition comprises one or more cells (e.g., 1, 2, 3, 4 or more cells) of the same cell type. In some embodiments, the cell composition comprises one or more cells (e.g., 1, 2, 3, 4 or more cells) of different cell types. The particle generally is directly or indirectly attached to the affinity reagent, e.g., an antibody. In some embodiments, any known method for separation using such particles (e.g., bead particle) may be used. For example, the isolation in some aspects includes separation of cells in a cell population by incubation with at least one particle carrying on its surface an affinity reagent, e.g. an antibody, that specifically binds to one or more macromolecule on a cell, followed generally by washing steps and separation of cells having bound the affinity reagent (e.g., antibody) from those cells having not bound to the affinity reagent (e.g., antibody).

In some embodiments, such separation steps in a separation method can be based on enrichment for a particular cell population by positive selection, in which the cells having bound the reagents are retained for further use. In some aspects, multiple rounds of separation steps are carried out in which one or more positive selections can be performed. In some cases, multiple cell types can simultaneously be positively selected by incubating the cells with a plurality of affinity reagents such as antibodies that bind to one or more macromolecule expressed on the various cell types.

In some embodiments, the separation method can also employ one or more negative selection step, in which cells having not bound to the affinity reagent are the enriched cell population. In some aspects, one or more positive selection step is combined with one or more negative selection step, for example, where the positive and/or negative fractions are retained and further processed or subject to further separation positive and/or negative fraction steps. For example, the positively or negatively selected fraction from one step can be subjected to another separation step, such as a subsequent positive or negative selection. In some aspects, negative selection can be particularly useful where no affinity reagent (e.g., antibody) is available that specifically identifies a cell type in a heterogeneous population, such that separation is best carried out based on markers (e.g., macromolecules) expressed by cells other than the desired population. Generally, such methods employ at least one positive selection step, whereby the particles (e.g., a particle comprising an affinity reagent) may remain associated with the cell.

The particular particle (e.g., a particle comprising an affinity reagent) to employ for enriching or separating a particular cell type or subset of cells from a population can be determined. For example, the particular choice of an affinity reagent attached to a particle (e.g., bead particle) will depend on the particular cell type or subset of cells to be separated or enriched, the availability of affinity reagents against a particular cell type or subset of cells, the choice of one or more positive selection or a combination of positive and negative selection methods.

In an exemplary aspect, specific subpopulations of T cells can be isolated by positive and/or negative selection techniques, for example, for cells positive or expressing high levels of one or more surface markers (e.g., one or more macromolecules), such as CD28+, CD62L+, CCR7+, CD27+, CD127+, CD3+, CD4+, CD8+, CD45RA+, and/or CD45RO+ T cells. In some aspects, such enrichment and separation methods can be used to obtain a T cell population suitable for processing, preparing and/or engineering cells for adoptive cell therapy methods.

In some embodiments, T cells are separated from a PBMC sample by negative selection of markers expressed on non-T cells, such as B cells, monocytes, or other white blood cells, such as NK cells. In some aspects, a CD4+ or CD8+ positive selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining $T_{CM}$-enriched CD8+ T cells and CD4+ T cells further enhances efficacy.

In embodiments, memory T cells are present in both CD62L+ and CD62L− subsets of CD8+ peripheral blood lymphocytes. A PBMC sample can be enriched for or depleted of CD62L-CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order. In some cases, the combination of positive and negative selection can be used to sort CD4+ T helper cells into naïve, central memory, and effector cells by identifying cell populations that have cell surface antigens. In some embodiments, naive CD4+ T lymphocytes are CD45RO−, CD45RA+, CD62L+, and CD4+ T cells. In some embodiments, central memory CD4+ cells are CD62L+ and CD45RO+. In some embodiments, effector CD4+ cells are CD62L− and CD45RO−.

In some embodiments, the cells and/or cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ). Immunomagnetic methods of cell separation can utilize a paramagnetic bead particle comprising a magnetic core (e.g., iron oxide core), such as any described above (e.g., such as Dynabeads® or MACSiBeads™ Particles). In some embodiments, the magnetic bead particle comprises a magnetically responsive material bound to a specific affinity reagent, such as an antibody or other affinity reagent. There are many well-known magnetically responsive materials used in magnetic separation methods. Suitable magnetic bead particles include those described in herein as well as in Molday, U.S. Pat. No. 4,452,773 and in European Patent Specification EP 452342 B. Colloidal sized particles, such as those described in Owen U.S. Pat. No. 4,795,698, and Liberti et al., U.S. Pat. No. 5,200,084 are other examples of suitable magnetic bead particles.

In some aspects, a cell composition or a sample obtained or derived from a cell composition described herein to be separated is incubated with at least one magnetic bead particle described herein. The incubation generally is carried out under conditions whereby affinity reagents, e.g., antibodies, which are attached to the magnetic bead particle, specifically bind to cell surface macromolecules if present on cells within the sample or cell composition. In some aspects, the sample or cell composition is placed in a magnetic field, and those cells having magnetically responsive or magnetizable bead particles attached thereto will be attracted to the magnet and separated from cells not having such bead particles attached thereto.

In some embodiments, the affinity-based selection is via magnetic-activated cell sorting (MACS) (Miltenyi Biotec, Auburn, CA). MACS systems are capable of high-purity selection of cells having magnetic bead particles attached thereto. In certain embodiments, MACS operates in a mode wherein the non-target cells and target cells are sequentially eluted after the application of the external magnetic field. That is, cells attached to magnetic bead particles (e.g., target cells) are held in place while the unattached cells (e.g., non-target cells) are eluted. Then, after this first elution step is completed, the target cells that were trapped in the magnetic field and were prevented from being eluted are freed in some manner such that they can be eluted and recovered. In certain embodiments, the non-target cells are labelled and depleted from the heterogeneous population of cells.

For positive selection, cells that are attracted to the magnet are retained; for negative selection, cells that are not attracted to the magnet (unlabeled cells) are retained.

In certain embodiments, the isolation or separation is carried out in an integrated or self-contained system, device, or apparatus, for example, to provide a closed or sterile environment, for example, to minimize error, user handling and/or contamination. In some cases, one or more other further processing steps also can be carried out in the system, such as one or more other processing, incubation, culture, and/or formulation steps. In one example, the system is a system as described in International Patent Application, Publication Number WO2009/072003, or US 20110003380. In some embodiments, the isolation or separation is carried out in an automated or programmable fashion. In some aspects, the system or apparatus includes a computer and/or computer program in communication with the system or apparatus, which allows a user to program, control, assess the outcome of, and/or adjust various aspects of the isolation or separation or one or more other steps of the process.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetic bead particles that are supplied in a sterile, non-pyrogenic solution. In some embodiments, after labelling of cells with magnetic bead particles the cells are washed to remove excess magnetic bead particles. In some embodiments, the cells are washed a plurality of times. A cell preparation bag is then connected to the tubing set, which in turn is connected to a bag containing buffer and a cell collection bag. The tubing set consists of pre-assembled sterile tubing, including a pre-column and a separation column, and are for single use only. In some embodiments, the tubing set does not comprise a pre-column. After initiation of the separation program, the system automatically applies the cell sample onto the separation column. Labelled cells are retained within the column, while unlabeled cells are removed by a series of washing steps. In some embodiments, the cell populations for use with the methods described herein are labeled with magnetic bead particles, such as those described herein, and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unit that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) J Immunother. 35(9): 651-660, Terakura et al. (2012) Blood. 1:72-82, and Wang et al. (2012) J Immunother. 35(9):689-701.

In some embodiments, a particle comprising an affinity reagent can be used connection with stimulation, activation and/or expansion of one or more cell types. In some embodiments, the affinity reagent provides a stimulating agent that induces the proliferation, expansion, stimulation and/or survival of cells in the cell population, for example, to mimic antigen exposure and/or to induce cell signaling through one or more cell surface receptors In some embodiment, the affinity reagent, e.g. an antibody or ligand, coated or bound to a particle described herein, provides a stimulating condition capable of activating an intracellular signaling domain of a TCR complex. In some aspects, the affinity reagent turns on or initiates TCR/CD3 intracellular signaling cascade in a T cell. In some embodiments, signaling can be potentiated or enhanced in the presence of a costimulatory signal. In some embodiments, affinity reagents that can promote stimulation or activation can include antibodies, such as those specific for a TCR component and/or costimulatory receptor, e.g., anti-CD3, anti-CD28, for example. In some embodiments, when an anti-CD3 antibody is immobilized on a surface, such as a particle (e.g. microsphere or bead particle), it can deliver an activating and proliferation-inducing signal by crosslinking of the T cell receptor complex on the surface of T cells. In some cases, by immobilizing anti-CD3 and anti-CD28 to simultaneously deliver a signal and a co-stimulatory signal, proliferation can be increased. Various solid phase surface particles, including microsphere and bead particles, are known that are immobilized with anti-CD3 and anti-CD28 beads (WO09429436; EP01257632; US2008/0317724 and U.S. Pat. No. 8,012,750). In some cases, the particles can include nanoparticles or microparticles.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml).

Typically, it has been shown that stimulation or activation with anti-CD3/anti-CD28 particles is generally greater when effected using microparticles as compared to nanoparticles. For example, it has been shown that micron-sized particles, which are close in size to T cells, provide for optimal T cell stimulation (see e.g. Steenbloc and Fahmy, (2008) Molecular Therapy, 16:765-772; Mescher et al. (1992) J. Immunol., 149:2402-2405). A problem with existing methods for assessing the presence of particles is that many cannot differentiate between particles that are substantially the same size as a cell. In some embodiments, the provided methods overcome these problems, since the cells are lysed while leaving the particles (e.g., bead particles) intact. In some embodiments, anti-CD3/anti-CD28 microparticles (e.g., bead particles) have a size from or from about 1 µm to 24 µm, such as 2 µm to 10 µm or 3 µm to 5 µm, such as about or at least about or 3 µm, 3.5 µm, 4.0 µm, 4.5 µm or 5.0 µm.

Optionally, the stimulation, activation or expansion can also include the addition of one or more other stimulating conditions, such as to a culture medium. In some embodiments, stimulation conditions include addition of a stimulating cytokine, for example, IL-2 and/or IL-15, for example, at an IL-2 concentration of at least about 10 units/mL. In some embodiments, the conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In such aspects, one or more particles (e.g., bead particles) may be retained with one or more of the cells. In some embodiments, the particles (e.g., bead particles, including magnetizable particles) are left attached to the cells that are to be subsequently incubated, cultured and/or engineered; in some aspects, the particles are left attached to the cells for administration to a patient.

In some embodiments, the particles (e.g., bead particles, including magnetizable or magnetically responsive particles) are removed from the cell composition. In some embodiments, the particles (e.g., bead particles, including magnetizable or magnetically responsive particles) are not completely removed from the cell composition, thereby producing a residual bead cell composition. Methods for removing particles (e.g., bead particles or magnetizable particles) from cells are known. In come embodiments, the use of competing non-labeled antibodies can be used, which, for example, bind to the primary antibody and alter its affinity for its antigen on the cell, thereby permitting for gentle detachment. In some cases, after detachment, the competing antibodies may remain associated with the particle (e.g. bead particle) while the unreacted antibody is or may be washed away and the cell is free of isolating, selecting, enriching and/or activating antibody. Exemplary of such a reagent is DETACaBEAD (Friedl et al. 1995; Entschladen et al. 1997). In some embodiments, particles (e.g., bead particles) can be removed in the presence of a cleavable linker (e.g. DNA linker), whereby the particle-bound antibodies are conjugated to the linker (e.g. CELLection, Dynal). In some cases, the linker region provides a cleavable site to remove the particles (e.g., bead particles) from the cells after isolation, for example, by the addition of DNase or other releasing buffer. In some embodiments, other enzymatic methods can also be employed for release of a particle (e.g. bead particle) from cells. In some embodiments, the particles (e.g., bead particles or magnetizable particles) are biodegradable.

In some embodiments, the preparation methods include steps for freezing, e.g., cryopreserving, the cells or cell population in the cell composition, either before or after isolation, incubation, and/or engineering. In some embodiments, the freeze and subsequent thaw step removes granulocytes and, to some extent, monocytes in the cell composition. In some embodiments, the cells or cell population in the cell composition is suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to 80° C. at a rate of 1° per minute and stored in the vapor phase of a liquid nitrogen storage tank.

C. Pharmaceutical Compositions and Formulations

In some embodiments, the cell composition is a pharmaceutical composition or formulation that includes a therapeutically effective amount of cells for administration. In some embodiments, the pharmaceutical composition or formulation can be a unit dose form composition including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation or composition would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the pharmaceutical compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The pharmaceutical compositions can include aqueous solutions.

The formulation or composition can be used either alone or in combination with other agents in a therapy. For instance, the composition may be co-administered with at least one additional therapeutic agent. In some embodiments, the formulation or composition may contain more than one active ingredient (e.g., therapeutic agent) useful for the particular indication, disease, or condition being treated with the cells, preferably those with activities complementary to the cells, where the respective activities do not adversely affect one another. Such active ingredients (e.g., therapeutic agents) are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. In some embodiments, the composition of the invention is in a separate formulation from the additional therapeutic agent. In some embodiments, the administration of the composition of the invention can occur prior to, simultaneously, and/or following administration of the additional therapeutic agent.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells. In some embodiments, the cells are formulated for administration in a single pharmaceutical composition, such as in single dosage form. In some embodiments, the cells are formulated for administration in multiple dosage form. In some cases, such as in the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, such as generally no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period. Thus, in some aspects, the cells are administered in a single pharmaceutical composition. In some embodiments, the cells are administered in a plurality of compositions, collectively containing the cells of a single dose.

In some embodiments, the cells are formulated for administration in the range from about $10^5$ to about $10^6$ of such cells per kilogram body weight of the subject, and/or a number of such cells that is no more than about $10^5$ or about $10^6$ such cells per kilogram body weight of the subject. For example, in some embodiments, the cells are formulated for administration of a dose that includes less than or no more than at or about $1 \times 10^5$, at or about $2 \times 10^5$, at or about $5 \times 10^5$, or at or about $1 \times 10^6$ of such cells per kilogram body weight of the subject. In some embodiments, the cells are formulated for administration of a dose that includes at or about $1 \times 10^5$, at or about $2 \times 10^5$, at or about $5 \times 10^5$, or at or about $1 \times 10^6$ of such cells per kilogram body weight of the subject, or a value within the range between any two of the foregoing values. In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some embodiments, the cells are formulated in the composition in an amount to provide one or more unit doses of cells, which may be an amount or number of the cells to be administered to the subject in a single dose or in one or more split doses. In some embodiments, the unit dose includes less than about $1 \times 10^8$, less than about $5 \times 10^7$, less than about $1 \times 10^6$ or less than about $5 \times 10^5$ of the engineered cells, of total cells, of T cells, or PBMCs, per kg of the subject to be treated and/or from which the cells have been derived. In some embodiments, each unit dose contains at least or about at least or about or $2 \times 10^6$, $5 \times 10^6$, $1 \times 10^7$, $5 \times 10^7$, or $1 \times 10^8$ engineered cells, total cells, T cells, or PBMCs.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose includes fewer than about $5 \times 10^8$ total recombinant receptor (e.g., CAR)-expressing cells, T cells, or peripheral blood mononuclear cells (PBMCs), e.g., in the range of about $1 \times 10^6$ to $5 \times 10^8$ such cells, such as $2 \times 10^6$, $5 \times 10^6$, $1 \times 10^7$, $5 \times 10^7$, $1 \times 10^8$, or $5 \times 10^8$ total such cells, or the range between any two of the foregoing values.

In some embodiments, the dose of genetically engineered cells comprises from or from about $1 \times 10^5$ to $5 \times 10^8$ total CAR-expressing T cells, $1 \times 10^5$ to $2.5 \times 10^8$ total CAR-expressing T cells, $1 \times 10^5$ to $1 \times 10^8$ total CAR-expressing T cells, $1 \times 10^5$ to $5 \times 10^7$ total CAR-expressing T cells, $1 \times 10^5$ to $2.5 \times 10^7$ total CAR-expressing T cells, $1 \times 10^5$ to $1 \times 10^7$ total CAR-expressing T cells, $1 \times 10^5$ to $5 \times 10^6$ total CAR-expressing T cells, $1 \times 10^5$ to $2.5 \times 10^6$ total CAR-expressing T cells, $1 \times 10^5$ to $1 \times 10^6$ total CAR-expressing T cells, $1 \times 10^6$ to $5 \times 10^8$ total CAR-expressing T cells, $1 \times 10^6$ to $2.5 \times 10^8$ total CAR-expressing T cells, $1 \times 10^6$ to $1 \times 10^8$ total CAR-expressing T cells, $1 \times 10^6$ to $5 \times 10^7$ total CAR-expressing T cells, $1 \times 10^6$ to $2.5 \times 10^7$ total CAR-expressing T cells, $1 \times 10^6$ to $1 \times 10^7$ total CAR-expressing T cells, $1 \times 10^6$ to $5 \times 10^6$ total CAR-expressing T cells, $1 \times 10^6$ to $2.5 \times 10^6$ total CAR-expressing T cells, $2.5 \times 10^6$ to $5 \times 10^8$ total CAR-expressing T cells, $2.5 \times 10^6$ to $2.5 \times 10^8$ total CAR-expressing T cells, $2.5 \times 10^6$ to $1 \times 10^8$ total CAR-expressing T cells, $2.5 \times 10^6$ to $5 \times 10^7$ total CAR-expressing T cells, $2.5 \times 10^6$ to $2.5 \times 10^7$ total CAR-expressing T cells, $2.5 \times 10^6$ to $1 \times 10^7$ total CAR-expressing T cells, $2.5 \times 10^6$ to $5 \times 10^6$ total CAR-expressing T cells, $5 \times 10^6$ to $5 \times 10^8$ total CAR-expressing T cells, $5 \times 10^6$ to $2.5 \times 10^8$ total CAR-expressing T cells, $5 \times 10^6$ to $1 \times 10^8$ total CAR-expressing T cells, $5 \times 10^6$ to $5 \times 10^7$ total CAR-expressing T cells, $5 \times 10^6$ to $2.5 \times 10^7$ total CAR-expressing T cells, $5 \times 10^6$ to $1 \times 10^7$ total CAR-expressing T cells, $1 \times 10^7$ to $5 \times 10^8$ total CAR-expressing T cells, $1 \times 10^7$ to $2.5 \times 10^8$ total CAR-expressing T cells, $1 \times 10^7$ to $1 \times 10^8$ total CAR-expressing T cells, $1 \times 10^7$ to $5 \times 10^7$ total CAR-expressing T cells, $1 \times 10^7$ to $2.5 \times 10^7$ total CAR-expressing T cells, $2.5 \times 10^7$ to $5 \times 10^8$ total CAR-expressing T cells, $2.5 \times 10^7$ to $2.5 \times 10^8$ total CAR-expressing T cells, $2.5 \times 10^7$ to $1 \times 10^8$ total CAR-expressing T cells, $2.5 \times 10^7$ to $5 \times 10^7$ total CAR-expressing T cells, $5 \times 10^7$ to $5 \times 10^8$ total CAR-expressing T cells, $5 \times 10^7$ to $2.5 \times 10^8$ total CAR-expressing T cells, $5 \times 10^7$ to $1 \times 10^8$ total CAR-expressing T cells, $1 \times 10^8$ to $5 \times 10^8$ total CAR-expressing T cells, $1 \times 10^8$ to $2.5 \times 10^8$ total CAR-expressing T cells, or $2.5 \times 10^8$ to $5 \times 10^8$ total CAR-expressing T cells.

In some embodiments, the dose of genetically engineered cells comprises at least or at least about $1 \times 10^5$ CAR-expressing cells, at least or at least about $2.5 \times 10^5$ CAR-expressing cells, at least or at least about $5 \times 10^5$ CAR-expressing cells, at least or at least about $1 \times 10^6$ CAR-expressing cells, at least or at least about $2.5 \times 10^6$ CAR-expressing cells, at least or at least about $5 \times 10^6$ CAR-expressing cells, at least or at least about $1 \times 10^7$ CAR-expressing cells, at least or at least about $2.5 \times 10^7$ CAR-expressing cells, at least or at least about $5 \times 10^7$ CAR-expressing cells, at least or at least about $1 \times 10^8$ CAR-expressing cells, at least or at least about $2.5 \times 10^8$ CAR-expressing cells, or at least or at least about $5 \times 10^8$ CAR-expressing cells.

In some embodiments, the cell therapy comprises administration of a dose comprising a number of cell from or from about $1 \times 10^5$ to $5 \times 10^8$ total recombinant receptor-expressing cells, total T cells, or total peripheral blood mononuclear cells (PBMCs), from or from about $5 \times 10^5$ to $1 \times 10^7$ total recombinant receptor-expressing cells, total T cells, or total peripheral blood mononuclear cells (PBMCs) or from or from about $1 \times 10^6$ to $1 \times 10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1 \times 10^5$ total recombinant receptor-expressing cells, total T cells, or total peripheral blood mononuclear cells (PBMCs), such at least or at least $1 \times 10^6$, at least or at least about $1 \times 10^7$, at least or at least about $1 \times 10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1 \times 10^5$ to $5 \times 10^8$ CD3+ or CD8+ total T cells or CD3+ or CD8+ recombinant receptor-expressing cells, from or from about $5 \times 10^5$ to $1 \times 10^7$ CD3+ or CD8+ total T cells or CD3+ or CD8+ recombinant receptor-expressing cells, or from or from about $1 \times 10^6$ to $1 \times 10^7$ CD3+ or CD8+ total T cells or CD3+ or CD8+ recombinant receptor-expressing cells, each inclusive. In some embodiments, the cell therapy comprises administration of a dose comprising a number of cell from or from about $1 \times 10^5$ to $5 \times 10^8$ total CD3+/CAR+ or CD8+/CAR+ cells, from or from about $5 \times 10^5$ to $1 \times 10^7$ total CD3+/CAR+ or CD8+/CAR+ cells, or from or from about $1 \times 10^6$ to $1 \times 10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1 \times 10^6$ and $5 \times 10^8$ total recombinant receptor (e.g., CAR)-expressing CD8+ cells, e.g., in the range of about $5 \times 10^6$ to $1 \times 10^8$ such cells, such cells $1 \times 10^7$, $2.5 \times 10^7$, $5 \times 10^7$, $7.5 \times 10^7$, $1 \times 10^8$, or $5 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1 \times 10^7$ to $0.75 \times 10^8$ total recombinant receptor-expressing CD8+ T cells, $1 \times 10^7$ to $2.5 \times 10^7$ total recombinant receptor-expressing CD8+ T cells, from or from about $1 \times 10^7$ to $0.75 \times 10^8$ total recombinant receptor-expressing CD8+ T cells, each inclusive. In some embodiments, the dose of cells comprises the administration of or about $1 \times 10^7$, $2.5 \times 10^7$, $5 \times 10^7$ $7.5 \times 10^7$, $1 \times 10^8$, or $5 \times 10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In some embodiments, the cells and compositions are formulated for administration using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

IV. Articles of Manufacture and Kits

Also provided are articles of manufacture or kits containing the reagents or components for performing any of the provided methods. The articles of manufacture include one or more containers, typically a plurality of containers, packaging material, and a label or package insert on or associated with the container or containers and/or packaging, generally including instructions for performing the provided method.

In some embodiments, the articles of manufacture include one or more lysis solution (e.g., solutions containing a bleach and/or a detergent) for performing the method, which are packaged as articles of manufacture containing packaging materials and, optionally, instructions for performing the method. In some embodiments, the articles of manufacture and kits may further contain reagents and/or instruments for enumerating or detecting the presence or absence of particles in a cell composition. Reagents include, but are not limited to, additional detection reagents for detecting an affinity reagent on the surface of a particle, rinse or wash buffer or solution, which each, optionally, can be contained in a packaging material. In some embodiments, the articles of manufacture include one or more instruments for performing the method, e.g., instruments or apparatus for automated detection and/or analysis. Instruments include, but are not limited to, a plate reader, a microscope, a computer, a robot, a counting apparatus (e.g., hemocytometer), magnets, and pipettes (e.g., automatic pipette).

In some embodiments, the articles of manufacture also can include one or more reagents for detection, selection, enrichment, isolation, activation and/or stimulation of cells. In some embodiments, such reagents can include particles (e.g., bead particles) that specifically bind to a macromolecule on the surface of a cell to effect one or more of detection, selection, enrichment, isolation, activation and/or stimulation of cells. In some embodiments, the particles are conjugated with an anti-CD3 and/or anti-CD28 antibody. In some embodiments, the particles can include any as described herein or known.

Examples of packaging materials can include, for example, bottles, tubes, bags, vials, containers, syringes, bottles or any packaging material suitable for carrying or holding the lysis solution or solutions. In general, the packaging is one that is non-reactive with the lysis solution or buffer. The containers may be formed from a variety of materials such as glass or plastic. In some embodiments, the container has a sterile access port.

The article of manufacture or kit may further include a package insert with instructions for enumerating or detecting the presence or absence of non-cell particles in a cell composition. The label or a package insert, which is on or associated with the container, may indicate directions for reconstitution and/or use of the reagents, lysis solutions, materials and/or instruments in accord with the present disclosure. In some embodiments, the instructions can specify any one or more steps of the methods described herein. In some embodiments, the instructions specify the steps of: incubating a sample comprising at least a portion of an input composition or a sample derived from the input composition, said input composition comprising one or more cells and one or more non-cell particles, wherein the incubating is with the solution under conditions to induce lysis of cells to produce an output composition; analyzing the output composition or a portion thereof by fluorescence imaging to determine the presence or absence of particles in the sample. In some embodiments, the instructions specify that no detectable reagent or moiety is added to the output composition prior to the analyzing. The label or package insert may further indicate that the lysis solutions, reagents and/or materials are useful for enumerating or detecting the presence of absence of non-cell particles in a cell composition for use in therapy (e.g., adoptive cell therapy), such as in accord with the present disclosure. In some embodiments, the instructions specify analysis steps and/or parameters used for analysis, e.g., for automated detection and/or analysis of the fluorescent imaging.

V. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein, including below, for clarity and/or for ready reference, and the inclusion of such definitions herein should not necessarily be construed to represent a substantial difference over what is generally understood in the art.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. In some embodiments, "about" refers to a range of ±50%, ±40%, ±30%, ±25%, ±20%, ±15%, ±10%, ±5%, or ±1% of the value or parameter.

As used herein, the singular forms "a," "an," and "the" include plural referents unless the context clearly dictates otherwise. For example, "a" or "an" means "at least one" or "one or more." It is understood that aspects, embodiments, and variations described herein include "comprising," "consisting," and/or "consisting essentially of" aspects, embodiments and variations.

As used herein, a "cell composition" refers to any mixture of two or more products, including cells. Such composition can, in some cases, also include non-cell particles (e.g., bead particles). It may be a solution, a suspension, liquid, powder, a paste, aqueous, non-aqueous or any combination thereof.

The term "package insert" is used to refer to instructions customarily included in commercial packages of therapeutic products, that contain information about the indications, usage, dosage, administration, combination therapy, contraindications and/or warnings concerning the use of such therapeutic products.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

VI. Exemplary Embodiments

Among the provided embodiments are:

1. A method for detecting the presence or absence of particles in a cell composition, the method comprising the steps of:
    a) incubating a sample comprising at least a portion of an input composition or a sample derived from the input composition, said input composition comprising one or more cells and one or more non-cell particles, wherein the incubating is under conditions to induce lysis of cells to produce an output composition; and
    b) analyzing the output composition or a portion thereof by fluorescence imaging to determine the presence or absence of particles in the sample.

2. A method for detecting the presence or absence of particles in a cell composition, the method comprising analyzing an output composition or a portion thereof by fluorescence imaging to determine the presence or absence of particles in the sample, wherein the output composition is produced by incubating a sample comprising at least a portion of an input composition or a sample derived from the input composition under conditions to induce lysis of cells, said input composition comprising cells and one or more non-cell particles.

3. The method of embodiment 1 or embodiment 2, wherein prior to the analyzing the output composition is enriched for the one or more non-cell particles.

4. The method of any of embodiments 1-3, wherein the analyzing the output composition by fluorescence imaging comprises obtaining fluorescent micrographs of the output composition or a portion thereof, and optionally determining the fluorescent intensity of image objects from the fluorescent micrographs.

5. The method of any of embodiments 1-4, wherein the method further comprises obtaining brightfield micrographs of the output composition or a portion thereof.

6. The method of embodiment 4 or embodiment 5, wherein the analyzing the output composition further comprises determining the size, area, and/or circularity of image objects from the fluorescent micrographs or brightfield micrographs.

7. The method of any of embodiments 1-6, wherein:
the output composition does not comprise an agent for detecting the particles, optionally wherein the agent is or comprises a detectable moiety or is capable of producing a detectable; signal; or
the analyzing does not comprise adding an agent for detecting the particles to the output composition, optionally wherein the agent is or comprises a detectable moiety or is capable of producing a detectable signal.

8. A method for detecting the presence of absence of particles in a cell composition, comprising
(i) illuminating an output composition or a portion thereof with one or more light sources to generate an illuminated sample, wherein at least one light source is capable of exciting fluorescent molecules;
(ii) capturing one or more images of the illuminated sample, wherein at least one image is a fluorescent image;
(iii) analyzing the presence or absence of image objects from the one or more images for one or more parameters selected from size, area, fluorescent intensity (FI), brightfield intensity, and/or circularity;
wherein the output composition is produced by incubating a sample comprising at least a portion of an input composition or a sample derived from the input composition, said input composition comprising one or more cells and one or more non-cell particles under conditions to induce lysis of the cells.

9. The method of embodiment 8, wherein prior to the illuminating the output composition is enriched for the one or more non-cell particles.

10. A method for detecting the presence or absence of particles in a cell composition, the method comprising the steps of:
a) incubating a sample comprising at least a portion of an input composition or a sample derived from the input composition, said input composition comprising one or more cells and one or more non-cell particles, wherein the incubating is under conditions to induce lysis of cells to produce an output composition;
b) optically analyzing the output composition or portion thereof to assess the presence or absence of one or more parameters of one or more image objects, wherein the one or more parameters is selected from size, area, fluorescent intensity (FI), brightfield intensity, and/or particle circularity.

11. A method for detecting the presence or absence of particles in a cell composition, the method comprising optically analyzing an output composition or portion thereof to assess the presence or absence of one or more parameters of one or more image objects, said one or more parameters selected from size, area, fluorescent intensity (FI), brightfield intensity, and/or particle circularity, wherein the output composition is produced by incubating a sample comprising at least a portion of an input composition or a sample derived from the input composition under conditions to induce lysis of cells, said input composition comprising cells and one or more non-cell particles.

12. The method of embodiment 10 or embodiment 11, wherein prior to the analyzing the output composition is enriched for the one or more non-cell particles.

13. The method of any of embodiments 8-12, wherein:
the output composition does not comprise an agent for detecting the particles, optionally wherein the agent is or comprises a detectable moiety or is capable of producing a detectable; signal; or
the analyzing does not comprise adding an agent for detecting the particles to the output composition, optionally wherein the agent is or comprises a detectable moiety or is capable of producing a detectable signal.

14. The method of any of embodiments 4, 6 and 8-13, wherein an image object is a non-cell particle if:
(i) the image object comprises a circularity of at or at least 0.5, 0.6, 0.7, 0.8, or 0.9;
(ii) the image object comprises a diameter of between 5 µm and 10 inclusive; and/or
(iii) the image object comprises an area of between 25 µm$^2$ and 50 µm$^2$;
(iv) the image object comprises a fluorescent signal, optionally above a background signal in a control sample; and/or
(v) the image object comprises a florescent intensity (FI), optionally wherein the FI is greater than a background signal in a control sample.

15. The method of embodiment 14, wherein the control sample is a composition produced by incubating a cell composition comprising the one or more cells but not comprising, or not likely comprising, the one or more non-cell particles, wherein the incubating is under conditions to induce lysis of cells to produce an output composition 16. The method of any of embodiments 1-15, wherein the one or more non-cell particles, optionally one or more beads, are autofluorescent.

17. The method of any of embodiments 1-16, wherein the analyzing is carried out using a computer-implemented image analysis.

18. The method of any of embodiments 1-17, wherein one or more steps of the method is high-throughput and/or automated.

19. The method of any of embodiments 1-18, wherein one or more steps of the method is carried out by a machine, a robot and/or a computer-implemented algorithm.

20. The method of any of embodiments 1-19, wherein:
the input composition comprises or is suspected of comprising one or more of the non-cell particles bound to the surface of one or more cells in the input composition;
the input composition comprises or is suspected of comprising residual particles;
the input composition is derived from a composition containing one or more cells bound to one or more of the non-cell particles; and/or
the input composition is derived from a composition containing one or more cells bound to one or more of the non-cell particles is further processed by removing one or more of the non-cell particles.

21. The method of any of embodiments 1-20, wherein the input composition is produced by a method comprising:
(1) mixing one or more cells with one or more of the non-cell particles; and
(2) removing one or more of the non-cell particles from the cells.

22. The method of any of embodiments 1-21, wherein the input composition comprises or is likely to comprise or may comprise residual non-cell particles, said residual non-cell particles present following removal of one or more non-cell particles from a cell composition.

23. The method of any of embodiments 1-22, wherein the one or more of the particles comprise one or more biomolecule capable of binding to a macromolecule on the surface of a cell.

24. The method of any of embodiments 1-23, wherein the incubating under conditions to induce lysis of cells comprises incubating the sample with a detergent and/or a bleach.

25. The method of embodiment 24, wherein the detergent is one or more of Triton X-100, Triton X-114, NP-40, Brij-35, Brij-58, Tween 20, Tween 80, digitonin, octyl glucoside, octyl thioglucoside, sodium dodecyl sulfate (SDS), 3-[(3-cholamidopropyl)dimethylammonio]-1-propanesulfonate (CHAPS) and CHAPSO.

26. The method of embodiment 24 or embodiment 25, wherein the bleach is a chlorine-based bleach.

27. The method of any of embodiments 24-26, wherein the sample is incubated with bleach at a concentration of about 0.1%, 0.2%, 0.3%, 0.4%, 0.5%, 1%, 1.5%, 2%, 3%, 4%, 5%, 6%, 7% or 8% (v/v) bleach, or a range defined by any two of the foregoing values.

28. The method of any of embodiments 1-27, wherein:
the incubating is carried out for at least or at least about 30 seconds, 1 minute, 2 minutes, 3 minutes, 4 minutes, 5 minutes, 10 minutes, 20 minutes or 30 minutes; or
the incubating is carried out from or from about 30 seconds to 30 minutes, 1 minute to 20 minutes, 1 minute to 10 minutes or 1 minute to 5 minutes.

29. The method of any of embodiments 3-7, 9 and 12-28, wherein the particles are enriched by exposing the output composition to a magnetic field.

30. The method of any of embodiments 3-7, 9 and 12-29, wherein the enriching reduces or removes cell debris from the output composition.

31. The method of any of embodiments 1-30, wherein prior to the analyzing or capturing the method further comprises rinsing or washing the output composition.

32. The method of embodiment 31, wherein rinsing or washing the output composition comprises pelleting the one or more non-cell particles and removing a volume or reducing a volume of the output composition.

33. The method of any of embodiments 1-32, wherein the concentration of cells in the sample is at least or at least about $2\times10^5$ cells/mL, at least or at least about $5\times10^5$ cells/mL, at least or at least about $1\times10^6$ cells/mL, at least or at least about $5\times10^6$ cells/mL, at least or at least about $1\times10^7$ cells/mL, at least or at least about $5\times10^7$ cells/mL, at least or at least about $1\times10^8$ cells/mL or at least or at least about $5\times10^7$ cells/mL.

34. The method of any of embodiments 1-33, wherein:
the volume of the output composition is at or about or is at least at or about 10 µL, 25 µL, 50 µL, 75 µL, 100 µL, 125 µL, 200 µL, 250 µL, 500 µL, 750 µL, 1 mL, 2 mL, 3 mL, 4 mL, 5 mL, 6 mL, 7 mL, 8 mL, 9 mL, or 10 mL, or a range defined by any two of the foregoing values.

35. The method of any of embodiments 1-34, wherein the one or more non-cell particles comprise beads.

36. The method of any of embodiments 1-35, wherein the one or more of the non-cell particles, optionally one or more beads, has a diameter of greater than 0.001 µm, greater than 0.01 µm, greater than 0.1 µm, greater than 1.0 µm, greater than 10 µm, greater than 50 µm, greater than 100 µm or greater than 1000 µm.

37. The method of any of embodiments 1-36, wherein one or more of the non-cell particles, optionally one or more beads, has a diameter of 1.0 µm to 500 µm, 1.0 µm to 150 µm, 1.0 µm to 30 µm, 1.0 µm to 10 µm or 1.0 µm to 5.0 µm.

38. The method of any of embodiments 1-37, wherein one or more of the non-cell particles, optionally one or more beads, has a diameter that is substantially the same as the average diameter of a cell in the cell composition or is within 5-fold, 4-fold, 3-fold, 2-fold or 1.5-fold greater or less than the average diameter of a cell in the cell composition.

39. The method of any of embodiments 1-38, wherein the one or more particles, optionally one or more beads, has a diameter that is or is about the same size as a lymphocyte or an antigen presenting cell.

40. The method of any of embodiments 1-39, wherein the one or more non-cell particles, optionally one or more beads, has a diameter of greater than or greater than about 3.5 µm but no more than about 9 µm or no more than about 8 µm or no more than about 7 µm or no more than about 6 µm or no more than about 5 µm.

41. The method of any of embodiments 1-40, wherein the one or more non-cell particles, optionally one or more beads, comprises a diameter of or about 4.5 µm.

42. The method of any of embodiments 1-41, wherein one or more of the non-cell particles, optionally one or more beads, comprise a core, optionally a magnetic core, a paramagnetic core or a superparamagnetic core.

43. The method of any of embodiments 1-42, wherein one or more of the non-cell particles, optionally one or more beads, comprise a superparamagnetic core.

44. The method of embodiment 42 or embodiment 43, wherein the core is selected from among metal oxides, ferrites, metals, hematite, metal alloys, and combinations thereof.

45. The method of any of embodiments 1-44, wherein the one or more non-cell particles, optionally one or more beads, is inert.

46. The method of any of embodiments 1-45, wherein the one or more non-cell particles, optionally one or more beads, is or comprises a polystyrene surface, and optionally comprises a magnetic or superparamagnetic core.

47. The method of any of embodiments 23-46, wherein the one or more biomolecule comprise antibodies and/or are present on the surface of the one or more non-cell particles, optionally the one or more bead.

48. The method of any of embodiments 23-47, wherein the one or more biomolecule is an affinity agent capable of selecting, isolating or enriching one or more cells in a sample or is a stimulatory agent or agents capable of stimulating one or more cells in the sample.

49. The method of any of embodiments 23-48, wherein the macromolecule is a cell surface protein.

50. The method of embodiment 48 or embodiment 49, wherein the stimulatory agent or agents is capable of activating one or more intracellular signaling domains of one or more components of a TCR complex and/or one or more intracellular signaling domains of one or more costimulatory molecules.

51. The method of any of embodiments 48-50, wherein the stimulatory agent or agents comprises a primary agent that specifically binds to a member of a TCR complex and a secondary agent that specifically binds to a T cell costimulatory molecule.

52. The method of embodiment 51, wherein the primary agent specifically binds to CD3 and/or the costimulatory molecule is selected from the group consisting of CD28, CD137 (4-1-BB), OX40, or ICOS.

53. The method of embodiment 51 or embodiment 52, wherein the primary agent is or comprises anti-CD3 and the secondary agent is or comprises anti-CD28.

54. The method of any of embodiments 1-53, wherein the one or more cells has a diameter of between or about between 10 μm and 30 μm.

55. The method of any of embodiments 1-54, wherein the one or more cells is an animal cell or the cell composition comprises animal cells.

56. The method of any of embodiments 1-55, wherein the one or more cells is a human cell or the cell composition comprises human cells.

57. The method of any of embodiments 1-56, wherein the one or more cells is a stem cell or the cell composition comprises stem cells.

58. The method of embodiment 57, wherein the stem cell is an induced pluripotent stem cell (iPSC).

59. The method of any of embodiments 1-58, wherein the one or more cell is an immune cell or the cell composition comprises immune cells.

60. The method of embodiment 59, wherein the immune cell is a T cell, B cell, macrophage, neutrophil, natural killer (NK) cell or dendritic cell.

61. The method of any of embodiments 1-60, wherein the one or more cells have been mixed with one or more of the non-cell particles, wherein the non-cell particle comprises a stimulating agent or agents to effect stimulation and/or activation of a cell in the cell composition prior to the incubating.

62. The method of embodiment 61, wherein the cell is a T cell and the stimulating agent or agents is an anti-CD3 antibody and/or anti-CD28 antibody or an antigen-binding fragment thereof.

63. The method of any of embodiments 1-60, wherein the one or more cells have been mixed with one or more of the non-cell particles, wherein the non-cell particle comprises one or more affinity reagent to effect selection, isolation or enrichment of a cell from a cell composition prior to the incubating.

64. The method of embodiment 48 or embodiment 63, wherein the affinity reagent comprises an antibody or antigen-binding fragment thereof that specifically binds to a cell surface protein on the one or more cells.

65. The method of embodiment 64, wherein the cell surface protein is selected from among CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1), CD62L (L-selectin), CD29/CD49d (VLA-4), a Notch ligand, Delta-like 1/4, Jagged 1/2, CCR1, CCR2, CCR3, CCR4, CCR5, CCR7, and CXCR3.

66. The method of any of embodiments 1-65, wherein the incubating is performed at a temperature that is about 15° C. to 30° C., 18° C. to 28° C. or 20° C. to 25° C.

67. The method of any of embodiments 1-66, wherein the incubating is performed at a temperature that is about 23° C.

77. An article of manufacture, comprising:
a container comprising a solution comprising bleach and/or detergent for effecting cell lysis;
packaging material; and
a label or package insert comprising instructions for detecting the presence or absence of particles in a cell composition; wherein the instructions specify the steps of:
a) incubating a sample comprising at least a portion of an input composition or a sample derived from the input composition, said input composition comprising one or more cells and one or more non-cell particles, wherein the incubating is with the solution under conditions to induce lysis of cells to produce an output composition;
b) analyzing the output composition or a portion thereof by fluorescence imaging to determine the presence or absence of particles in the sample.

78. The article of manufacture of embodiment 77, wherein the instructions specify the analyzing the output composition by fluorescence imaging comprises obtaining fluorescent micrographs of the output composition or a portion thereof, and optionally determining the fluorescent intensity of image objects from the fluorescent micrographs.

79. The article of manufacture of embodiment 77 or embodiment 78, wherein the instructions specify further obtaining brightfield micrographs of the output composition or a portion thereof.

80. The article of manufacture of embodiment 78 or embodiment 79, wherein the instructions specify the analyzing the output composition further comprises determining the size, area, and/or circularity of image objects from the fluorescent micrographs or brightfield micrographs.

81. An article of manufacture, comprising:
a container comprising a solution comprising bleach and/or detergent for effecting cell lysis;
packaging material; and
a label or package insert comprising instructions for detecting the presence or absence of particles in a cell composition; wherein the instructions specify the steps of:
(i) illuminating an output composition or a portion thereof with one or more light sources to generate an illuminated sample, wherein at least one light source is capable of exciting fluorescent molecules;
(ii) capturing one or more images of the illuminated sample, wherein at least one image is a fluorescent image;
(iii) analyzing the presence or absence of image objects from the one or more images for one or more parameters selected from size, area, fluorescent intensity (FI), brightfield intensity, and/or circularity;
wherein the output composition is produced by incubating a sample comprising at least a portion of an input composition or a sample derived from the input composition, said input composition comprising one or more cells and one or more non-cell particles, wherein the incubating is with the solution under conditions to induce lysis of cells to produce an output composition.

82. An article of manufacture, comprising:
a container comprising a solution comprising bleach and/or detergent for effecting cell lysis;
packaging material; and
a label or package insert comprising instructions for detecting the presence or absence of particles in a cell composition; wherein the instructions specify the steps of:
  a) incubating a sample comprising at least a portion of an input composition or a sample derived from the input composition, said input composition comprising one or more cells and one or more non-cell particles, wherein the incubating is with the solution under conditions to induce lysis of cells to produce an output composition;
  b) optically analyzing the output composition or portion thereof to assess the presence or absence of one or more parameters of one or more image objects, wherein the one or more parameters is selected from size, area, fluorescent intensity (FI), brightfield intensity, and/or particle circularity.

83. The article of manufacture of any of embodiments 77-82, wherein:
the output composition does not comprise an agent for detecting the particles, optionally wherein the agent is or comprises a detectable moiety or is capable of producing a detectable; signal; or
the instructions specify the analyzing does not comprise adding an agent for detecting the particles to the output composition, optionally wherein the agent is or comprises a detectable moiety or is capable of producing a detectable signal.

84. The article of manufacture of any of embodiments 77-80, wherein the instructions further specify prior to the analyzing, the output composition is enriched for the one or more non-cell particles.

85. The article of manufacture of embodiment 81, wherein the instructions further specify prior to the illuminating the output composition is enriched for the one or more non-cell particles.

86. The article of manufacture of embodiment 82, wherein the instructions further specify prior to the analyzing the output composition is enriched for the one or more non-cell particles.

87. The article of manufacture of any of embodiments 77-86, wherein:
the one or more non-cell particles are autofluorescent; and/or
the instructions further specify the steps are carried out on a sample or composition that may contain non-cell particles that are autofluorescent.

88. The article of manufacture of any of embodiments 78 and 80-, wherein the instructions specify a non-cell particle is detected if:
  (i) the image object comprises a circularity of at or at least 0.5, 0.6, 0.7, 0.8, or 0.9;
  (ii) the image object comprises a diameter of between 5 µm and 10 inclusive; and/or
  (iii) the image object comprises an area of between 25 µm$^2$ and 50 µm$^2$;
  (iv) the image object comprises a fluorescent signal, optionally above a background signal in a control sample; and/or
  (v) the image object comprises a florescent intensity (FI), optionally wherein the FI is greater than a background signal in a control sample.

89. The article of manufacture of embodiment 88, wherein the control sample is composition produced by incubating a cell composition comprising the one or more cells but not comprising, or not likely comprising, the one or more non-cell particles, wherein the incubating is under conditions to induce lysis of cells to produce an output composition.

90. The article of manufacture of any of embodiments 77-89, wherein the detergent is one or more of Triton X-100, Triton X-114, NP-40, Brij-35, Brij-58, Tween 20, Tween 80, digitonin, octyl glucoside, octyl thioglucoside, sodium dodecyl sulfate (SDS), 3-[(3-cholamidopropyl)dimethylammonio]-1-propanesulfonate (CHAPS) and CHAPSO.

91. The article of manufacture of any of embodiments 77-90, wherein the bleach is a chlorine-based bleach.

92. The article of manufacture of any of embodiments 77-91, wherein the sample is incubated with bleach at a concentration of about 0.1%, 0.2%, 0.3%, 0.4%, 0.5%, 1%, 1.5%, 2%, 3%, 4%, 5%, 6%, 7% or 8% (v/v) bleach, or a range defined by any two of the foregoing values.

93. The article of manufacture of any of embodiments 77-92, wherein the one or more particles are one or more beads.

VII. Examples

The following examples are included for illustrative purposes only and are not intended to limit the scope of the invention.

Example 1: Cell Lysis and Automated Residual Beads Enumeration

An exemplary automated (automatic fluorescent) method was used to quantify the number of non-cell particles, particularly bead particles, present in a cell composition that had been incubated in the presence of bead particles. In some aspects, cell compositions, e.g., containing T cells engineered to express a recombinant receptor for administration to a subject for adoptive cell therapy, can be generated using process that involves incubation of cells with bead particles to which is attached antibodies or antigen binding fragment thereof for stimulation and/or for enrichment of particular cells in the cell composition. In some aspects, the process also involves removal of bead particles after such incubation. In some aspects, the exemplary automated methods can be used to enumerate residual beads that are present in the cell composition, such as beads that remain in the sample after removal steps. Detection is facilitated by fluorescent methods, such as when particular types of beads in the process for engineering cells exhibit inherent autofluorescent properties, e.g. such as present in 4.5 µM diameter superparamagnetic polystyrene bead particles conjugated to anti-CD3/anti-CD28 used for cell stimulation or activation. In some cases, the exemplary method can be used to determine the efficiency of removal of the bead particles in order to facilitate identification of engineered cell compositions that may contain residual beads above a threshold level in order to reduce adverse or toxic effects that can result due to such levels, e.g. as a result from incomplete removal of the bead particles.

The exemplary automated fluorescent method described in this Example was used to determine the number of bead particles present in cell compositions containing a defined number of beads, to assess the suitability of the exemplary method for enumeration of residual beads in engineered cell compositions.

A. Samples

Cryopreserved engineered CD4+ or CD8+ T cell compositions from human donors, containing primary T cells engineered to express a chimeric antigen receptor (CAR) were used in the exemplary method. The engineered cell compositions were generated from primary CD4+ or CD8+ T cells isolated from the donors that were stimulated in the presence of paramagnetic polystyrene-coated bead particles coated with anti-CD3 and anti-CD28 antibodies prior to introduction of nucleic acids encoding a CAR, followed by a step to remove the bead particles by exposure to a magnetic field. After the engineering steps, the resulting cell compositions containing engineered cells were cryopreserved, thawed, pooled and mixed (spiked) with a defined number of bead particles to assess the specificity, linearity, accuracy, precision and range of the method.

Solutions containing various concentrations of 4.5 μM diameter superparamagnetic polystyrene bead particles were prepared by dilution of the manufacturer's preparation (concentration: approximately 400,000 Beads/μL), in 1× phosphate-buffered saline with 0.1% Tween-20 (PBST). Several further diluted solutions containing different bead particle concentrations were prepared, by adding vortexed bead solutions into a defined volume of PBST. The concentration of bead particles in the various solutions were assessed using an automated fluorescence imaging system of bead particle autofluorescence to confirm the concentration of the bead particles, by assessing 20 replicates of 50 μL of each of the bead solutions into separate wells of a 384-well plate. The average bead count from the assessment was used to calculate the bead particle concentration of the prepared bead solutions.

Based on the calculated concentrations, a specific volume of one of the bead solutions was added to thawed CD4+ engineered cell compositions generated as described above ($5 \times 10^7$/mL cell concentration), to obtain bead and cell mixtures containing the following spiked bead concentrations: 600 Beads/mL; 400 Beads/mL; 300 Beads/mL; 200 Beads/mL; 100 Beads/mL; 50 Beads/mL and 0 Beads/mL. For analysis using cell compositions containing different T cell subtypes, a CD8+ engineered cell composition generated as described above, was spiked with bead particles at a concentration of 400 Beads/mL (see Example 1.H below). For analysis using cell compositions containing a higher concentration of cells, a CD8+ engineered cell composition at $7 \times 10^7$ cells/mL, was spiked with bead particles at a concentration of 400 Beads/mL (see Example 1.1 below).

B. Lysis and Bead Enumeration

Thawed engineered cell compositions containing the spiked bead particles as described above, were mixed by vortexing and subject to lysis and automated (automatic fluorescent) bead enumeration. 400 μL of the cell compositions containing spiked beads were centrifuged for 1200×g for 2 minutes to recover cells and bead particles. After removing the supernatant, the centrifuged samples were resuspended in a lysis buffer (800 μL 1× phosphate-buffered saline with 0.1% Tween-20 (PBST); 200 μL of 8.25% bleach) and incubated for approximately 2 minutes at room temperature. Lysed samples were placed on a magnet designed for the paramagnetic polystyrene beads for 2 minutes, to separate the paramagnetic bead particles from cell debris. The supernatant was removed, and the residual beads from the sample were washed twice with 1 mL PBST. The washed beads were resuspended in 75 μL PBST (sample beads), and loaded onto a well in a 384-well plate. Another 75 μL of PBST was used to rinse the sides of the test tubes (wash beads) and loaded onto another well of the 384-well plate.

Images from the samples in the 384-well assay plate were collected with Cytation™ 5 Cell Imaging Multi-Mode Reader (BioTek Instruments, Inc., Winooski, VT) using both a brightfield and a Cy5 fluorescent filter channels at 10× magnification, then overlaid and processed to reduce background interference. Beads that exhibited autofluorescence using the fluorescent filter could be detected. Beads in the images were distinguished from cells or other debris visually and automatically using the image processing software Gen5 on the imaging platform, based on size, fluorescent signal, area, and circularity, to count the number of bead particles in the sample and to calculate the concentration of the beads in a given sample. An exemplary method for detecting and enumerating beads involved a first, optional parameter that was applied using the brightfield channel to select for image objects that were between 3 and 15 μm in size. A second parameter was applied using the fluorescent filter channel to select for image objects that were between 1 and 5 μm in size. Once image objects were identified and selected for based on size, image objects were further identified as being either single non-particle cells ("singlets") or double non-particle cells ("doublets"), based on the value thresholds in Table 1a. The total number of beads/mL in each sample were calculated by (number of sample beads+number of wash beads)/0.4 mL=total number of beads/mL.

TABLE 1a

Software-Based Automatic Detection of Beads

| Type of Image Object | Characteristic | Detection Threshold |
|---|---|---|
| Singlets and/or Doublets | Size: Brightfield Mask (optional) | 3-15 μm |
| | Size: Fluorescent Mask | 1-5 μm |
| Singlets | Fluorescent | Yes; AND |
| | Circularity | 0.7-1.0; AND |
| | Area | Less than 65 μm$^2$ |
| Doublets | Fluorescent | Yes; AND |
| | Circularity | >0.4 and <0.6; AND |
| | Area | Less than 130 μm$^2$ |

Additional experiments were carried out in which lysed samples (containing thawed engineered cell compositions that were spiked with 400 bead particles/mL) were placed on a magnet for separation of paramagnetic bead particles as described above, but in which the exposure to the magnet was carried out for different lengths of time (e.g., 30 seconds, 2 minutes or 60 minutes). The residual beads present in the sample after the magnetic separation was assessed from an average of at least three samples using the automated (automatic fluorescent) imaging method described above. For all assessed samples, the results revealed that the average determined residual bead count after incubation with the magnet for the different lengths of time were each within an acceptance criteria of coefficient of variation (CV)≤25%, although the average bead count after incubation of the sample with the magnet for 60 minutes resulted in fewer recovered beads than the other timepoints.

C. Assessment of Specificity

The specificity of the method was evaluated by analyzing the bead count in three independent vials of CD4+ engineered cell compositions without any added bead particles (0 Beads/mL spiked beads). The engineered cell compositions without added bead particles were expected to contain no residual beads. As shown in Table 1b, the bead concentration in all 3 vials was below the limit of quantitation (LOQ) of the method. No significant interference from system artifacts or the engineered cell composition was observed.

TABLE 1b

Assessment of Specificity.

| Sample | Vial No. | Observed bead concentration (Beads/mL) |
|---|---|---|
| CD4+ CAR+ cell composition without added bead particles | 1 | <LOQ |
|  | 2 | <LOQ |
|  | 3 | <LOQ |

D. Assessment of Linearity

Linearity of the method was assessed by determining the correlation between the observed bead concentrations and the expected concentration of the beads in the samples being analyzed. In some aspects, linearity can refer to the ability (within a given range) to obtain test results that are directly proportional to the concentration (amount) of the analyte in the sample. The bead concentration in engineered cell compositions containing 600, 400, 300, 200, 100 and 50 beads/mL of spiked beads, independently prepared in triplicate, was assessed as described in this Example.

Figure 2A:
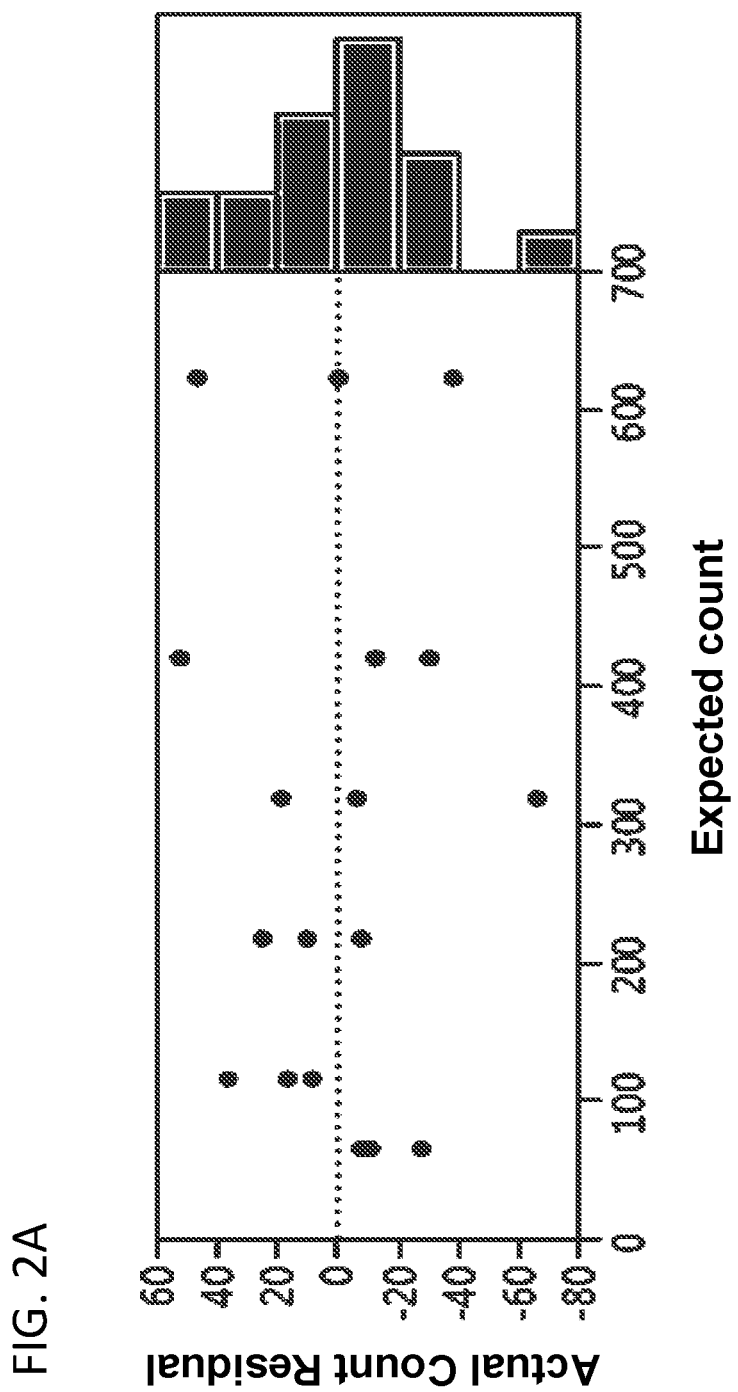
FIG. 2A shows a plot of the residual values (expected count subtracted from actual count) at each target concentrations (expected counts). The dotted horizontal line indicates the residual value of 0.
Figure 2B:
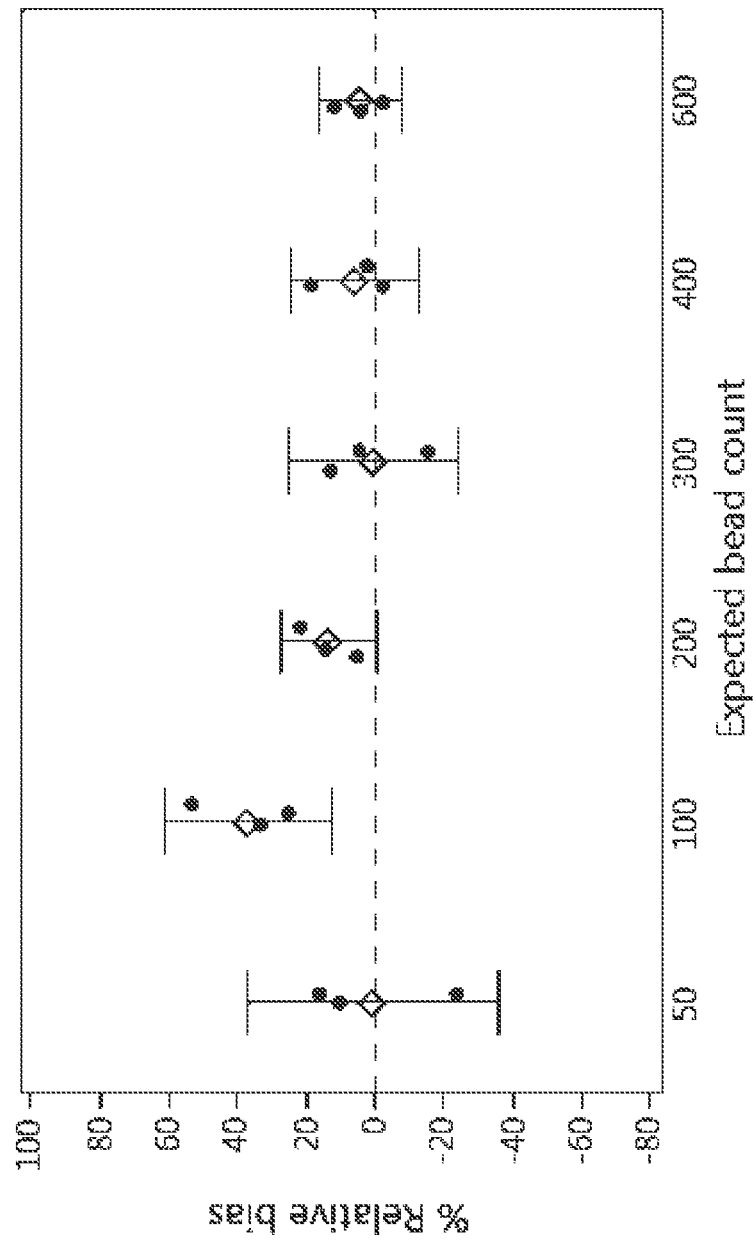
FIG. 2B shows a plot of the actual bead counts compared to expected bead counts at each target concentration. Diamond symbols represent the mean of three actual bead counts and the bars represent 90% confidence intervals of the mean at each target concentration.

As shown in FIG. 1, a plot of the bead concentrations in the triplicate samples at each target concentration showed a linear relationship described by the equation: actual count=15.4+1.01× expected count. The coefficient of determination ($R^2$) was 0.98; the root mean squared error (RMSE) was 31.3; the intercept of the linear model was 15.4, with a confidence interval of (−12.4, 43.3); and the slope was 1.01, with a confidence interval of (0.93, 1.10). As shown in FIG. 2A, in the entire range of the bead concentration of (50, 100, 200, 300, 400, and 600 beads/mL), the model residual (actual count expected count) did not show a systematic trend, and was evenly distributed around zero. The results were consistent with an observation that the model described a linear relationship between the actual and expected bead counts. As shown in FIG. 2B, relative bias was determined to examine patterns in the experimental results, and was calculated by comparing the actual bead count to the expected bead count. In agreement with other analyses, there was not a trend in relative bias across levels. A positive bias at the expected bead count of 100 was observed, though this may have been caused by a spiking error.

E. Assessment of Precision

Repeatability and precision of the method, including intermediate precision, was assessed. In some aspects, precision can refer to the closeness of agreement between a series of measurements. Precision of the method was assessed by determining the standard deviation and/or the relative standard deviation (% coefficient of variation) of a series of measurements. Contributions of qualification study factors to the precision of the assay were determined by performing variance component analysis on the prediction experimental results. Variance component analysis was carried out using the JMP® Pro (SAS Institute, Inc.) to perform a mixed-model analysis with restricted maximum likelihood estimation (REML).

Repeatability of the method and intermediate precision was determined from three independently prepared vials per run for multiple target concentrations (50, 100 and 400 beads/mL). The samples were prepared and analyzed by two different operators, independently, in two separate runs. Each vial was independently prepared and analyzed once, resulting in a total of twelve bead counts over four runs for each of the target concentrations. Three independently prepared vials at three additional target concentrations (200, 300 and 600 beads/mL) were analyzed by one analyst on a single day. Each vial was independently prepared and analyzed once resulting in a total of three bead counts from one run for each of the target concentrations.

Figure 3:
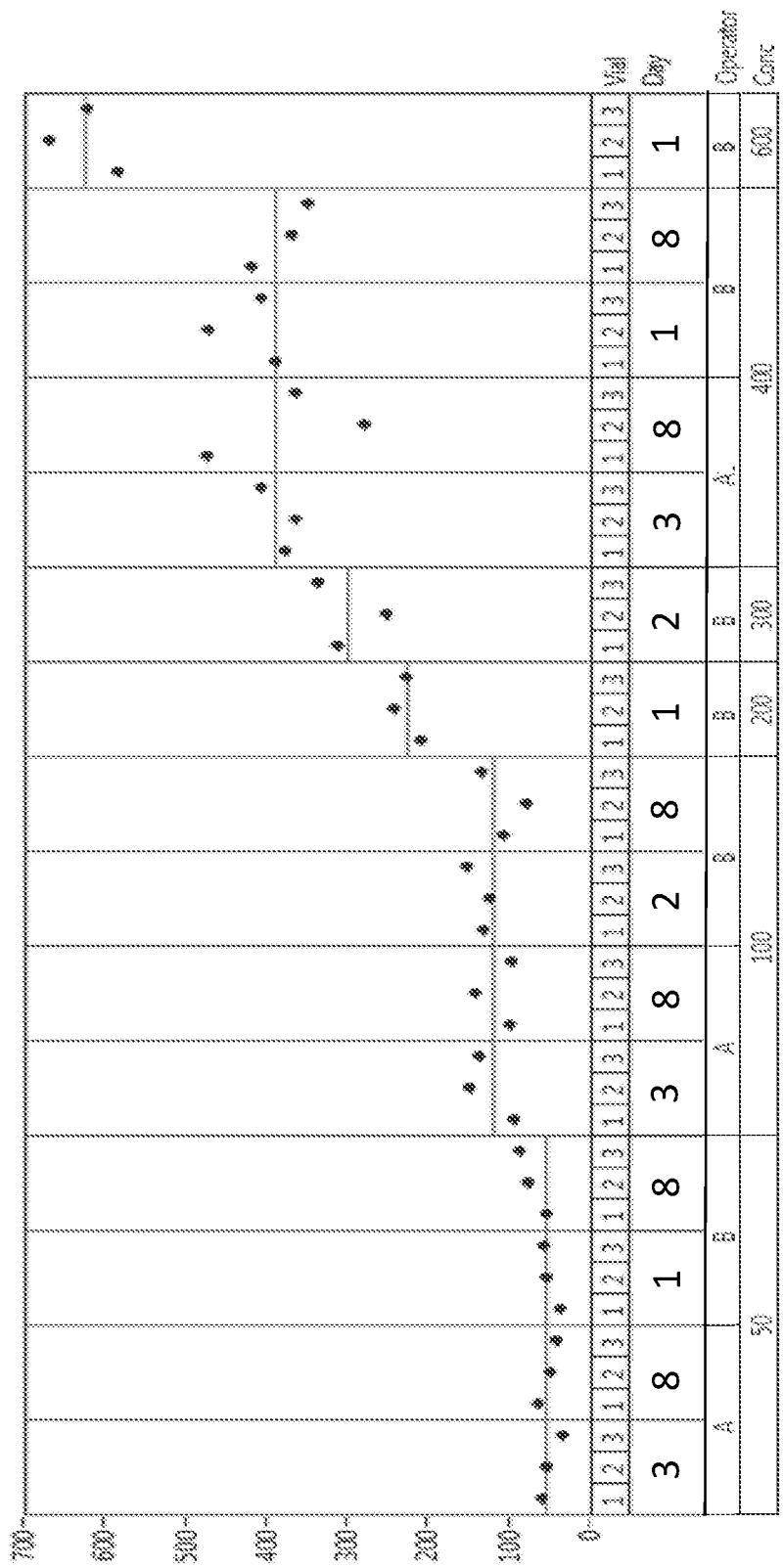
FIG. 3 shows the individual measurements of bead counts from individual vials (vials 1-3), on different experimental days (days 1, 2, 3 or 8), with different operators (A or B), at different target concentrations (conc). Solid horizontal lines indicate mean bead counts for each concentration.

FIG. 3 shows the variability of measured bead counts in each experimental condition, in a nested hierarchy, with the solid lines indicating mean bead counts at each concentration. The mean, standard deviation (SD) and coefficient of variation (CV) of the measurements are set forth in Table 2.

TABLE 2

Summary statistics of independent repeats of bead counts.

| Concentration | Operator | Day | Mean | SD | CV (%) |
|---|---|---|---|---|---|
| 50 | A | 3 | 50 | 13 | 26 |
|  |  | 8 | 53 | 11 | 21 |
|  | B | 1 | 50 | 11 | 21 |
|  |  | 8 | 74 | 17 | 23 |
| 100 | A | 3 | 128 | 29 | 23 |
|  |  | 8 | 114 | 25 | 22 |
|  | B | 2 | 137 | 14 | 11 |
|  |  | 8 | 108 | 28 | 26 |
| 200 | B | 1 | 227 | 17 | 7 |
| 300 | B | 2 | 301 | 44 | 14 |
| 400 | A | 3 | 384 | 22 | 6 |
|  |  | 8 | 373 | 98 | 26 |
|  | B | 1 | 424 | 44 | 10 |
|  |  | 8 | 380 | 36 | 9 |
| 600 | B | 1 | 626 | 43 | 7 |

A nested mixed effect model that included both random factors (operator, day and vial, and fixed factors (material; different concentrations) was used for precision analysis. The variance components were represented as follows: $\sigma_T^2 = \Sigma_{O(M)}^2 + \sigma_{D(M,O)}^2 + \sigma_e^2$, where $\sigma_T^2$, $\sigma_{O(M)}^2$, $\sigma_{D(M,O)}^2$ and $\sigma_e^2$ represented total, operator, day and residual (vial) variances, respectively. Table 3 sets forth precision (repeatability and intermediate precision) of the method based on variance component analysis. In some aspects, variance of all bead count measurements include the variations due to all the factors (operator, day and vial), and is the intermediate precision. Repeatability is the variation in bead counts among vials.

As shown in Table 3, repeatability of the method was observed to be 0% CV and the intermediate precision was observed to be 15.4% CV. No effect of operator and day on assay precision was observed, and only vial-to-vial variation in bead count was significant.

TABLE 3

Precision (repeatability and intermediate precision) using variance component analysis.

| Random Effect | Variance Component | % of Total | CV (%) |
|---|---|---|---|
| Operator [Concentration] | 0 | 0 | 0 |
| Day [Concentration, Operator] | 0 | 0 | 0 |
| Residual | 1236 | 100 | 15.4 |
| Total | 1236 | 100 | 15.4 |

F. Assessment of Accuracy

Accuracy of the method, which in some aspects can be defined as the closeness of agreement between true value/accepted reference value and the value determined by the method, was assessed. In the described exemplary (automatic fluorescent) method, as part of the data analysis, the software provided an automated bead count value based on parameters set to distinguish a bead from other debris or artifacts. Accuracy of the exemplary method was assessed by visual inspection and manual enumeration by a human operator from the raw images collected during the quantification process. Values obtained from manual enumeration by a human operator were compared to the automatic bead count determined by the software. Accuracy of the automated bead count at each target bead concentration was reported as percent recovery calculated as follows: % Recovery=100%×(Automatic Bead Count/Manual Bead Count)

Table 4 sets forth the percent recovery across independent vials of CAR+ cell compositions spiked with several different bead concentrations. The percent recovery across all bead concentrations was observed to be between 88-110%. The results showed that automated bead count provided by the software used in the method was accurate and the parameters selected in the exemplary method were suitable for determining the number of bead particles present in the samples.

TABLE 4

Accuracy of the Automated Bead Enumeration Method.

| Sample | Vial No. | Observed automatic bead count | Observed manual bead count | Recovery (%) |
|---|---|---|---|---|
| Composition Spiked with 600 Beads/mL | 1 | 234 | 244 | 96 |
|  | 2 | 268 | 269 | 100 |
|  | 3 | 249 | 250 | 100 |
| Composition Spiked with 400 Beads/mL | 1 | 156 | 164 | 95 |
|  | 2 | 189 | 206 | 92 |
|  | 3 | 163 | 156 | 104 |
| Composition Spiked with 300 Beads/mL | 1 | 125 | 132 | 84 |
|  | 2 | 101 | 108 | 94 |
|  | 3 | 135 | 148 | 91 |
| Composition Spiked with 200 Beads/mL | 1 | 84 | 88 | 95 |
|  | 2 | 97 | 110 | 88 |
|  | 3 | 91 | 95 | 96 |
| Composition Spiked with 100 Beads/mL | 1 | 53 | 51 | 104 |
|  | 2 | 50 | 50 | 100 |
|  | 3 | 61 | 68 | 90 |
| Composition Spiked with 50 Beads/mL | 1 | 15 | 15 | 100 |
|  | 2 | 22 | 20 | 110 |
|  | 3 | 23 | 26 | 88 |

G. Assessment of Range

As described above, the tested samples contained a range of 50 to 600 spiked beads/mL. The performance of this method was evaluated by assessing the precision and accuracy of the method. Acceptable values for precision (see Tables 2 and 3 and FIG. 3) and accuracy (Table 4) were observed, demonstrating acceptable performance of the method within the range of the concentrations evaluated, of 50 to 600 spiked beads/mL. Thus, the results showed that the methods can be used to enumerate residual beads with acceptable accuracy and precision, for example, for CAR+ T cell compositions to meet the manufacturing process requirements for residual bead count.

H. Performance of Method Using CD8+ CAR+ Cell Composition

The method was performed using CD8+ CAR+ cell compositions, to confirm whether the results are affected by the subtypes of cells present in the composition (CD4+ CAR+ cell compositions and CD8+ CAR+ cell compositions). Three samples of a CD8+ CAR+ cell composition were spiked with bead particles at a concentration of 400 Beads/mL and were independently analyzed using the exemplary method described above. Results are set forth in Table 5. The average observed bead concentration (beads/mL) was 407, the standard deviation (SD) was 51, and the % relative standard deviation (RSD) was 13. Recovery values ranged from 87-110% and a low variation was observed, with the RSD value of 13%. The results showed that the performance of the method was not impacted by the types of cells in the composition.

TABLE 5

Results from Analysis of CD8+ CAR+ Compositions.

| Sample | Vial No. | Observed automatic bead concentration (Beads/mL) | Theoretical bead concentration | Recovery (%) |
|---|---|---|---|---|
| CD8+ CAR+ cell composition spiked with 400 Beads/mL | 1 | 440 | 400 | 110 |
|  | 2 | 433 |  | 108 |
|  | 3 | 348 |  | 87 |

I. Performance of Method with Higher Cell Density

The method was performed using cell compositions containing higher cell density, to confirm whether the results are affected by the density of cells present in the composition. Three samples of a CD8+ CAR+ cell composition, at a higher cell density ($7 \times 10^7$ cells/mL; compared to compositions described above containing $5 \times 10^7$ cells/mL), was spiked with bead particles at a concentration of 400 Beads/mL and were independently analyzed using the exemplary method described above. Results are set forth in Table 6. The average observed bead concentration (beads/mL) was 370, the standard deviation (SD) was 45, and the % relative standard deviation (RSD) was 12. Recovery values ranged from 83-105% and a low variation was observed, with the RSD value of 12%. The results showed that the performance of the method was not impacted by a higher cell concentration in the composition, e.g., of up to $7 \times 10^7$ cells/mL.

TABLE 6

Results from Analysis of Compositions Containing Higher Cell Density.

| Sample | Vial No. | Observed automatic bead concentration (Beads/mL) | Theoretical bead concentration | Recovery (%) |
|---|---|---|---|---|
| High cell density CAR+ cell composition spiked with 400 Beads/mL | 1 | 420 | 400 | 105 |
|  | 2 | 358 |  | 89 |
|  | 3 | 333 |  | 83 |

J. Comparison with a Different (Manual) Method of Bead Enumeration

The exemplary (automatic fluorescent) method described above was compared to the bead enumeration results from a different (manual) method that involves similar sample preparation steps but does not utilize automated detection and enumeration, but instead involves manual identification and counting of beads. Independent triplicates of CAR+ cell compositions, each containing one of six concentrations of spiked bead particles (600, 400, 300, 200, 100 and 50 beads/mL) were assessed using the exemplary (automatic fluorescent) method described above ("Method 1"), and one additional vial of each sample was assessed using the different (manual) method ("Method 2"). Regression analysis was performed to estimate the equivalence/difference between bead counts using Method 1 ("Method 1 count") and Method 2 ("Method 2 count").

Figure 4A:
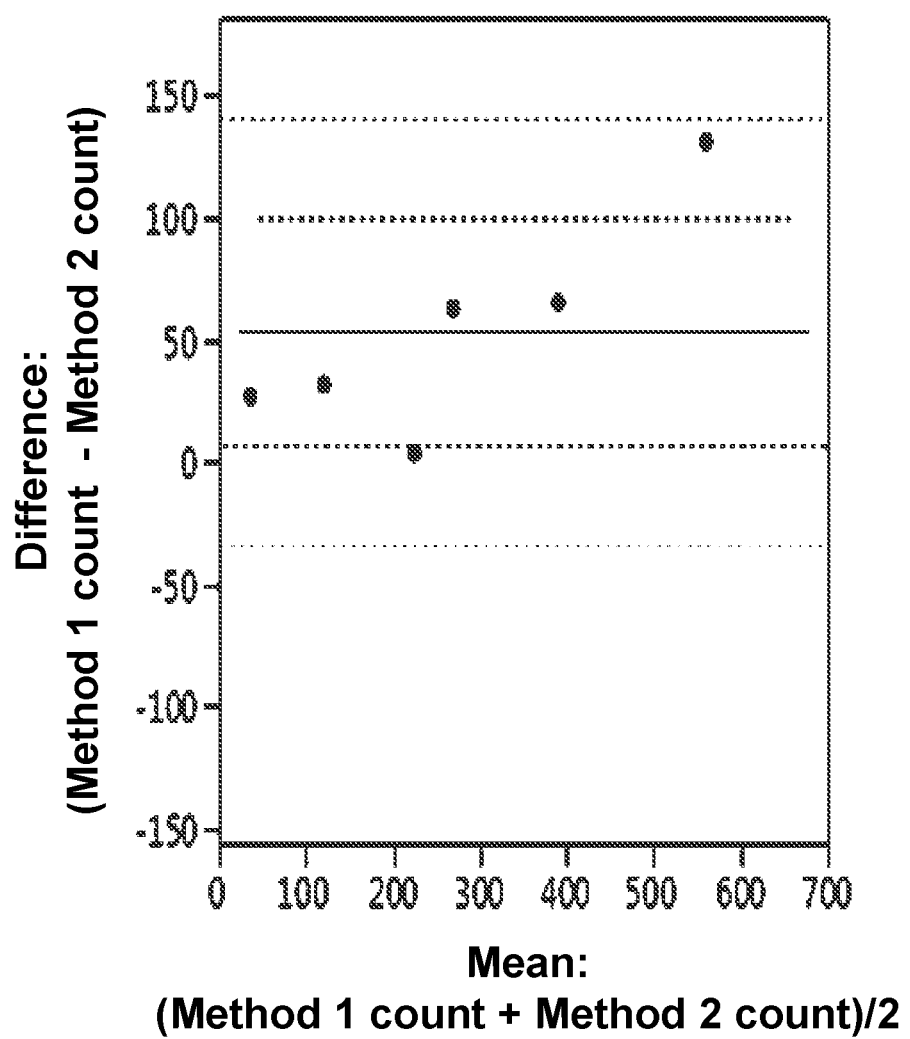
FIGS. 4A and 4B compare bead counts in spiked cell compositions by two different methods.
Figure 4B:
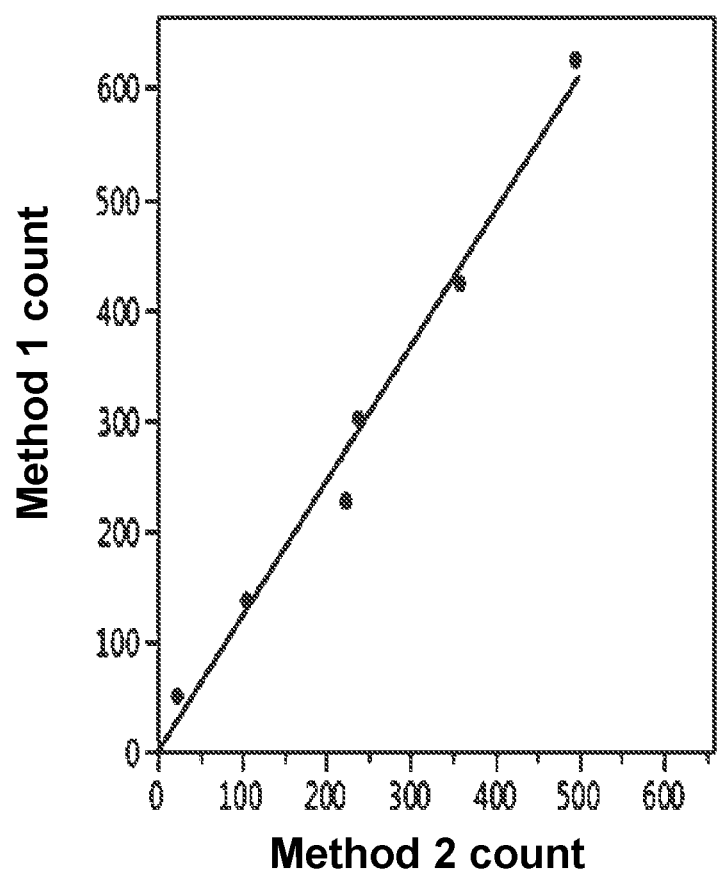

The results of comparing the bead counts using the two methods are shown in FIGS. 4A and 4B. As shown in a plot of the difference between Method 1 (automatic fluorescent method) count and Method 2 (manual method) count vs. mean bead counts using the two methods in FIG. 4A, Method 1 count was slightly higher than Method 2 count. FIG. 4B shows the error-in-variable regression between Method 1 (automatic fluorescent method) count and Method 2 (manual method) count using 6 paired values. As shown, the regression model was as follows: Method 1 count=1.2× Method 2 count 0.2. The 95% confidence interval of the slope was (1.03, 1.46), and the concordance correlation coefficient (CCC) between Method 1 count and Method 2 count was observed to be 0.93, with the 95% confidence interval of (0.74, 0.98). Both the error-in-variable regression and the CCC were consistent with the observation that the bead concentrations determined using Method 1 were slightly higher than those determined using Method 2.

K. Evaluation of Positive Controls

Prior to assessment of the methods described above, a bank of single use aliquots of positive control was prepared that did not contain any cells. The positive control aliquots were prepared by vortexing the bead particle solutions containing various concentrations of beads described in Example 1.A above, placing 30 µL of each solution to separate tubes and adding 400 µL of PBST or CS-10 Freeze Media (BioLife) to each tube. The positive control sample was prepared and analyzed along with every batch of samples tested in this Example. The % recovery of the positive control samples were used to evaluate the aspects of the methods. In addition, the positive control samples were independently prepared and analyzed by two different operators, with three positive controls per run for a total of fifteen positive control vials across multiple days. The data from the studies described above and the positive control vials was used to set a tolerance interval for the positive controls.

TABLE 7

Assessment of Positive Controls.

| Run | Control | Observed bead count | Average observed bead count | Standard deviation | CV (%) |
|---|---|---|---|---|---|
| 1 | 1 | 134 | 137 | 10 | 8 |
|  | 2 | 128 |  |  |  |
|  | 3 | 148 |  |  |  |
| 2 | 1 | 133 | 108 | 23 | 21 |
|  | 2 | 103 |  |  |  |
|  | 3 | 88 |  |  |  |
| 3 | 1 | 106 | 97 | 10 | 10 |
|  | 2 | 87 |  |  |  |
|  | 3 | 97 |  |  |  |
| 4 | 1 | 122 | 113 | 20 | 18 |
|  | 2 | 90 |  |  |  |
|  | 3 | 126 |  |  |  |

TABLE 7-continued

Assessment of Positive Controls.

| Run | Control | Observed bead count | Average observed bead count | Standard deviation | CV (%) |
|---|---|---|---|---|---|
| 5 | 1 | 85 | 99 | 13 | 13 |
|  | 2 | 100 |  |  |  |
|  | 3 | 111 |  |  |  |
| Overall Average Bead Count |  | 111 | Tolerance interval (1-alpha = 0.95; 90%, two-sided) | | 61-161 beads |
| Overall Standard Deviation |  | 20 | | | |
| Overall CV (%) |  | 18 | | | |

L. Conclusion

The exemplary automated residual beads enumeration method described in this Example was demonstrated to be a specific, linear, precise, accurate and suitable method for determining the number of residual beads in engineered cell compositions.

Example 2: Comparison of Methods for Detecting Residual Beads in Engineered CAR+ Therapeutic T Cell Composition Using Automatic Fluorescent Versus Manual Bead Enumeration Methods Cryopreserved engineered CD4+ or CD8+ T cell compositions were generated from primary CD4+ or CD8+ T cells isolated from human donors by a process involving subjecting enriched CD4+ and enriched CD8+ cell populations, separately, to process steps. CD4+ and CD8+ cells were separately selected from human peripheral blood mononuclear cells (PBMCs) that had been obtained by leukapheresis, generating separate enriched CD4+ and enriched CD8+ cell compositions, which then were cryofrozen. The CD4+ and CD8+ compositions were subsequently thawed and separately underwent steps for stimulation, transduction, and expansion. Specifically, the thawed CD4+ and CD8+ cells were separately stimulated in the presence of paramagnetic polystyrene-coated beads (4.5 µM diameter) coupled to anti-CD3 and anti-CD28 antibodies and recombinant human cytokines (e.g. IL-2, IL-7 and/or IL-15) and then were separately transduced with a viral vector (e.g. lentiviral vector) encoding an anti-CD19 chimeric antigen receptor (CAR). The CD4+ and CD8+ cell compositions were then separately cultivated for expansion in the presence of media containing recombinant human cytokines (e.g. IL-2, IL-7 and/or IL-15). Prior to or during expansion, the beads were removed from the cell compositions by exposure to a magnetic field. After reaching a threshold for expansion, cells from each composition were separately harvested, formulated and cyrofrozen.

Twenty two separately generated T cell compositions were thawed and the presence or absence of residual beads present in the samples, without further spiking in additional paramagnetic bead particles, was compared using manual and automatic fluorescent imaging methods. The methods to assess residual beads were substantially the same as described in Example 1. In both methods cells were lysed prior to analysis with a bleach based lysis buffer and the number of residual beads in the lysate were enumerated. However, the steps for sample preparation and bead detection differed between the methods.

Specifically, a sample containing approximately 400 µL of an engineered cell composition was centrifuged to recover cells and bead particles, and then any residual beads were recovered by lysis following resuspension of the centrifuged samples in a lysis buffer (800 µL 1× phosphate-buffered saline with 0.1% Tween-20 (PBST); 200 µL of 8.25% bleach) and incubation for approximately 2 minutes at room temperature. Lysed samples were placed on a magnet designed for the paramagnetic polystyrene beads for 2 minutes, to separate the paramagnetic bead particles from cell debris and to enrich the sample for any residual beads, if present. The sample was processed for enumeration to assess the presence or absence of residual beads using the manual method or the automatic fluorescent method.

For the manual counting method, after lysis and exposure of the sample to the magnet, the supernatant was removed and the sample was resuspended in less than or equal to 30 µL PBST. The sample was loaded into the sample reservoir area of a hemocytometer for manual counting by microscopy. In this method, standard pipette tips were used throughout the lysis and enumeration steps. The total number of beads/mL in each sample were calculated by (number of sample beads+number of wash beads)/0.4 mL=total number of beads/mL.

For the automatic fluorescent imaging method, after lysis and exposure of the sample to the magnet, the supernatant was removed and the residual beads from the sample were washed twice with 1 mL PBST. The washed beads were resuspended in 75 µL PBST, vortexed for 30 seconds, and loaded onto a well in a 384-well plate. Another 75 µL of PBST was used to rinse the sides of the test tubes (wash beads) and loaded onto another well of the 384-well plate. Low retention pipette tips were used throughout the lysis and enumeration steps of the exemplary method. Images from the samples in the 384-well assay plate were collected with Cytation™ 5 Cell Imaging Multi-Mode Reader (BioTek Instruments, Inc., Winooski, VT) using both a brightfield and a Cy5 fluorescent filter channels (to detect autofluorescence of the beads) at 10× magnification, then overlaid and processed to reduce background interference. Beads in the images were distinguished from cells or other debris visually and automatically using the image processing software Gen5 on the imaging platform, based on size, fluorescent signal and circularity, to count the number of bead particles in the sample and calculate the concentration of the beads in a given sample as described in above and in Table 1a. The total number of beads/mL in each sample were calculated by (number of sample beads+number of wash beads)/0.4 mL=total number of beads/mL.

Figure 5A:
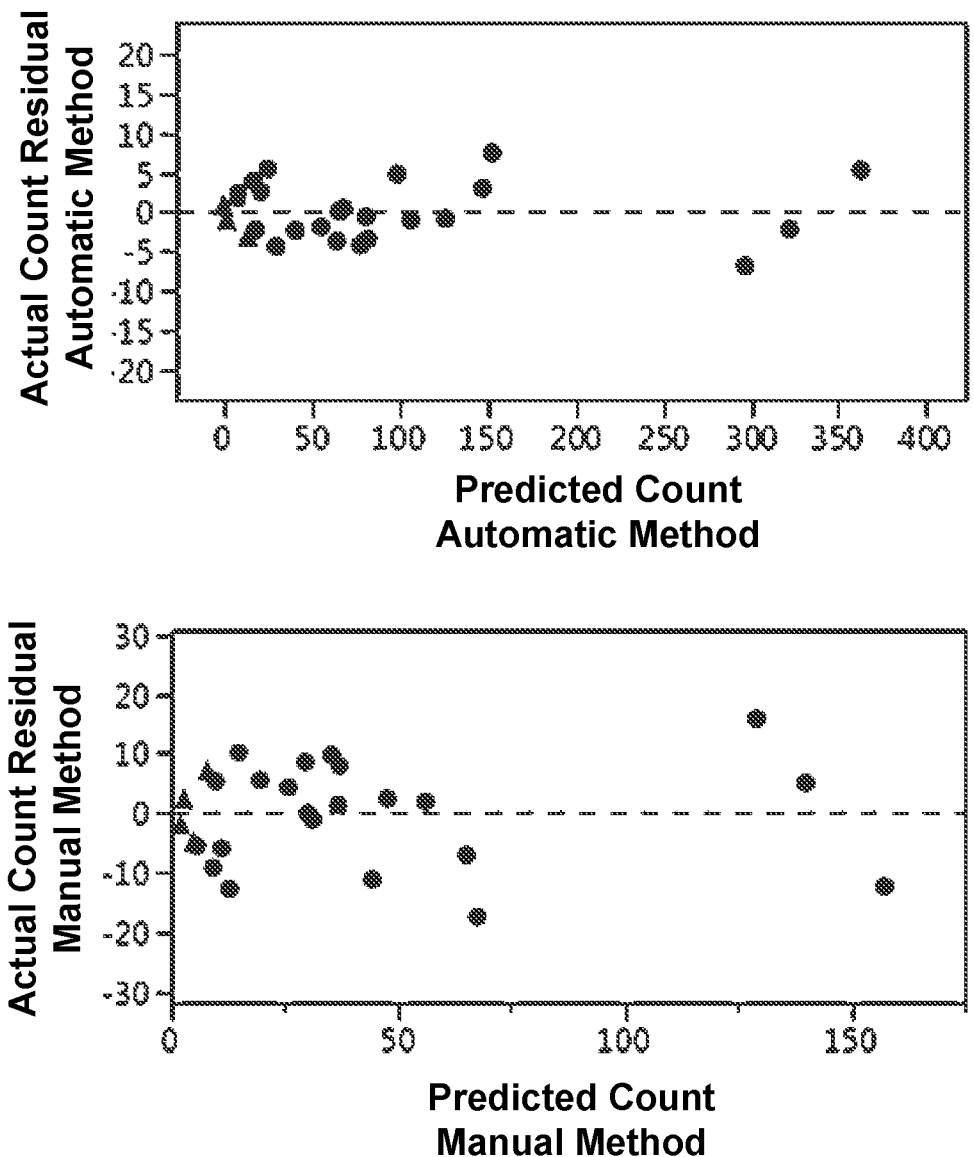
FIGS. 5A and 5B compare automatic and manual bead counts in non-spiked cell compositions.

Among the tested samples, eleven (11) samples had results below the lower limit of qualification (LLOQ) for both residual bead methods (LLOQ for manual method is about 20 beads/mL; LLOQ for automatic fluorescent method is about 50 beads/mL). FIG. 5A shows a comparison of the predicted versus residual bead counts by each of the automatic fluorescent or manual counting methods. Across all samples measured, the model residuals (actual count expected count) did not show a systematic trend for either method, and were evenly distributed around zero. The results were consistent with an observation that both models described a linear relationship between the actual and expected bead counts. Applying alternative statistical models yielded similar results.

Figure 5B:
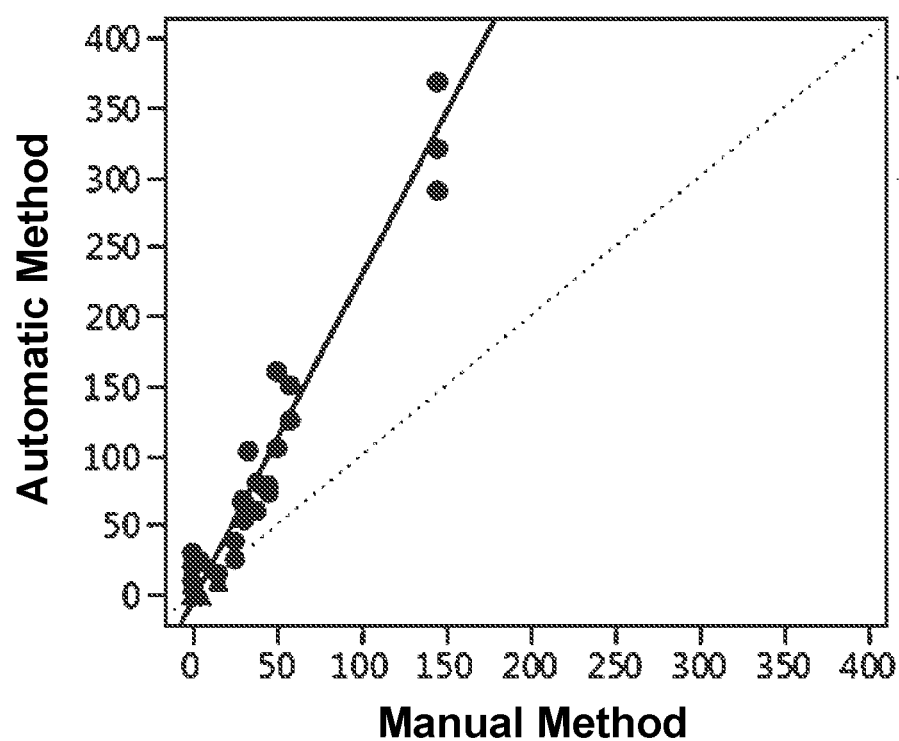

For all samples in which residual beads could be counted, there was a proportional bias towards higher bead count using the automatic fluorescent method compared to the manual method. Because the results in FIG. 5A indicated an evenly distributed trend for both methods of the actual versus predicted values, a linear error-in-variable (EIV) model was used to model the relationship between the two methods. As shown in FIG. 5B, the model to describe the relationship is as follows: automatic fluorescent count=−5.34+2.34×manual count, where the slope is 2.34 with the 95% confidence interval of (2.21, 2.56), and the intercept is −5.34 with the 95% CI of (−17.6, 6.92).

The results are consistent with the utility of this method for detecting residual beads in engineered cell samples that had previously been incubated with beads prior to steps to promote their removal (e.g. magnet), i.e non-spiked bead samples. These results showed that a higher residual bead count was possible with the automatic fluorescent method compared to the manual counting method from the same sample. This result is likely due to the improved recovery of residual beads as a result of differences in bead detection methods (e.g. automatic fluorescent vs. manual counting) and additional sample preparation steps in the automatic fluorescent method, such as extra wash steps, sample mixing (e.g. vortexing), low retention pipette tips, higher volume of sample for analysis, e.g. 75 µL compared to 30 µL. Further, the automatic fluorescent method permitted an increased throughput in processing of the samples.

Example 3: Assessment of Cell Concentration on Bead Enumeration by Automated Fluorescent Bead Enumeration Methods The automated fluorescent bead enumeration method described in Examples 1 and 2 was used to quantify the number of bead particles in cell compositions of different cell concentrations. Engineered CD4+ or CD8+ T cell compositions from human donors were generated substantially as described in Example 2. As described, the process for producing the cells included incubation of the cells with paramagnetic polystyrene-coated bead particles coated with anti-CD3 and anti-CD28 antibodies prior to introduction of nucleic acids encoding a CAR, followed by a step to remove the bead particles by exposure to a magnetic field.

To assess if cells in the composition interfered with the enumeration method, six cell composition samples were prepared at a concentration of $7\times10^7$ cells/mL (high cell concentration), and six samples were prepared at a concentration of $5\times10^7$ cells/mL (lower cell concentration). Three of the high cell concentration samples and three of the lower cell concentration samples were each spiked with a defined number of bead particles (400 Beads/mL) to assess the specificity, linearity, accuracy, precision and range of the method. The other three high cell concentration samples and three low cell concentration samples were not spiked with beads ("non-spiked"), such that enumeration of beads in these samples represents the real presence or absence of residual beads in the samples after the process for engineering the cells.

Spiked and non-spiked engineered cell compositions as described above were mixed by vortexing and subject to lysis and automated bead enumeration substantially as described in Example 2. The specificity of the method was evaluated by analyzing the bead count in three samples each of: (1) non-spiked, low cell concentration engineered cell compositions; (2) non-spiked, high cell concentration engineered cell compositions; (3) spiked, low cell concentration engineered cell compositions; and (4) spiked, high cell concentration engineered cells.

As shown in Table 9, the bead concentration in all six non-spiked samples was below the limit of quantitation (LOQ) of the method. In the non-spiked samples, there was no substantial difference in the observed bead concentration among the samples of different cell concentrations, indicating that no significant interference from cell concentration was observed.

For the spiked samples, the average bead count of the spiked samples with lower cell concentration was determined to be 443±17 beads/mL, while the average bead count of the spiked samples with higher cell concentration was determined to be 450±27 beads/mL. These values were determined to be statistically equivalent. This result supports the conclusion that there is no apparent interference from the cells using the automated fluorescent method for enumerating beads.

TABLE 9

Assessment of Specificity in Spiked and Non-Spiked Cell Compositions

| Sample | Sample No. | Observed bead concentration (Beads/mL) |
|---|---|---|
| Non-spiked $5 \times 10^7$ cells/mL | 1 | 8 (<LOQ) |
|  | 2 | 5 (<LOQ) |
|  | 3 | 8 (<LOQ) |
| Non-spiked $7 \times 10^7$ cells/mL | 1 | 33 (<LOQ) |
|  | 2 | 13 (<LOQ) |
|  | 3 | 5 (<LOQ) |
| Spiked $5 \times 10^7$ cells/mL | 1 | 418 |
|  | 2 | 475 |
|  | 3 | 435 |
| Spiked $7 \times 10^7$ cells/mL | 1 | 428 |
|  | 2 | 418 |
|  | 3 | 503 |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for detecting the presence or absence of beads in a cell composition, the method comprising the steps of:
   a) incubating a sample comprising at least a portion of an input composition or a sample derived from the input composition, wherein said input composition comprises one or more cells and is likely to comprise or may comprise one or more beads in which said one or more beads is capable of emitting an autofluorescence, wherein the incubating is under conditions to induce lysis of cells to produce an output composition; and
   b) analyzing the output composition or a portion thereof by fluorescence imaging of the autofluorescence of the one or more beads and by bright field imaging, to obtain a fluorescent image and a brightfield image and determine the presence or absence of the one or more beads in the sample.

2. A method for detecting the presence or absence of beads in a cell composition, the method comprising analyzing an output composition or a portion thereof by fluorescence imaging of an autofluorescence and by brightfield imaging to determine the presence or absence of beads in the output composition, wherein the output composition is a sample of at least a portion of an input composition that has been incubated under conditions to induce lysis of cells, wherein the input composition comprises one or more of the cells and is likely to comprise or may comprise one or more beads in which said one or more beads is capable of emitting the autofluorescence.

3. The method of claim 1, wherein the one or more beads is a residual bead present in the input composition following a step to remove or reduce beads from a cell composition comprising the one or more cells and one or more beads.

4. The method of claim 1, wherein prior to the analyzing the output composition is enriched for the one or more beads by a step involving selecting for the one or more beads present in the output composition.

5. A method for detecting the presence or absence of beads in a cell composition, the method comprising:
   (a) processing a cell composition comprising cells and beads under conditions to remove or reduce the beads of the cell composition, thereby producing an input composition comprising one or more of the cells and that may comprise one or more beads that is a residual bead, wherein the one or more beads is capable of emitting an autofluorescence;
   (b) incubating a sample comprising at least a portion of the input composition or a sample derived from the input composition, wherein the incubating is under conditions to induce lysis of the one or more cells to produce an output composition;
   (c) enriching for the one or more beads in the output composition by a step involving selecting for the one or more beads present in the output composition to produce an enriched output composition; and
   (d) analyzing the enriched output composition or a portion thereof by fluorescence imaging of the autofluorescence and by brightfield imaging to determine the presence or absence of residual beads in the sample.

6. The method of claim 4, wherein the one or more beads are magnetic or paramagnetic and the selection comprises exposing the beads to a magnet or magnetic field.

7. The method of claim 1, wherein the analyzing the output composition by fluorescence imaging comprises obtaining a fluorescent image of the output composition or a portion thereof and determining fluorescent intensity of image objects from the fluorescent image.

8. The method of claim 7, wherein analyzing the composition by bright field imaging comprises assessing the size, area, and/or circularity of image objects from the fluorescent image and/or brightfield image.

9. A method for detecting the presence or absence of beads in a cell composition, the method comprising
   (i) illuminating an output composition or a portion thereof with one or more light sources to generate an illuminated sample, wherein at least one light source is capable of exciting an autofluorescence, wherein said output composition is a sample of at least a portion of an input composition that has been incubated under conditions to induce lysis of cells, wherein the input composition comprises one or more of the cells and is likely to comprise or may comprise one or more beads in which said one or more beads is capable of emitting the autofluorescence;
   (ii) capturing at least one fluorescent image, and at least one brightfield image of the illuminated sample; and
   (iii) analyzing the presence or absence of image objects from the one or more images for one or more parameters selected from size, area, fluorescent intensity, brightfield intensity, and/or circularity, thereby determining the presence or absence of one or more beads.

10. The method of claim 9, wherein prior to the illuminating the output composition is enriched for the one or more beads by a step involving selection for the one or more beads.

11. The method of claim 10, wherein the one or more beads is magnetic or paramagnetic and the selection comprises magnetic selection.

12. The method of claim 1, wherein the analyzing detects singlets, doublets or singlets and doublets of the beads.

13. The method of claim 7, wherein an image object is detected as a bead if the image object comprises a fluorescent signal, and:
(i) the image object comprises a circularity of 0.4 or more;
(ii) the image object comprises a diameter of between 1 µm and 20 µm, inclusive; and/or
(iii) the image object comprises an area of less than 130 µm².

14. The method of claim 1, wherein:
(A) an image object is detected as a singlet bead if the image object comprises a fluorescent signal, and:
(i) the image object comprises a circularity of at or at least 0.7;
(ii) the image object comprises a diameter of between 1 µm and 7.5 µm, inclusive; and/or
(iii) the image object comprises an area of less than 65 µm²; and
(B) an image object is detected as a doublet bead if the image object comprises a fluorescent signal, and:
(i) the image object comprises a circularity of between or between about 0.4 and 0.6;
(ii) the image object comprises a diameter of between 2 µm and 15 µm, inclusive; and/or
(iii) the image object comprises an area of less than 130 µm².

15. The method of claim 13, wherein a control sample is a composition produced by incubating a cell composition comprising the one or more cells but not comprising the one or more beads wherein the incubating is under conditions to induce lysis of cells to produce an output composition.

16. The method of claim 1, wherein the analyzing further comprises enumerating the number of beads determined to be present in the sample.

17. The method of claim 1, wherein:
the analyzing is carried out using a computer-implemented image analysis;
one or more steps of the method is carried out by a machine, a robot and/or a computer-implemented algorithm; and/or
wherein one or more steps of the method is high-throughput and/or automated.

18. The method of claim 1, wherein the input composition is derived from a cell composition, said cell composition comprising one or more cells and one or more of the beads in which said one or more beads comprises a biomolecule capable of binding to a macromolecule on the surface of the one or more cells.

19. The method of claim 1, wherein the incubating under conditions to induce lysis of cells comprises incubating the sample with a solution comprising a bleach.

20. The method of claim 19, wherein the solution comprising bleach further comprises a detergent.

21. The method of claim 19, wherein the incubating under conditions to induce lysis of cells comprises incubating the sample with bleach wherein the sample is incubated with bleach at a concentration of about 0.1%, 0.2%, 0.3%, 0.4%, 0.5%, 1%, 1.5%, 2%, 3%, 4%, 5%, 6%, 7% or 8% (v/v) bleach, or a range defined by any two of the foregoing values.

22. The method of claim 20, wherein the detergent is one or more of Triton X-100, Triton X-114, NP-40, Brij-35, Brij-58, Tween 20, Tween 80, digitonin, octyl glucoside, octyl thioglucoside, sodium dodecyl sulfate (SDS), 3-[(3-cholamidopropyl)dimethylammonio]-1-propanesulfonate (CHAPS) and CHAPSO.

23. The method of claim 20, wherein the detergent is or comprises Tween 20.

24. The method of claim 1, wherein the concentration of cells in the sample of at least a portion of the input composition is at least or at least about $2 \times 10^5$ cells/mL.

25. The method of claim 1, wherein the volume of the output composition or a portion thereof is at or about or is at least at or about 50 µL.

26. The method of claim 1, wherein prior to the analyzing the method comprises mixing the output composition under conditions to agitate the one or more cell particles in the sample.

27. The method of claim 1, wherein during the one or more steps of the method the output composition is processed under conditions to reduce sample retention on a surface during the processing.

28. The method of claim 1, wherein one or more of the beads has a diameter of 1.0 µm to 10.0 µm or 1.0 µm to 5.0 µm.

29. The method of claim 1, wherein one or more of the beads comprise a magnetic core, a paramagnetic core or a superparamagnetic core.

30. The method of claim 1, wherein the one or more beads is or comprises a polystyrene surface.

31. The method of claim 18, wherein the one or more biomolecules is present on, or attached to, the surface of the one or more beads.

32. The method of claim 18, wherein the one or more biomolecules is selected from the group consisting of an affinity reagent capable of selecting, isolating or enriching one or more cells in sample, and a stimulatory agent or agents capable of stimulating one or more cells in the sample.

33. The method of claim 30, wherein one or more biomolecules is present on, or attached to, the surface of the one or more beads, and wherein the one or more biomolecules is a stimulatory agent or agents capable of stimulating one or more cells in the sample.

34. The method of claim 1, wherein the incubating is performed at a temperature that is about 15° C. to 30° C.

35. An article of manufacture, comprising:
a container comprising a solution comprising bleach and/or detergent for effecting cell lysis;
packaging material; and
a label or package insert comprising instructions for detecting the presence or absence of beads in a cell composition; wherein the instructions specify carrying out the steps of the method of claim 1.

36. The method of claim 19, wherein the bleach is a chlorine-based bleach.

* * * * *